US012624073B2

(12) United States Patent
Pfenning et al.

(10) Patent No.: US 12,624,073 B2
(45) Date of Patent: May 12, 2026

(54) SPECIFIC NUCLEAR-ANCHORED INDEPENDENT LABELING SYSTEM

(71) Applicant: Carnegie Mellon University, Pittsburgh, PA (US)

(72) Inventors: Andreas R. Pfenning, Pittsburgh, PA (US); Easwaran Ramamurthy, Pittsburgh, PA (US); Alyssa Lawler, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 1041 days.

(21) Appl. No.: 17/618,798

(22) PCT Filed: Jun. 18, 2020

(86) PCT No.: PCT/US2020/038520
§ 371 (c)(1),
(2) Date: Dec. 13, 2021

(87) PCT Pub. No.: WO2020/257516
PCT Pub. Date: Dec. 24, 2020

(65) Prior Publication Data
US 2022/0235102 A1     Jul. 28, 2022

Related U.S. Application Data

(60) Provisional application No. 62/921,452, filed on Jun. 18, 2019.

(51) Int. Cl.
| | |
|---|---|
| *C07K 14/47* | (2006.01) |
| *C12N 15/86* | (2006.01) |
| *G06N 3/045* | (2023.01) |
| *G06N 3/047* | (2023.01) |
| *G06N 20/10* | (2019.01) |
| *G16B 30/10* | (2019.01) |
| *G16B 40/00* | (2019.01) |

(52) U.S. Cl.
CPC ............. *C07K 14/47* (2013.01); *C12N 15/86* (2013.01); *G06N 3/045* (2023.01); *G06N 3/047* (2023.01); *G06N 20/10* (2019.01); *C07K 2319/03* (2013.01); *C07K 2319/60* (2013.01); *C12N 2750/14143* (2013.01); *G16B 30/10* (2019.02); *G16B 40/00* (2019.02)

(58) Field of Classification Search
None
See application file for complete search history.

(56) References Cited

U.S. PATENT DOCUMENTS

| | | | | |
|---|---|---|---|---|
| 4,959,317 A | * | 9/1990 | Sauer | C12N 15/81 |
| | | | | 435/254.2 |
| 5,580,859 A | | 12/1996 | Felgner et al. | |
| 5,589,466 A | | 12/1996 | Felgner et al. | |

| | | | | |
|---|---|---|---|---|
| 2012/0124685 A1 | * | 5/2012 | Henikoff | C12N 15/1003 |
| | | | | 435/351 |
| 2012/0254077 A1 | | 10/2012 | Porikli et al. | |
| 2020/0347408 A1 | * | 11/2020 | Stewart | C07K 14/47 |
| 2022/0310206 A1 | | 9/2022 | Pfenning et al. | |

FOREIGN PATENT DOCUMENTS

| | | | | |
|---|---|---|---|---|
| WO | WO 2006/091638 | 8/2006 | | |
| WO | WO 2018/138478 | 8/2018 | | |
| WO | WO-2018138478 A1 | * | 8/2018 | ........... C12N 5/0629 |
| WO | WO 2020/257516 | 12/2020 | | |
| WO | WO 2020/257520 | 12/2020 | | |

OTHER PUBLICATIONS

Brown, et al. Constructing strong cell type-specific promoters through informed design. Methods in Molecular Biology. (1651)131:45. Aug. 12, 2017. (Year: 2017).*
Al-Rubeai. 2011. Methods in Molecular Biology. Viral Vectors for Gene Therapy; Ch. 8. (Year: 2011).*
International Preliminary Report on Patentability in International Application No. PCT/US2020/038520, dated Dec. 30, 8 pages.
International Preliminary Report on Patentability in International Application No. PCT/US2020/038528, dated Dec. 30, 2021, 11 pages.
International Preliminary Report on Patentability in International Application No. PCT/US2020/038520, dated Dec. 30, 2021, 8 pages.
[github.com] online, "NuDup," retrieved on Feb. 4, 2025, retrieved from URL<github.com/tecagenomics/nudup>, 4 pages.
github.com [online], "LS-GKM: A new gkm-SVM software for large-scale datasets," retrieved on Feb. 4, 2025, retrieved from URL<https://github.com/Dongwon-Lec/lsgkm>, 5 pages.
github.com [online], "gplots," retrieved on Feb. 4, 2025, retrieved from URL<https://github.com/talgalili/gplots>, 3 pages.
Invitation to Pay Additional Fees in International Application No. PCT/US2020/038520, dated Oct. 2, 2020, 3 pages.
Lawler et al., "Machine learning sequence prioritization for cell type specific enhancer design," eLife, May 16, 2022, 11:e69571.
addgene.org [online], "pAAV-Efla-DIO-EGFP-WPRE-pA," Oct. 2015, retrieved on Dec. 17, 2021, retrieved from URL <"http://www.addgene.org/37084/">, 4 pages.
addgene.org [online], "pUCmini-iCAP-PHP.eB," May 2019, retrieved on Dec. 17, 2021, retrieved from URL <"https://www.addgene.org/103005/">, 3 pages.

(Continued)

*Primary Examiner* — Allison M Fox
*Assistant Examiner* — Gina Pronzati
(74) *Attorney, Agent, or Firm* — Fish & Richardson P.C.

(57) ABSTRACT

Materials and methods for labeling and isolating particular cell types from mixed cell populations are provided herein. Also provided herein are methods for generating data representing a synthetic genetic sequence configured for labeling at least one cell type by causing expression of a marker in the at least one cell type.

22 Claims, 32 Drawing Sheets

Specification includes a Sequence Listing.

(56)            References Cited

OTHER PUBLICATIONS

Atasoy et al., "A FLEX Switch Targets Channelrhodopsin-2 to Multiple Cell Types for Imaging and Long-Range Circuit Mapping," The Journal of Neuroscience, Jul. 2008, 28(28): 7025-7030.
Bais et al., "scds: computational annotation of doublets in single-cell RNA sequencing data," Bioinformatics, Sep. 2019, 36(4): 1150-1158.
Broadinstitute.github.io [online], "Picard," Oct. 5, 2014, retrieved on Dec. 17, 2021, retrieved from URL <"http://broadinstitute.github.io/picard/">, 5 pages.
Buenrostro et al., "ATAC-seq: A Method for Assaying Chromatin Accessibility Genome-Wide," Current Protocols in Molecular Biology, Jan. 2015, 109: 21.29.1-21.29.9.
Buenrostro et al., "Transposition of native chromatin for fast and sensitive epigenomic profiling of open chromatin, DNA-binding proteins and nucleosome position," Nature Methods, Oct. 2013, 10(12): 1213-1218.
Chan et al., "Engineered AAVs for efficient noninvasive gene delivery to the central and peripheral nervous systems," Nature Neuroscience, Jun. 2017, 20:1172-1179.
Coffin, "Retroviridae: The viruses and their replication," Fundamental Virology, Third Edition, Fields et al. (eds.), Lippincott-Raven Publishers, Philadelphia, 1996, Chapter 26, 83 pages.
Dengler et al., "Transcriptional regulation by hypoxia inducible factors," Critical Reviews in Biochemistry and Molecular Biology, 2014, 49(1): 1-15.
Ghandi et al., "Enhanced Regulatory Sequence Prediction Using Gapped k-mer Features," Plos Computational Biology, Jul. 17, 2014, 10(7):e1003711, 16 pages.
github.com [online], "kundajelab/atac_dnase_pipelines," 2018, retrieved on Dec. 17, 2021, retrieved from URL <"github.com/kundajelab/atac_dnase_pipelines">, 21 pages.
github.com [online], "timoast/signac," Sep. 13, 2021, retrieved on Dec. 17, 2021, retrieved from URL <"https://github.com/timoast/signac">, 3 pages.
Gjoneska et al., "Conserved epigenomic signals in mice and humans reveal immune basis of Alzheimer's disease," Nature, Feb. 18, 2015, 518(7539): 365-369.
Griffiths et al., "Detection and removal of barcode swapping in single-cell RNA-seq data," Nature Communications, Jul. 2018, 9: 2667, 6 pages.
Gu et al., "circlize implements and enhances circular visualization in R," Bioinformatics, Oct. 2014, 30(19): 2811-2812.
Haque et al., "Mammalian SUN Protein Interaction Networks at the Inner Nuclear Membrane and Their Role in Laminopathy Disease Processes*," Journal of Biological Chemistry, Jan. 2010, 285(5): 3487-3498.
Herrero et al., "Inflammation in Parkinson's disease: role of glucocorticoids," Frontiers in Neuroanatomy, Apr. 2015, 9:1-12.
Hioki, "Compartmental organization of synaptic inputs to parvalbumin-expressing GABAergic neurons in mouse primary somatosensory cortex," Anat. Sci. Int., Dec. 3, 2014, 90(1):7-21.
International Search Report and Written Opinion and International Application No. PCT/US2020/038528, dated Sep. 30, 2020, 12 pages.
International Search Report and Written Opinion in International Application No. PCT/US2020/038520, dated Dec. 17, 2020, 12 pages.
Khan et al., "JASPAR 2018: update of the open-access database of transcription factor binding profiles and its web framework," Nucleic Acids Res., Jan. 2018, 46(D1): D260-D266.
Kim et al., "A pivotal role of matrix metalloproteinase-3 activity in dopaminergic neuronal degeneration via microglial activation," FASEB Journal, Nov. 2006, 21(1):179-187.
Li et al., "Measuring reproducibility of high-throughput experiments," The Annals of Applied Statistics, Sep. 2011, 5(3): 1752-1779.

Liao et al., "The R package Rsubread is easier, faster, cheaper and better for alignment and quantification of RNA sequencing reads ," Nucleic Acids Research, May 2019, 47(8): e47, 9 pages.
Love et al., "Moderated estimation of fold change and dispersion for RNA-seq data with DESeq2, "Genome Biology, 2014, 15: 550, 21 pages.
Lun et al., "A step-by-step workflow for low-level analysis of single-cell RNA-seq data with Bioconductor," F1000Res, 2016, 5: 2122, 64 pages.
Lun et al., "Pooling across cells to normalize single-cell RNA sequencing data with many zero counts," Genome Biology, Apr. 2016, 17: 75, 14 pages.
Madisen et al., "A robust and high-throughput Cre reporting and characterization system for the whole mouse brain," Nature Neuroscience, Dec. 2009, 13(1): 133-140.
Mastro et al., "Cell-specific pallidal intervention induces long-lasting motor recovery in dopamine-depleted mice," Nature Neuroscience, May 2017, 20: 815-823.
McInnes et al. "UMAP: Uniform Manifold Approximation and Projection for Dimension Reduction," arXiv:1802.032426, 2018, 63 pages.
McLean et al., "GREAT improves functional interpretation of cis-regulatory regions," Nature Biotechnology, May 2010, 28: 495-501.
McLeay et al., "Motif Enrichment Analysis: a unified framework and an evaluation on ChIP data," BMC Bioinformatics, Apr. 2010, 11:165, 11 pages.
Meng et al. "Construction of precise support vector machine based models for predicting promoter strength," Quantitative Biology, Mar. 30, 2017, 5(1): 90-98.
Mo et al., "Epigenomic Signatures of Neuronal Diversity in the Mammalian Brain," Neuron, Jun. 2015, 86(6):1369-1384.
ncbi.nlm.nih.gov [online], "NCBI Ref. NM_001256118.1: Mus musculus adenosine deaminase-like (Adal), transcript variant 2, mRNA," Feb. 13, 2021, retrieved on Dec. 16, 2021, retrieved from URL <"https://www.ncbi.nlm.nih.gov/nuccore/NM_001290811.1">, 3 pages.
Ohh et al., "Ubiquitination of hypoxia-inducible factor requires direct binding to the β-domain of the von Hippel-Lindau protein," Nature Cell Biology, Jun. 2000, 2: 423-427.
Ongwijitwat et al., "Nuclear respiratory factor 2 senses changing cellular energy demands and its silencing down-regulates cytochrome oxidase and other target gene mRNAs," Gene, Jun. 2006, 374:39-49.
Pozniak et al., "Sox10 directs neural stem cells toward the oligodendrocyte lineage by decreasing Suppressor of Fused expression," Proceedings of the National Academy of Sciences of the United States of America, Dec. 2010, 107(50):21795-21800.
Raudvere et al., "g:Profiler: a web server for functional enrichment analysis and conversions of gene lists (2019 update)," Nucleic Acids Research, Jul. 2019, 47(W1):W191-W198.
Rosenberg, "Matrix metalloproteinases and their multiple roles in neurodegenerative diseases," The Lancet Neurology, Feb. 2009, 8(2):205-216.
Saunders et al., "Molecular Diversity and Specializations among the Cells of the Adult Mouse Brain," Cell, Aug. 2018, 174: 1015-1030. e16.
Saunders et al., "Novel recombinant adeno-associated viruses for Cre activated and inactivated transgene expression in neurons," Front Neural Circuits, Jul. 2012, 6:47.
Schindelin et al., "Fiji: an open-source platform for biological-image analysis," Nature Methods, Jun. 2012, 9:676-682.
Schofield et al., "Oxygen sensing by HIF hydroxylases," Nature Reviews Molecular Cell Biology, May 2004, 5: 343-354.
Short Protocols in Molecular Biology, Green Publishing Associates and John Wiley & Sons, Ausubel et al. (ed.), 1992, Chapter 8, 28 pages.
Smeyne et al., "HIF1α is necessary for exercise-induced neuroprotection while HIF2α is needed for dopaminergic neuron survival in the substantia nigra pars compacta," Neuroscience, Jun. 2015, 295:23-38.
Sorensen et al., "A robust activity marking system for exploring active neuronal ensembles," eLife, Sep. 2016, 5:e13918, 28 pages.

(56)          References Cited

OTHER PUBLICATIONS

Stockwell et al., "Ferroptosis: A Regulated Cell Death Nexus Linking Metabolism, Redox Biology, and Disease," Cell, Oct. 2017, 171(2): 273-285.

Stuart et al., "Single-cell chromatin state analysis with Signac," Nature Methods, Nov. 2021, 18: 1333-1341.

Takada et al., "Sox10 is necessary for oligodendrocyte survival following axon wrapping," Glia, Mar. 2010, 58(8): 996-1006.

Traag et al., "From Louvain to Leiden: guaranteeing well-connected communities," Scientific Reports, Mar. 2019, 9: 5233, 12 pages.

Wang et al., "Synthetic Promoter Design in *Escherichia coli* based on Generative Adversarial Network," bioRxiv, Apr. 25, 2019, 10 pages.

Wolf et al., "SCANPY: large-scale single-cell gene expression data analysis," Genome Biology, Feb. 2018, 19: 15, 5 pages.

Woodruff et al., "Networks of Parvalbumin-Positive Interneurons in the Basolateral Amygdala," The Journal of Neuroscience, Jan. 17, 2007, 27(3): 553-563.

U.S. Appl. No. 17/619,783, filed Dec. 16, 2021, Andreas R. Pfenning.

* cited by examiner

Sample Distances Between Viral Probe and Transgenic Methods

250

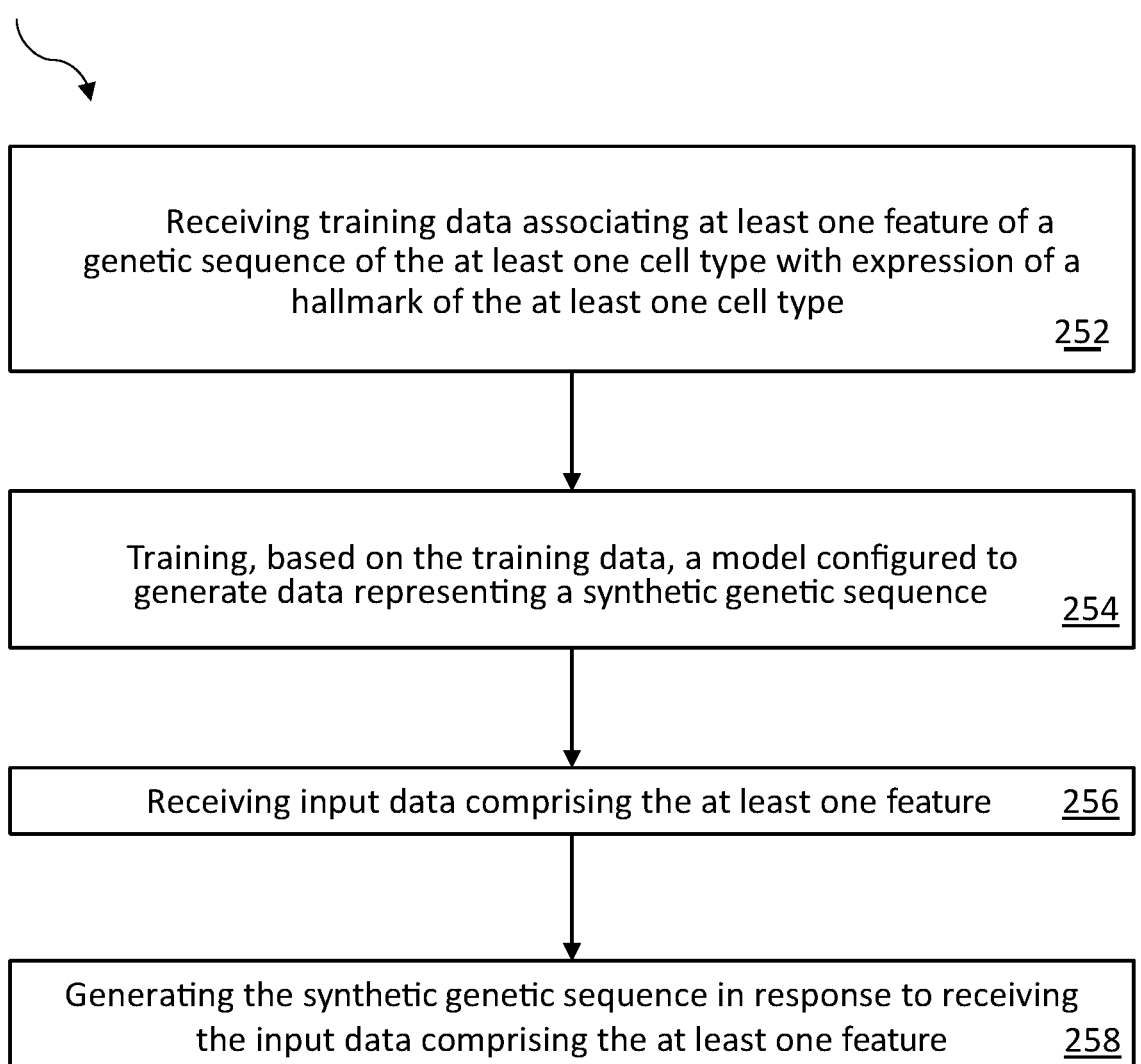

Receiving training data associating at least one feature of a genetic sequence of the at least one cell type with expression of a hallmark of the at least one cell type    252

Training, based on the training data, a model configured to generate data representing a synthetic genetic sequence    254

Receiving input data comprising the at least one feature    256

Generating the synthetic genetic sequence in response to receiving the input data comprising the at least one feature    258

FIG. 2A

|  | Cortex | Striatum | GPe |
|---|---|---|---|
| Specificity ●/(●+○) | 94.0% ± 0.7 | 94.1% ± 2.8 | 94.5% ± 0.6 |
| Efficiency ●/(●+●) | 80.7% ± 2.3 | 55.2% ± 4.8 | 53.3% ± 1.3 |
| Expected transduction | 69% | 55% | ND |

FIG. 8C
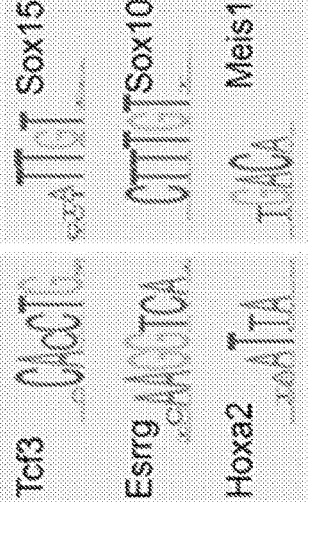
FIG. 8F
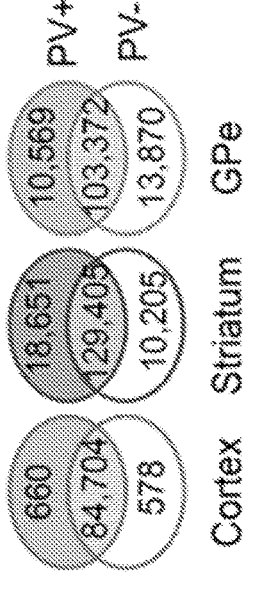
FIG. 8B
Marker Gene Expression
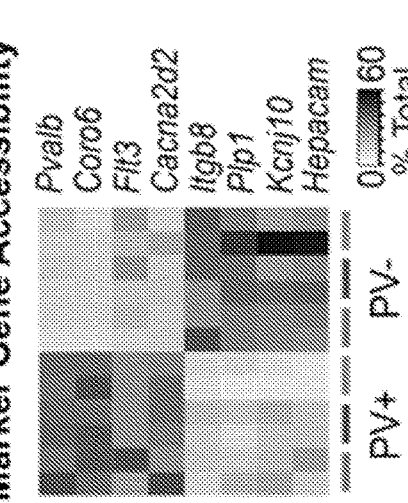
FIG. 8E
Marker Gene Accessibility
FIG. 8A
Differentially Expressed Genes
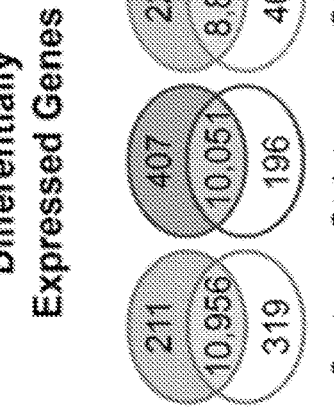
FIG. 8D
Differentially Accessible Chromatin

| RNA-seq | Cortex PV+ | Cortex PV- | Striatum PV+ | Striatum PV- | GPe PV+ | GPe PV- |
|---|---|---|---|---|---|---|
| Genes Tested | 26245 | 26860 | 25149 | 24737 | 17430 | 26325 |
| ↑ in DD | 0 | 0 | 0 | 0 | 14 | 0 |
| ↓ in DD | 0 | 3 | 0 | 0 | 15 | 3 |

$p_{adj} < 0.05$

FIG. 9A

Remaining Dopamine per Hemisphere p < 0.003

Mean Intensity of Striatal Tyrosine Hydroxylase (RFU)

10,000

5,000

0

6-OHDA          Sham

Example Anti-Tyrosine Hydroxylase Images

Cortex

Striatum

6-OHDA          Sham

FIG. 12B

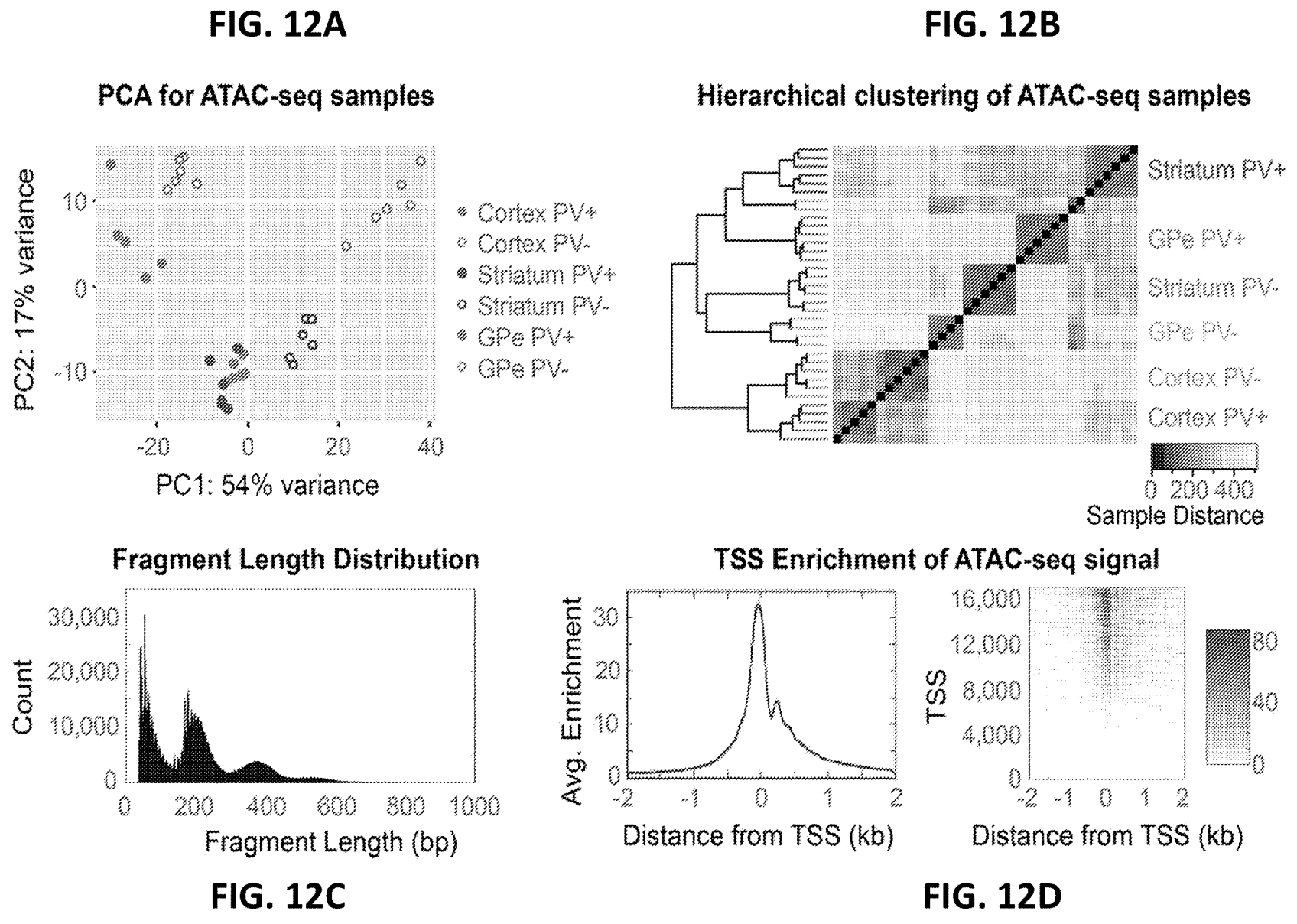

Hierarchical clustering of ATAC-seq samples

FIG. 12A

PCA for ATAC-seq samples

PC2: 17% variance

PC1: 54% variance

- Cortex PV+
- Cortex PV-
- Striatum PV+
- Striatum PV-
- GPe PV+
- GPe PV-

FIG. 12D

TSS Enrichment of ATAC-seq signal

TSS

Distance from TSS (kb)

FIG. 12C

Fragment Length Distribution

Count

Fragment Length (bp)

TSS Enrichment

Avg. Enrichment

Distance from TSS (kb)

Sample Distance

FIG. 13B

FIG. 13A cSNAIL PV- marker gene expression in scRNA-seq cSNAIL PV+ marker gene expression in scRNA-seq

SPECIFIC NUCLEAR-ANCHORED INDEPENDENT LABELING SYSTEM

CROSS-REFERENCE TO RELATED APPLICATIONS

This application is a U.S. National Stage Application under 35 U.S.C. § 371 of International Application Serial No. PCT/US2020/038520, filed on Jun. 18, 2020, which claims benefit of priority from U.S. Provisional Application Ser. No. 62/921,452, filed Jun. 18, 2019. The disclosure of each of the prior applications is considered part of (and is incorporated by reference in) the disclosure of this application.

TECHNICAL FIELD

This document relates to materials and methods for labeling and subsequently isolating particular cell types from mixed cell populations.

BACKGROUND

The brain and other tissues consist of heterogeneous populations of cells with specialized properties and functions. Genetically and epigenetically distinguishable cell types are likely to play different roles and exhibit different responses in disease and other conditions. The vast majority of genomic assays, however, are conducted on bulk tissue and not individual cell types, making the results of such assays difficult to interpret and disentangle for cell type-specific mechanisms. Improved techniques for nuclei labeling and isolation are needed to solve this problem.

SUMMARY

This document is based, at least in part, on the development of compositions and methods for labeling and isolating specific populations of cells. The methods are referred to herein as SNAIL (Specific Nuclear-Anchored Independent Labeling) and cSNAIL (Cre-Specific Nuclear-Anchored Independent Labeling). cSNAIL and SNAIL provide improvements over current methods for nuclear isolation methods, as they are easier, more time-efficient, and more cost-effective, without any loss of selection. Moreover, cSNAIL and SNAIL have the added benefits of being compatible with multiplexing and other transgenic models, extending to new cell types, and being transferrable across species. The availability of this technology increases the practicality of cell type-specific genomics, and allows these approaches to be used in other mammals, including humans.

In a first aspect, this document features a nucleic acid construct containing (a) a sequence encoding a tagged Sun1 fusion polypeptide, where the tagged Sun1 fusion polypeptide comprises, consists of, or consists essentially of (i) an N-truncated fragment of a Sun1 gene, where the fragment encodes at least a portion of a portion of a Sun1 protein, and where the portion of the Sun1 protein is 400 to 600 amino acids in length, and (ii) a sequence encoding a tag polypeptide, and (b) a promoter sequence specific for a selected cell type, where the promoter sequence is operably linked to the sequence encoding the tagged Sun1 fusion polypeptide, and is effective to drive expression of the sequence encoding the tagged Sun1 fusion polypeptide in the selected cell type. (By "consists essentially of" is meant that a nucleic acid or a polypeptide contains specified components, and can contain additional sequences that do not materially affect the basic and novel characteristics of the nucleic acid or polypeptide.) The N-truncated fragment of the Sun1 gene can encode a polypeptide with at least 95% sequence identity to amino acids 208-757 of the mouse Sun1 protein having the amino acid sequence set forth in SEQ ID NO:1. The tag polypeptide can be a fluorescent polypeptide (e.g., a green fluorescent protein (GFP), such as a GFP with an amino acid sequence that at least 95% identical to the superfolder GFP sequence set forth in SEQ ID NO:2). The construct can further include virus sequences (e.g., adeno-associated virus (AAV) sequences or lentivirus sequences). The promoter sequence can be specific for parvalbumin positive (PV+) neurons, such the sequence encoding the tagged Sun1 fusion polypeptide is expressed in PV+ neurons but not expressed in at least 90% of parvalbumin negative (PV−) neurons.

In another aspect, this document features a nucleic acid construct containing (a) a sequence encoding a tagged Sun1 fusion polypeptide, where the tagged Sun1 fusion polypeptide comprises, consists of, or consists essentially of (i) an N-truncated fragment of a Sun1 gene, where the fragment encodes a portion of a Sun1 protein, and where the portion of the Sun1 protein is 400 to 600 amino acids in length, and (ii) a sequence encoding a tag polypeptide, (b) a first lox sequence flanking the 5' end of the sequence encoding the tagged Sun1 fusion polypeptide and a second lox sequence flanking the 3' end of the sequence encoding the tagged Sun1 fusion polypeptide, and (c) a promoter sequence downvnstream of the lox sequence flanking the 3' end of the sequence encoding the tagged Sun1 fusion polypeptide, such that the sequence encoding the tagged Sun1 fusion polypeptide is in reverse orientation with respect to the promoter. The N-truncated fragment of the Sun1 gene can encode a polypeptide with at least 95% sequence identity to amino acids 208-757 of the mouse Sun1 protein having the amino acid sequence set forth in SEQ ID NO:1. The tag polypeptide can be a fluorescent polypeptide (e.g., a GFP, such as a GFP having an amino acid sequence that is at least 95% identical to the superfolder GFP sequence set forth in SEQ ID NO:2). The construct can further include virus sequences (e.g., AAV sequences or lentivirus sequences).

This document also features virus particles (e.g., AAV or lentivirus particles) containing one or more nucleic acid constructs as described herein.

In another aspect, this document features a method for labeling a selected cell type within a population of different cell types, where the method includes introducing into the population of different cell types a nucleic acid construct containing (a) a sequence encoding a tagged Sun1 fusion polypeptide, where the tagged Sun1 fusion polypeptide comprises, consists of, or consists essentially of (i) an N-truncated fragment of a Sun1 gene, where the fragment encodes at least a portion of a portion of a Sun1 protein, and where the portion of the Sun1 protein is 400 to 600 amino acids in length, and (ii) a sequence encoding a tag polypeptide, and (b) a promoter sequence specific for a selected cell type, where the promoter sequence is operably linked to the sequence encoding the tagged Sun1 fusion polypeptide, and is effective to drive expression of the sequence encoding the tagged Sun1 fusion polypeptide in the selected cell type, and wherein the tagged Sun1 fusion polypeptide is expressed in and thereby labels the selected cell type. The N-truncated fragment of the Sun1 gene can encode a polypeptide with at least 95% sequence identity to amino acids 208-757 of the mouse Sun1 protein having the amino acid sequence set forth in SEQ ID NO:1. The tag polypeptide can be a fluorescent polypeptide (e.g., a GFP, such as a GFP having an amino acid sequence that is at least 95% identical to the superfolder GFP sequence set forth in SEQ ID NO:2). The construct can further include virus sequences (e.g., AAV sequences or lentivirus sequences). The promoter sequence can be specific for PV+ neurons, such that the sequence encoding the tagged Sun1 fusion polypeptide is expressed in PV+ neurons but not expressed in at least 90% of PV− neurons.

In another aspect, this document features a method for labeling a selected cell type within a population of different cell types, where the method includes (a) introducing into the population of different cell types (i) a first nucleic acid construct containing (1) a sequence encoding a tagged Sun1 fusion polypeptide and (2) a sequence encoding a tag polypeptide, where the tagged Sun1 fusion polypeptide comprises, consists of, or consists essentially of an N-truncated fragment of a Sun1 gene, where the fragment encodes a portion of a Sun1 protein, and wherein the portion of the Sun1 protein is 400 to 600 amino acids in length, and (2) a first lox sequence flanking the 5' end of the sequence encoding the tagged Sun1 fusion polypeptide and a second lox sequence flanking the 3' end of the sequence encoding the tagged Sun1 fusion polypeptide, and (3) a promoter sequence downstream of the lox sequence flanking the 3' end of the sequence encoding the tagged Sun1 fusion polypeptide, such that the sequence encoding the tagged Sun1 fusion polypeptide is in reverse orientation with respect to the promoter, and (ii) a second nucleic acid construct comprising a sequence encoding a Cre recombinase operably linked to a promoter sequence specific for the selected cell type, and (b) incubating the population of different cell types under conditions in which the Cre recombinase is expressed in the selected cell type, where the expressed Cre recombinase excises the sequence encoding the tagged Sun1 fusion polypeptide from the nucleic acid construct and irreversibly re-inserts the sequence encoding the tagged Sun1 fusion polypeptide in the correct orientation for expression in the selected cell type. The N-truncated fragment of the Sun1 gene can encode a polypeptide with at least 95% sequence identity to amino acids 208-757 of the mouse Sun1 protein having the amino acid sequence set forth in SEQ ID NO:1. The tag polypeptide can be a fluorescent polypeptide (e.g., a GFP, such as a GFP having an amino acid sequence that is at least 95% identical to the superfolder GFP sequence set forth in SEQ ID NO:2). The construct can further include virus sequences (e.g., AAV sequences or lentivirus sequences).

In still another aspect, this document features a method for generating, by a data processing system, data representing a synthetic genetic sequence configured for labeling at least one cell type by causing expression of a marker in the at least one cell type. The method can include: receiving training data associating at least one feature of a genetic sequence of the at least one cell type with expression of a hallmark of the at least one cell type: training, based on the training data, a model configured to generate data representing a synthetic genetic sequence; receiving input data comprising the at least one feature, and generating the synthetic genetic sequence in response to receiving the input data comprising the at least one feature. The model can include a generative adversarial network (GAN). The GAN can be a deep convolutional GAN (DCGAN). The GAN can include: a generator network configured to receive latent random noise data as the input data and generate the synthetic genetic sequence; and a discriminator network configured to generate a probability value representing whether the input sequence is drawn from the synthetic genetic sequence from the generator network or from a distribution of natural genetic sequences. The method can include training the generator network and the discriminator network of the GAN by alternating the input data between synthetic sequence derived from the latent noise data input to the generator network and natural genetic sequence data. The method can include: receiving input data representing endogenous genomic sequences underlying previously profiled open chromatin regions of at least two cell types; and updating the discriminator network for distinguishing between the at least two cell types. The at least two cell types can include parvalbumin positive (PV+) and parvalbumin negative (PV−) neurons, where the discriminator network is configured to distinguish between the PV+ and PV-neurons based on the input data. The method can include optimizing a feature of the synthetic genetic sequence by applying a class label to both the generator network and the discriminator network. The class label can be configured to force a first probability value for a first input type and a second probability value for a second input type that is different from the first input type. The feature can represent an enhancer of an activity in a cell type. The method can further include generating a nucleic acid sequence comprising the synthetic genetic sequence. The nucleic acid sequence can include the synthetic genetic sequence operably linked to a nucleotide sequence encoding a marker (e.g., a tagged Sun1 fusion polypeptide). The nucleic acid sequence can further include a virus nucleic acid sequence (e.g., an AAV or lentivirus sequence). The method can include: receiving results data representing a delivery of a nucleic acid including the synthetic genetic sequence to an organism, the results data representing a successful labeling of the at least one cell type or an unsuccessful labeling of the at least one cell type; updating the model using the results data; and generating an updated synthetic genetic sequence based on the updated model. The method can further include: receiving training data including the hallmark representing marker positive results marker negative results, or both, extracting at least one feature corresponding to the marker positive result or to the marker negative result; and adding the at least one feature to the model. The at least one feature can be a set of k-mer or gapped k-mer counts, and wherein extracting the at least one feature comprises scanning the sequence to determine the set of k-mer counts that form the sequence. The model can include a support vector machine that includes: a feature space; and a support vector representing a classification border in the feature space, where the method includes adding, to the support vector of the support vector machine, a given set of k-mer counts within a predefined distance of the classification border in the feature space of the support vector machine. The model can include a neural network. The neural network can be a convolutional neural network. The neural network can include one or more weight values each associated with a feature of the synthetic genetic sequence. The feature can include a set of k-mer counts of the genetic sequence. The feature can represent a transcription factor binding motif. The synthetic genetic sequence can be configured to distinguish between parvalbumin positive (PV+) and parvalbumin negative (PV−) neurons: PV+ and excitatory (EXC) neurons; or PV+ and vasoactive intestinal peptide-expressing (VIP+) neurons.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A is a schematic of the Cre-dependent mechanism of the cSNAIL viral probe. The Sun1GFP coding sequence between the LoxP sites is expressed in the presence of Cre (left), but not in the absence of Cre (right). FIGS. 1B and 1C are images of brain tissue (M1 region) from a PVcre/ai14 mouse injected with the cSNAIL Sun1GFP virus. Viral labeling was indicated by green fluorescent protein (GFP), in direct comparison with transgenically labeled Cre+ (PV+) cells (originally in red). FIG. 1D is an image showing nuclei in suspension after brain tissue homogenization. Nuclei were stained blue with 4',6-diamidino-2-phenylindole (DAPI) stain, and virally tagged PV+ nuclei were co-labeled with GFP. The GFP+ cells adhered to magnetic beads (straight arrow), while GFP− cells did not (curved arrows), allowing for separation of the two groups.

FIG. 2A is a flow diagram of a process for generating synthetic enhancers by a machine learning model.

FIG. 4C depicts hypergeometric enrichment significance of the overlap between cell type-specific SNAIL open chromatin regions and cluster-specific snATAC-seq open chromatin regions (data from data.nemoarehive.org/biccn/assay/chromatin/cemba/scell/processed/analysis/EckerRen_Mouse_MOp_methylation_ATAC/).

FIG. 6A is an image showing that SUN1GFP expression from cSNAIL correctly localized to the nuclear envelope in tissue. Specifically, SUN1GFP (yielding green fluorescence) from cSNAIL was expressed in a Cre+ cell in cortical tissue from a Pvalb-2A-Cre/Ai14 mouse that expresses tdTomato as a reporter of Cre (yielding magenta fluorescence). FIG. 6B is an image showing that SUN1GFP expression from cSNAIL was sufficient to bind anti-GFP-coated magnetic beads for affinity purification. FIG. 6C is a series of images showing that SUN1GFP expression from cSNAIL was restricted to Cre+ cells in the cortex, striatum, and GPe. These images show SUN1GFP expression from cSNAIL in a Pvalb-2A-Cre/Ai14 mouse. The tissue slices were also stained for NeuN, a pan-neuronal marker with blue fluorescence. cSNAIL virus specificity and efficiency within each brain region are indicated below the images. Standard errors were calculated across four independent images. The total SUN1GFP+ and/or Cre+ cells in the analysis were cortex N=1088 cells, striatum N=107 cells, and GPe N=773 cells. The expected neuron transduction metrics were reported elsewhere (Chan et al., *Nat. Neurosci.* 20:1172-1179, 2017). ND=no data.

FIG. 7A is a genome browser visualization of ATAC-seq and RNA-seq signal at the Pvalb locus from pooled p-value tracks. cSNAIL data is labeled in black and is compared with publicly available data (Mo et al., *Neuron* 86:1369-1384, 2015) labeled in grey. FIG. 7B shows enrichment of mouse cortical snATAC-seq cluster markers (LFC>0.25 and p<0.05 relative to all other clusters) within cell type-specific ATAC-seq peaks in the data by the hypergeometric test (data and method from Signac vignette, available online at github.com/timoast/signac). FIG. 7C shows expression of cortical cSNAIL PV+ gene signatures per cell of external mouse cortex snRNA-seq (data from portal.nemoarchive.org).

FIGS. 8A-8F show molecular signatures of PV+ neurons across brain regions. FIG. 8A shows the numbers of differentially expressed genes (DESeq2 $p_{adj}$<0.01 and |LFC|>1) between cSNAIL-isolated PV+ and PV− fractions from the cortex, striatum, and GPe of sham animals. FIG. 8B shows normalized read counts from example marker transcripts in each sample. DESeq2 normalized counts were converted to the proportion that they represent of the total read count for that transcript within the given brain region. FIG. 8C shows representative pathway enrichments for pan-PV+ and pan-PV− marker genes by g:Profiler (Peterson et al., *Nucleic Acids Res* 47:W191-W198, 2019). The size of the bubble represents the negative log of the adjusted p-value after multiple hypotheses correction. FIG. 8D shows the numbers of cell type-enriched ATAC-seq peaks ($p_{adj}$<0.01 and |LFC|>1) in PV+ populations from each brain region. FIG. 8E shows DESeq2 normalized counts of ATAC-seq reads within 5 kb of the transcription start site of marker genes. Again, counts were normalized to the total counts for that transcript in the cortex, striatum, or GPe. FIG. 8F shows examples of motifs enriched in PV+ specific or PV-specific ATAC-seq peaks relative to all peaks in that cell type by AME (McLeay and Bailey, *BMC Bioinformatics* 11:165, 2010). Each brain region was assessed separately, and these motifs were significantly enriched in PV+ or PV− sequences across all brain regions.

FIGS. 9A-9D show that divergent gene expression in dopamine depleted mice is largely restricted to GPc PV+ neurons and implicates the HIF pathway. FIG. 9A is a table showing the numbers of genes that have differential expression with dopamine depletion (DD) in each cell type. FIG. 9B. is a volcano plot of DD-affected genes in GPe PV+ neurons. Genes meeting the significance threshold of $p_{adj}<0.05$ (above the dotted line) are listed in order of significance. FIG. 9C shows that DD is associated with a specific increase in Hif2a (Epas1) transcription and its target genes in GPe PV+ neurons. The animals are referred to as S1 and S2 for sham animals and DD1-4 for 6-OHDA treated animals in order of depletion severity. FIG. 9D is a graph plotting the proportion of GPe PV+ cells that express Hif2a protein, demonstrating that there was a significant increase between the images from healthy tissue and DD tissue (t-test).

FIG. 10A is a table showing the numbers of ATAC-seq regions in each cell type that were differentially open in DD animals compared to sham animals in a categorical analysis. FIG. 10B shows HIF family transcription factor binding motifs as defined in JASPAR 2018 (Khan et al., *Nucleic Acids Res* 46:260-266, 2018). FIG. 10C is a series of graphs plotting cell type-specific HIF family motif enrichments among sets of sequences underlying ATAC-seq peak summits that increase in accessibility in DD animals.

FIG. 11A is a graph plotting the levels of striatal tyrosine hydroxylase for each hemisphere of four 6-OHDA lesioned animals and two sham animals. The p-values reflect a significant difference in populations by the standard t-test. FIG. 11B includes examples of the quantified images, indicated by the arrows in FIG. 11A.

FIGS. 12A-12D show that the ATAC-seq data was high quality. FIGS. 12A and 12B show that ATAC-seq samples tended to cluster with other samples of the same tissue and cell type by principal component analysis and hierarchical clustering of genome-wide open chromatin profiling. FIG. 12C is a graph demonstrating that the data exhibited the characteristic periodicity in fragment length distributions of high quality ATAC-seq data, reflecting nucleosome positioning. The plot shown is a representative example from one GPe PV+ sample. FIG. 12D shows that the ATAC-seq signal was enriched at the transcription start sites (TSS), indicative of high signal-to-noise. The displayed data are a representative example from one GPe PV+ sample.

FIGS. 13A and 13B show additional properties of the mouse cortex snRNA-seq data. FIG. 13A shows cluster annotations per cell of the snRNA-seq data with UMAP embedding. FIG. 13B shows that Pvalb gene expression is highest within the Pvalb interneuron cluster (circled).

FIG. 15A is a graph showing that the first two principal components separated samples by brain region and cell type. FIG. 15B shows that in hierarchical clustering, samples mainly clustered by brain region and then cell type.

DETAILED DESCRIPTION

Figure 1A:
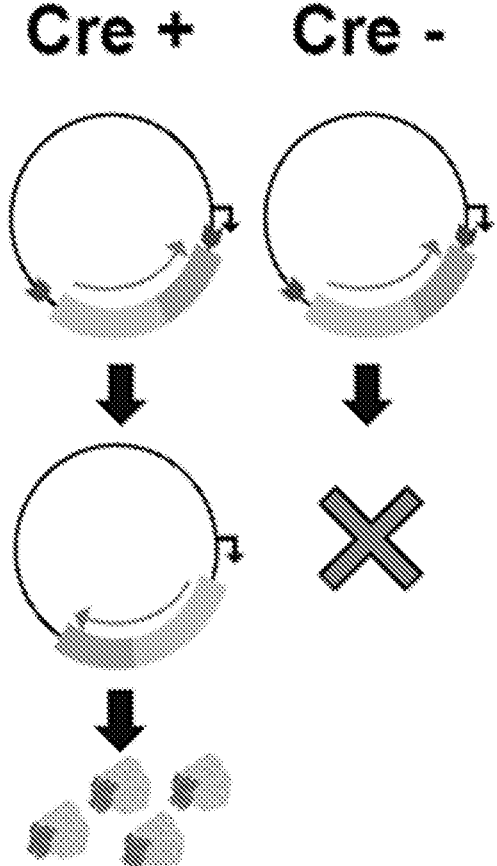
FIGS. 1A-1D demonstrate validation of the cSNAIL probe system in a non-limiting example of a neuron subtype in mice, with imaging and molecular data.

Genomic assays of specific cell types first require identifying and separating the cells of interest from the rest of the tissue. In brain tissue, for example, this can be especially difficult due to the high diversity of cell types that are tightly packed together and connected with long, fragile projections. In the adult brain, it is impractical to separate whole cells in sufficient quantities because these projections can break off, spilling their contents into the media. Instead, researchers have turned to sorting the nuclei of cell types of interest. One method for isolation of nuclei without using fixatives (which are incompatible with some genomic assays) is the INTACT method (Mo et al., supra), which requires a double transgenic mouse. The first transgene expresses Cre recombinase in a cell type-specific manner, and the second expresses the Sun1GFP fusion protein only in the presence of Cre recombinase. An INTACT mouse therefore expresses Sun1GFP exclusively in the cells of interest.

Sun1 is a mammalian nuclear envelope protein that can serve as a robust tool for cell labeling and isolation from homogenized tissues, due to its localization. The Sun1 coding sequence can be fused with sequences encoding two copies of super-folder GFP, which reliably folds into the correct conformation even in protein fusions. The result of Sun1GFP expression is GFP that is tightly anchored to the nuclear envelope. Tissue (e.g., brain tissue) from transgenic mice expressing Sun1GFP in one or more particular cell types (e.g., particular neuron types) can be homogenized into a suspension of single nuclei, and GFP+ nuclei can be separated from GFP− nuclei using affinity purification in which magnetic beads coated with an anti-GFP antibody bind GFP+ nuclei, but not GFP-nuclei. The beads with GFP+ nuclei can then be pulled away from the GFP− nuclei with a magnet and used for further studies.

The INTACT method has been instrumental for studying specific subsets of neurons in isolation. Its reliance on double transgenic mice has limited its use, however, because transgenic breeding can be highly variable and resource-intensive, and because transgenic strains are often only feasible for cell types that can be characterized by a single marker locus, leaving many populations inaccessible. The current technology is limited mainly to the laboratory *Mus musculus* species, and the difficult nature of creating new transgenic organisms means that it is impractical to extend the framework to non-model organisms. In addition, multiple transgenic breeding makes it problematic to use cell type-specific mouse lines in conjunction with other transgenic traits, including disease models or strains that label an additional cell population of interest.

As described herein, viral delivery of cell type-specific labels can provide much more flexibility across cell types and species, as compared to transgene expression. In general, the SNAIL and cSNAIL materials and methods provided herein utilize an affinity purification strategy that is similar to the INTACT method for immunopurification of nuclei, but without the need for double transgenic animals. In some cases, instead of transgenesis, viruses can be used to deliver a simple, compact labeling gene that is sufficient to achieve success. When this non-limiting embodiment is paired with a virus [e.g., Adeno-associated virus (AAV) or lentivirus] delivery method, the probes can be introduced into any appropriate mammals (e.g., mice, rats, sheep, pigs, dogs, or non-human primates) through intravenous injection, direct injection into the brain, or any other appropriate method. This delivery procedure is a much more time and resource-efficient way to tag cell populations when compared with the intricacies of transgenic breeding. The method also drastically minimizes the number of collateral animals that are bred for an experiment but cannot be used due to undesirable genotypes.

The probes provided herein include, for example, Cre-dependent (cSNAIL) viral probes that are immediately compatible with existing strains of Cre transgenic mice, as well as Cre-independent (SNAIL) viral probes, which are developed individually for different cell types and, as described more fully below, accomplish complete independence from animal strain. Both probe types contain a newly designed sequence that includes an N-truncated exon-only version of the Sun1GFP fusion protein. This sequence is $1/16^{th}$ the size of the INTACT sequence (2,367 bp), and was sufficient to achieve successful nuclear envelope GFP labeling for affinity purification even in vivo (e.g., in the brain), which was rather surprising. The smaller size enables much more flexibility in gene delivery, including compatibility with AAV virus.

The cell type specificity of the cSNAIL viral probe is conferred through its dependence on DNA rearrangement by Cre recombinase (FIG. 1A), which is only present in certain cells. Specifically, a double-floxed inverted orientation (DIO) system (Atasoy et al., *J. Neurosci.* 28:7025-7030, 2008) is used, in which the Sun1GFP sequence is delivered in the reverse orientation, such that it cannot be transcribed. When the DNA encounters Cre recombinase protein, Cre can excise the Sun1GFP sequence and irreversibly re-insert it in the correct orientation for expression. This system is more tightly regulated than the lox-flanked stop codon system that is used to confer Cre dependence in the INTACT transgenic mouse strain (Atasoy et al., supra).

For SNAIL viral probes, a cell type-specific regulatory element is required to drive targeted gene expression in the desired cell type of interest. As described in the Examples below, a regulatory element was designed to label one specific cell type—parvalbumin positive (PV+) inhibitory interneurons—using in silico screening. Profiles of cell type-specific open chromatin were used for this neuron subtype to train machine learning models that link genome sequence to parvalbumin-specific regulatory activity. In particular, three gapped k-mer support vector machines were built to discriminate between the comparative regulatory sequence activity in PV+ vs. PV− neurons, PV+ vs. excitatory neurons, and PV+ vs. vasoactive intestinal peptide-expressing (VIP+) neurons. In addition to gapped k-mer support vector machines, another example embodiment trained similar convolutional neural networks (CNNs), which are the state-of-the-art model for relating raw genomic sequence to regulatory function. All of these models were used to screen PV+ neuron-specific regions of open chromatin for their ability to independently drive cell type-specific gene expression. A top candidate was chosen based on the predicted cell type-specificity, its length, and its proximity to cell type-specific genes. That candidate regulatory sequence was cloned into a plasmid vector in which it could drive the expression of Sun1GFP, and the vector was transduced into the mouse brain using AAV-PHP.eB (Chan et al., *Nat. Neurosci.* 20:1172-1179, 2017).

This document provides nucleic acid constructs that contain sequences encoding fusion polypeptides that include a Sun1 portion and a tag portion. The Sun1 portion enables the fusion polypeptide to localize to the nuclear membrane, while the tag portion enables cells and/or nuclei containing the expressed fusion polypeptide to be identified and isolated away from cells and/or nuclei that do not express the fusion polypeptide. The nucleic acids provided herein can further include other sequences, such as sequences to control expression of the fusion polypeptide (e.g., sequences to promote expression in particular types of cells, and/or sequences to prevent expression unless Cre is present).

The terms "nucleic acid" and "polynucleotide" can be used interchangeably, and refer to both RNA and DNA, including cDNA, genomic DNA, synthetic (e.g., chemically synthesized) DNA, and DNA (or RNA) containing nucleic acid analogs. Polynucleotides can have any three-dimensional structure. A nucleic acid can be double-stranded or single-stranded (i.e., a sense strand or an antisense single strand). Non-limiting examples of polynucleotides include genes, gene fragments, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs.

As used herein, "isolated," when in reference to a nucleic acid, refers to a nucleic acid that is separated from other nucleic acids that are present in a genome, including nucleic acids that normally flank one or both sides of the nucleic acid in the genome. The term "isolated" as used herein with respect to nucleic acids also includes any non-naturally-occurring sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences, as well as DNA that is incorporated into a vector, an autonomously replicating plasmid, a virus (e.g., a pararetrovirus, a retrovirus, lentivirus, adenovirus, or herpes virus), or the genomic DNA of a prokaryote or eukaryote. In addition, an isolated nucleic acid can include a recombinant nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

A nucleic acid can be made by, for example, chemical synthesis or polymerase chain reaction (PCR). PCR refers to a procedure or technique in which target nucleic acids are amplified. PCR can be used to amplify specific sequences from DNA as well as RNA, including sequences from total genomic DNA or total cellular RNA. Various PCR methods are described, for example, in *PCR Primer: A Laboratory Manual*, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid.

Isolated nucleic acids also can be obtained by mutagenesis. For example, a naturally occurring nucleic acid sequence can be mutated using standard techniques, including oligonucleotide-directed mutagenesis and site-directed mutagenesis through PCR. See, *Short Protocols in Molecular Biology*, Chapter 8, Green Publishing Associates and John Wiley & Sons, edited by Ausubel et al., 1992.

Recombinant nucleic acid constructs (e.g., vectors) containing sequences encoding the tagged Sun1 fusion polypeptides also are provided herein. A "vector" is a replicon, such as a plasmid, phage, or cosmid, into which another DNA segment may be inserted so as to bring about the replication of the inserted segment. Vector backbones include, for example, plasmids, viruses, artificial chromosomes, bacterial artificial chromosomes (BACs), yeast artificial chromosomes (YACs), and phage artificial chromosomes (PACs), as well as RNA vectors, and linear or circular DNA or RNA molecules that include chromosomal, non-chromosomal, semi-synthetic, or synthetic nucleic acids. Vectors include those capable of autonomous replication (episomal vectors) and/or expression of nucleic acids to which they are linked (expression vectors). Generally, a vector is capable of replication when associated with the proper control elements. The term "vector" includes cloning and expression vectors, as well as viral vectors and integrating vectors. An "expression vector" is a vector that includes one or more expression control sequences to control and regulate the transcription and/or translation of another DNA sequence. Suitable expression vectors include, without limitation, plasmids and viral vectors derived from, for example, bacteriophage, baculoviruses, tobacco mosaic virus, herpes viruses, cytomegalovirus, retroviruses, vaccinia viruses, adenoviruses, and adeno-associated viruses. Numerous vectors and expression systems are commercially available.

Viral vectors include, without limitation, retrovirus, adenovirus, parvovirus (e.g., adeno associated viruses), coronavirus, negative strand RNA viruses such as orthomyxovirus (e.g., influenza virus), rhabdovirus (e.g., rabies and vesicular stomatitis virus), paramyxovirus (e.g., measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, "Retroviridae: The viruses and their replication," in *Fundamental Virology*, Third Edition, B. N. Fields, et al., eds., Lippincott-Raven Publishers, Philadelphia, 1996).

The terms "regulatory region," "control element," and "expression control sequence" refer to nucleotide sequences that influence transcription or translation initiation and rate, and stability and/or mobility of the transcript or polypeptide product. Regulatory regions include, without limitation, promoter sequences, enhancer sequences, response elements, protein recognition sites, inducible elements, promoter control elements, protein binding sequences, 5' and 3' untranslated regions (UTRs), transcriptional start sites, termination sequences, polyadenylation sequences, introns, and other regulatory regions that can reside within coding sequences, such as secretory signals, Nuclear Localization Sequences (NLS) and protease cleavage sites.

As used herein, "operably linked" means incorporated into a genetic construct so that expression control sequences effectively control expression of a coding sequence of interest. A coding sequence is "operably linked" and "under the control" of expression control sequences in a cell when RNA polymerase is able to transcribe the coding sequence into RNA, which if an mRNA, then can be translated into the protein encoded by the coding sequence. Thus, a regulatory region can modulate, e.g., regulate, facilitate or drive, transcription in the plant cell, plant, or plant tissue in which it is desired to express a modified target nucleic acid.

A promoter is an expression control sequence composed of a region of a DNA molecule, typically (but not always) within 100 nucleotides upstream of the point at which transcription starts (generally near the initiation site for RNA polymerase II). Promoters are involved in recognition and binding of RNA polymerase and other proteins to initiate and modulate transcription. To bring a coding sequence under the control of a promoter, it typically is necessary to position the translation initiation site of the translational reading frame of the polypeptide between one and about fifty nucleotides downstream of the promoter. A promoter can, however, be positioned as much as about 5,000 nucleotides upstream of the translation start site, or about 2,000 nucleotides upstream of the transcription start site. A promoter typically includes at least a core (basal) promoter. A promoter also may include at least one control element such as an upstream element. Such elements include upstream activation regions (UARs) and, optionally, other DNA sequences that affect transcription of a polynucleotide such as a synthetic upstream element.

The choice of promoters to be included depends upon several factors, including, but not limited to, efficiency, selectability, inducibility, desired expression level, and cell or tissue specificity. For example, tissue-, organ- and cell-specific promoters that confer transcription only or predominantly in a particular tissue, organ, and cell type, respectively, can be used. In some cases, a promoter that is active in a particular type of cell (e.g., a particular type of neuron) can be used. Such promoters—or other expression control sequences—can be identified using methods such as those described herein, and can be used in the SNAIL constructs provided herein. Alternatively, constitutive promoters can promote transcription of an operably linked nucleic acid in essentially any tissue of an organism. Such promoters can be used in the cSNAIL constructs provided herein. Other classes of promoters include, without limitation, inducible promoters that confer transcription in response to external stimuli such as chemical agents, developmental stimuli, or environmental stimuli.

A 5' untranslated region (UTR) is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA message stability or translation attenuation. Examples of 3' UTRs include, but are not limited to, polyadenylation signals and transcription termination sequences. A polyadenylation region at the 3'-end of a coding region can also be operably linked to a coding sequence.

Recombinant nucleic acid constructs can include a polynucleotide sequence inserted into a vector suitable for transformation of cells (e.g., plant cells or animal cells). Recombinant vectors can be made using, for example, standard recombinant DNA techniques (see, e.g., Sambrook et al. (1989) *Molecular Cloning: A Laboratory Manual,* 2nd ed., Cold Spring Harbor Laboratory, Cold Spring Harbor, NY). In some cases, a recombinant nucleic acid sequence as described herein can integrate into the genome of a cell via illegitimate (i.e., random, non-homologous, non site-specific) recombination, or a recombinant nucleic acid sequence as described herein can be adapted to integrate into the genome of a cell via homologous recombination. Nucleic acid sequences adapted for integration via homologous recombination are flanked on both sides with sequences that are similar or identical to endogenous target nucleotide sequences, which facilitates integration of the recombinant nucleic acid at the particular site(s) in the genome containing the endogenous target nucleotide sequences. Nucleic acid sequences adapted for integration via homologous recombination also can include a recognition site for a sequence-specific nuclease. Alternatively, the recognition site for a sequence-specific nuclease can be located in the genome of the cell to be transformed.

The nucleic acid constructs described herein typically contain a sequence encoding a tagged Sun1 fusion polypeptide. The term "polypeptide" as used herein refers to a compound of two or more subunit amino acids, regardless of post-translational modification (e.g., phosphorylation or glycosylation). The subunits may be linked by peptide bonds or other bonds such as, for example, ester or ether bonds. The term "amino acid" refers to either natural and/or unnatural or synthetic amino acids, including D/L optical isomers.

By "isolated" or "purified" with respect to a polypeptide it is meant that the polypeptide is separated to some extent from cellular components with which it is normally found in nature (e.g., other polypeptides, lipids, carbohydrates, and nucleic acids). An purified polypeptide can yield a single major band on a non-reducing polyacrylamide gel. A purified polypeptide can be at least about 75% pure (e.g., at least 80%, 85%, 90%, 95%, 97%, 98%, 99%, or 100% pure). Purified polypeptides can be obtained by, for example, extraction from a natural source, by chemical synthesis, or by recombinant production in a host cell or transgenic plant, and can be purified using, for example, affinity chromatography, immunoprecipitation, size exclusion chromatography, and ion exchange chromatography. The extent of purification can be measured using any appropriate method, including, without limitation, column chromatography, polyacrylamide gel electrophoresis, or high-performance liquid chromatography.

The Sun1 portion of the fusion polypeptides provided herein (and encoded by the nucleic acids provided here) can include a fragment of a mouse Sun1 protein. A representative Sun1 protein sequence is provided in SEQ ID NO:1:

*Mus musculus* Sun1 (NCBI Ref. NM_001256118.1)

(SEQ ID NO: 1)

```
MDFSRLHTYTPPQCVPENTGYTYALSSSYSSDALDFETEHKIEPVFDSPR

MSRRSLRLVTTASYSSGDSQAIDSHISTSRATPAKGRETRTVIKQRRSAS

KPAFSINHLSGKGLSSSTSHDSSCSLRSATVLRHPVLDESLIREQTKVDH

FWGLDDDGDLKGGNKAATQGNGELAAEVASSNGYTCRDCRMLSARTDALT

AHSAIHGTTSRVYSRDRTLKPRKAASGTFWWLGSGWYQFVTLISWLNVFL

LTRCLRNICKVFVLLLPLLLLLGAGVSLWGQGNFFSLLPVLNWTAMQPTQ

RVDDSKGMHRPGPLPPSPPPKVDHKASQWPQESDMGQKVASLSAQCHNHD

ERLAELTVLLQKLQIRVDQVDDGREGLSLWVKNVVGQHLQEMGTIEPPDA

KTDFMTFHHDHEVRLSNLEDVLRKLTEKSEAIQKELEETKLKAGSRDEEQ

PLLDRVQHLELELNLLKSQLSDWQHLKTSCEQAGARIQETVQLMFSEDQQ

GGSLEWLLEKLSSRFVSKDELQVLLHDLELKLLQNITHHITVTGQAPTSE

AIVSAVNQAGISGITEAQAHIIVNNALKLYSQDKTGMVDFALESGGGSIL

STRCSETYETKTALLSLFGVPLWYFSQSPRVVIQPDIYPGNCWAFKGSQG

YLVVRLSMKIYPTTFTMEHIPKTLSPTGNISSAPKDFAVYGLETEYQEEG

QPLGRFTYDQEGDSLQMFHTLERPDQAFQIVELRVLSNWGHPEYTCLYRF

RVHGEPIQ
```

The Sun1 fragment included in a fusion polypeptide as provided herein can have a length between about 20 amino acids and about 750 amino acids (e.g., about 20 to 50 amino acids, about 50 to about 100 amino acids, about 100 to about 200 amino acids, about 200 to about 400 amino acids, about 400 to about 600 amino acids, or about 600 to about 750 amino acids). In some cases, for example, the Sun1 portion of a tagged Sun1 fusion polypeptide can include about 400 to about 600 consecutive amino acids from SEQ ID NO:1. In some cases, the Sun1 portion of the tagged Sun1 fusion polypeptide can have at least 90% sequence identity (e.g., at least 92%, 93%, 95%, 97%, 98%, or 99% sequence identity) to a fragment of SEQ ID NO:1 that is about 20 to about 800 amino acids in length (e.g., about 20 to 50, about 50 to about 100, about 100 to about 200, about 200 to about 400, about 400 to about 600, or about 600 to about 750 amino acids in length). In some cases, as described in the Examples, a Sun1 fragment can include amino acids 208 to 757 of SEQ ID NO:1, or can have a sequence that is at least 90% (e.g., at least 92%, 93%, 95%, 97%, 98%, or 99%) identical to amino acids 208 to 757 of SEQ ID NO:1. In some cases, a Sun1 fragment can include a portion of the fragment containing amino acids 208 to 757 of SEQ ID NO:1 (e.g., a portion that is 20 to 50, 50 to 100, 100 to 300, or 300 to 500 amino acids in length), or a Sun1 fragment can have a sequence that is at least 90% (e.g., at least 92%, 93%, 95%, 97%, 98%, or 99%) identical to a portion of the fragment containing amino acids 208 to 757 of SEQ ID NO:1.

The percent sequence identity between a particular amino acid sequence and a sequence referenced by a particular sequence identification number is determined as follows. First, an amino acid sequence is compared to the sequence set forth in a particular query sequence using the BLAST 2 Sequences (B12seq) program from the stand-alone version of BLASTZ containing BLASTP version 2.0.14. This stand-alone version of BLASTZ can be obtained online at fr.com/blast or at ncbi.nlm.nih.gov. Instructions explaining how to use the B12seq program can be found in the readme file accompanying BLASTZ. B12seq performs a comparison between two sequences using the BLASTN or BLASTP algorithm. BLASTN is used to compare nucleic acid sequences, while BLASTP is used to compare amino acid sequences. To compare two To compare two amino acid sequences, the options of B12seq are set as follows: -i is set to a file containing the first amino acid sequence to be compared (e.g., C:\seq1.txt): -j is set to a file containing the second amino acid sequence to be compared (e.g., C:\seq2.txt): -p is set to blastp; -o is set to any desired file name (e.g., C:\output.txt): and all other options are left at their default setting. For example, the following command can be used to generate an output file containing a comparison between two amino acid sequences: C:\B12seq -i c:\seq1.txt -j c:\seq2.txt -p blastp -o c:\output.txt. If the two compared sequences sham homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence or by an articulated length (e.g., 100 consecutive amino acid residues from a sequence set forth in an identified sequence), followed by multiplying the resulting value by 100. For example, the reference mouse Sun1 amino acid sequence set forth in SEQ ID NO:1 is 757 residues in length. An amino acid sequence that has 740 matches when aligned with the reference sequence is 97.8 percent identical to the reference sequence (i.e., 740/757×100=97.8). It is noted that the percent sequence identity value is rounded to the nearest tenth. For example, 75.11, 75.12, 75.13, and 75.14 are rounded down to 75.1, while 75.15, 75.16, 7.17, 75.18, and 7.19 are rounded up to 7.2. It also is noted that the length value will always be an integer.

In addition to the Sun1 portion, the fusion polypeptides provided herein can include a tag sequence designed to facilitate manipulation or detection (e.g., localization, purification, and/or isolation) of the expressed polypeptide. Any suitable tag can be included. In some cases, a fluorescent tag can be used (e.g., GFP, yellow fluorescent protein, or mCherry). A representative amino acid sequence for a superfolder GFP is provided in SEQ ID NO:2:

```
                                        (SEQ ID NO: 2)
MSKGEELFTGVVPILVELDGDVNGHKFSVRGEGEGDATNGKLTLKFICTT

GKLPVPWPTLVTTLTYGVQCFSRYPDHMKRHDFFKSAMPEGYVQERTISF

KDDGTYKTRAEVKFEGDTLVNRIELKGIDFKEDGNILGHKLEYNFNSHNV

YITADKQKNGIKANFKIRHNVEDGSVQLADHYQQNTPIGDGPVLLPDNHY

LSTQSVLSKDPNEKRDHMVLLEFVTAAGITHGMDELYK
```

In some cases, a tagged Sun1 fusion polypeptide can include an amino acid sequence that is at least 90% (e.g., at least 92%, 93%, 95%, 97%, 98%, or 99%) identical to the sequence set forth in SEQ ID NO:2. Other suitable tags that can be included in the fusion polypeptides provided herein include, without limitation, glutathione S-transferase (GST), polyhistidine, c-myc, hemagglutinin, or Flag™ tag (Kodak, New Haven, CT). The tag sequence can be located within the Sun1 portion of the fusion polypeptide, or can be at or adjacent to the carboxyl or amino terminus of the Sun1 portion of the fusion polypeptide.

Figure 5A:
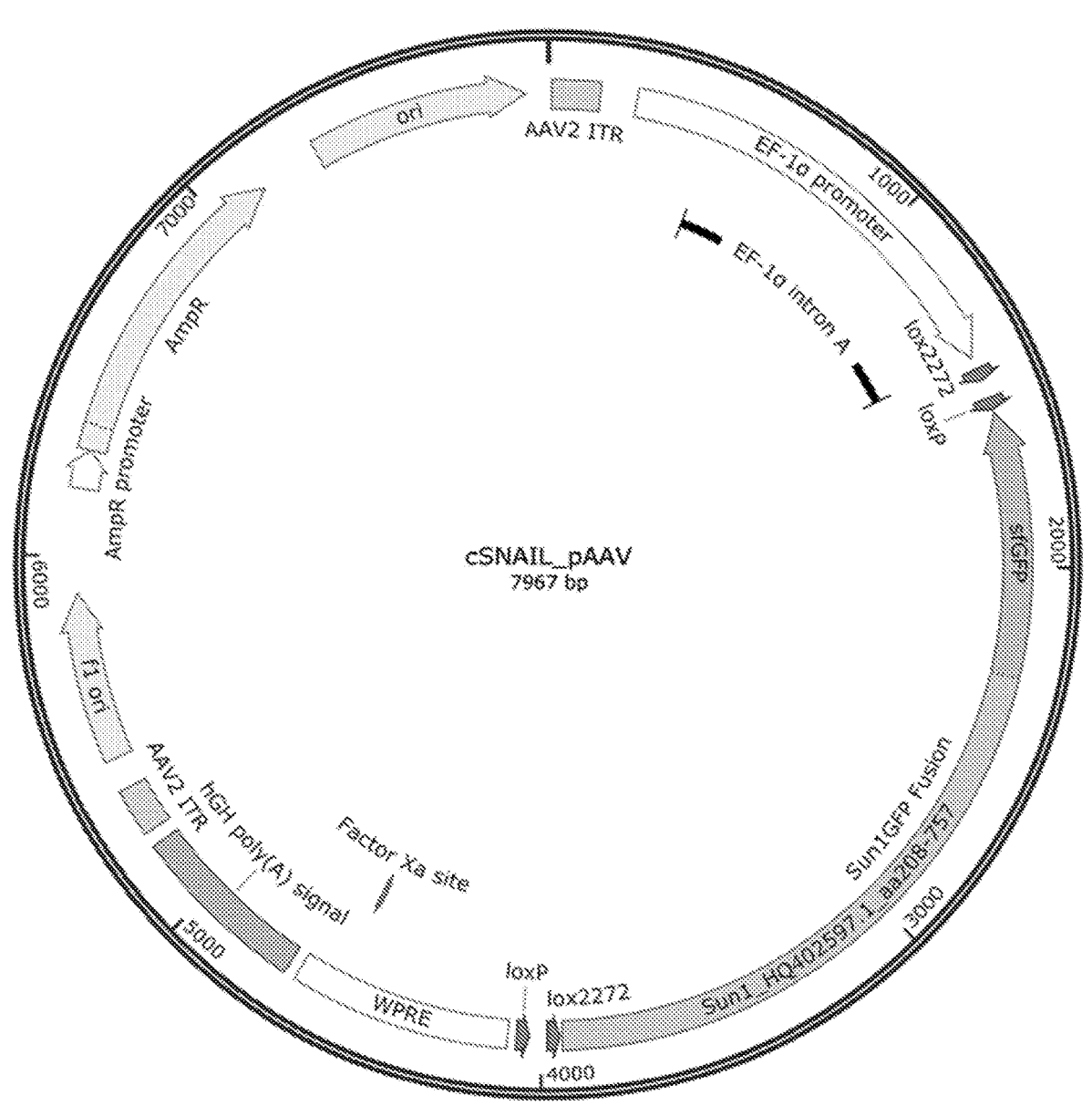
FIG. 5A is a schematic depicting the structure of the pAAV-Ef1a-DIO-SUN1GFP-WPRE-pA construct.

In addition to the sequence encoding the tagged Sun1 fusion polypeptide, the cSNAIL constructs provided herein can include a promoter sequence (e.g., a constitutive promoter, an organ specific promoter, or a promoter that is activated by neural activity or a particular disease state such as oxidative stress or cancer, such as an IEG-sensitive promoter as disclosed by Sorensen et al., *eLife* 5:e13918, 2016) and loxP sites flanking either side of the sequence encoding the fusion polypeptide, such that one of the loxP sites separates the sequence encoding the fusion polypeptide from the promoter. As depicted in FIGS. 1A and 5A, for example, the sequence encoding the tagged Sun1 fusion polypeptide can be inverted between the loxP sequences, such that the fusion polypeptide is not expressed until after the coding sequence is excised by a Cre recombinase and reinserted in the "correct" orientation.

Figure 5B:
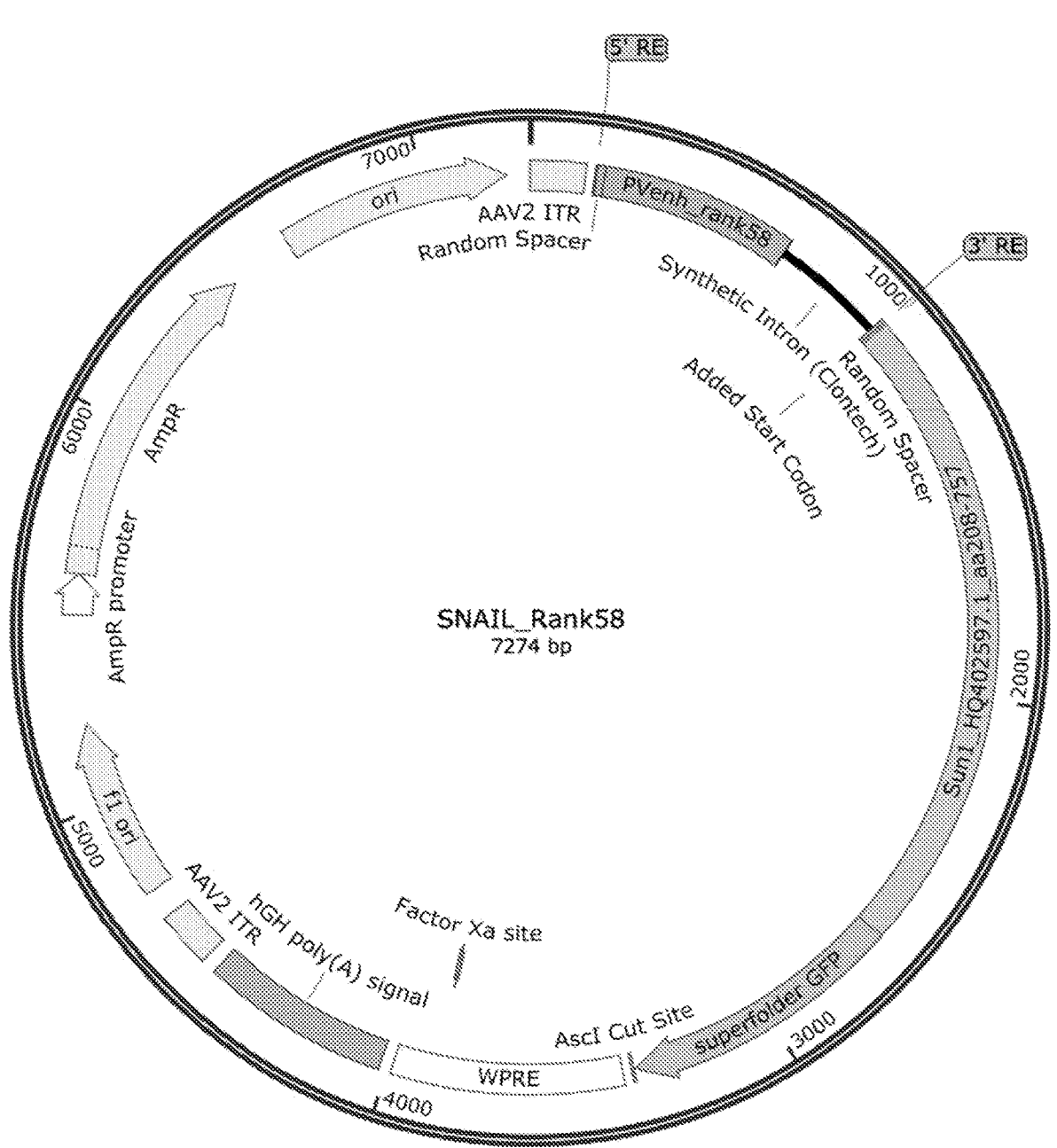
FIGS. 5B and 5C depict the structures of two PV SNAIL pAAV constructs.
Figure 5C:
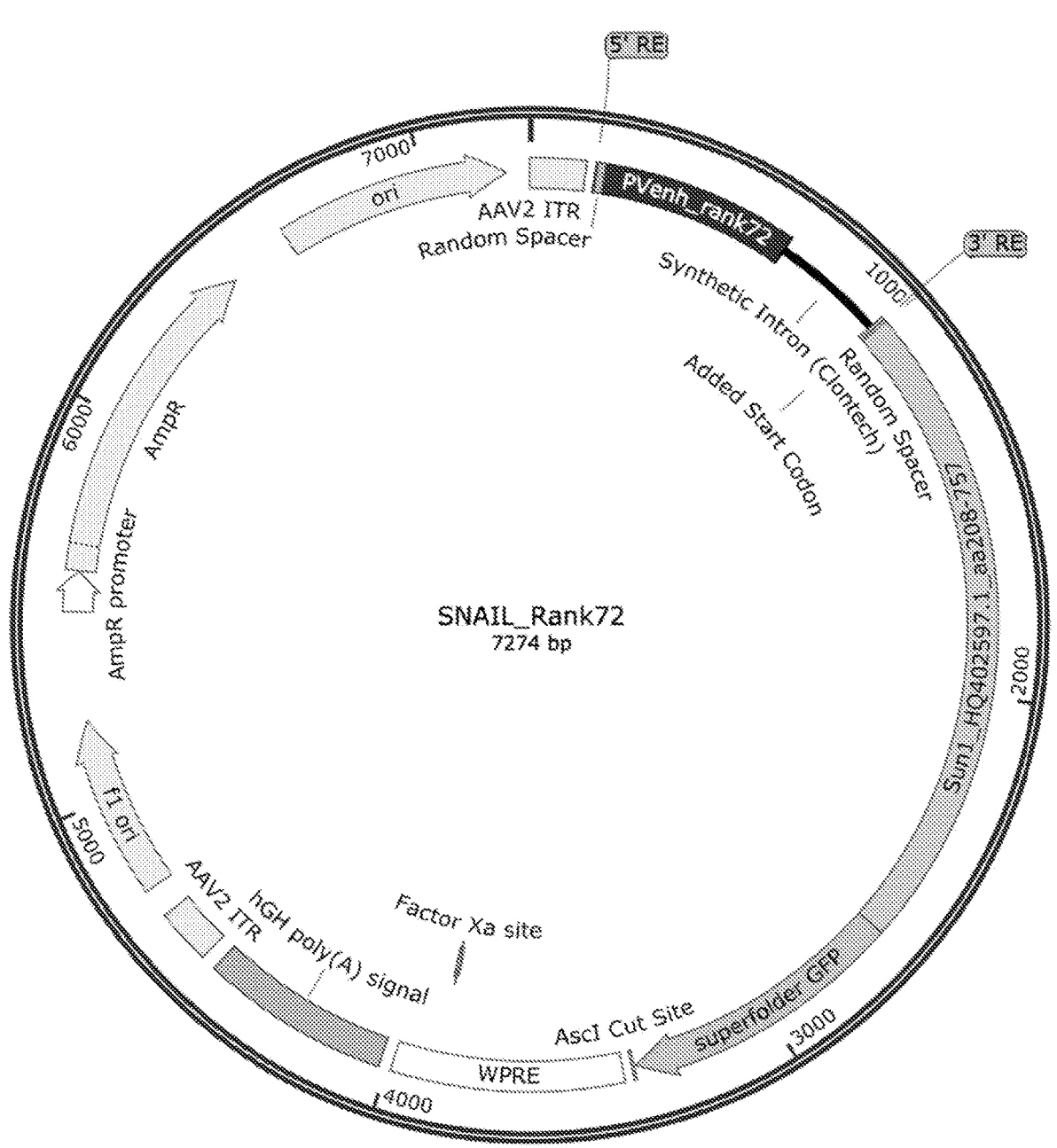

The SNAIL constructs provided herein (see, e.g., FIGS. 5B and 5C) lack loxP sequences, and contain promoter and/or enhancer sequences that drive expression of the tagged Sun1 fusion polypeptide in a specific cell type, thus allowing for identification and isolation of cells of the specific, selected type. In some applications of SNAIL, synthetic enhancer sequences can be constructed purely through computational optimization, and can be paired with SNAIL to generate more specific and efficient cell type labels than endogenous genomic sequences prioritized using the CNNs and SVMs. In addition to other generative models, deep convolutional generative adversarial networks (DCGANs) that have been applied successfully for deep generative design of realistic faces, objects, and art can be used. Sequence classification tasks share many parallels with image classification. CNNs are the state-of-the-art model for both tasks, and DCGANs, which utilize CNNs under the hood for discrimination, are therefore an ideal choice for generating realistic sequences. Further, conditional DCGANs, which are a variant of GANs, can be utilized to generate sequences on the condition that they confer specific activity in a given cell type of interest versus other surrounding cell types. These can be trained on any neural cell type for which high resolution open chromatin or enhancer activity measurements exist. The generated sequences can then be cloned into the SNAIL vector to screen and generate high quality AAV-delivered cell type labels.

Generally, as previously discussed, machine learning models can be used for generating data representing a synthetic genetic sequence configured for labeling at least one cell type by causing expression of a marker in the at least one cell type. The models can include GANs, such as DCGANs, CNNs, support vector machines (SVMs), and so forth. The machine learning models are configured for generating the synthetic genetic sequences that are candidates for the SNAIL process (e.g., as viral probes).

FIG. 2A shows an example process 250 for training and executing the machine learning model to generate the synthetic genetic sequences. The process 250 includes receiving (252) training data associating at least one feature of a genetic sequence of the at least one cell type with expression of a hallmark of the at least one cell type. The process 250 includes training (254), based on the training data, a model configured to generate data representing a synthetic genetic sequence. The process 250 includes receiving (256) input data including the at least one feature of the genetic sequence. The process 250 includes generating (258) the synthetic genetic sequence in response to receiving the input data comprising the at least one feature.

Figure 2B:
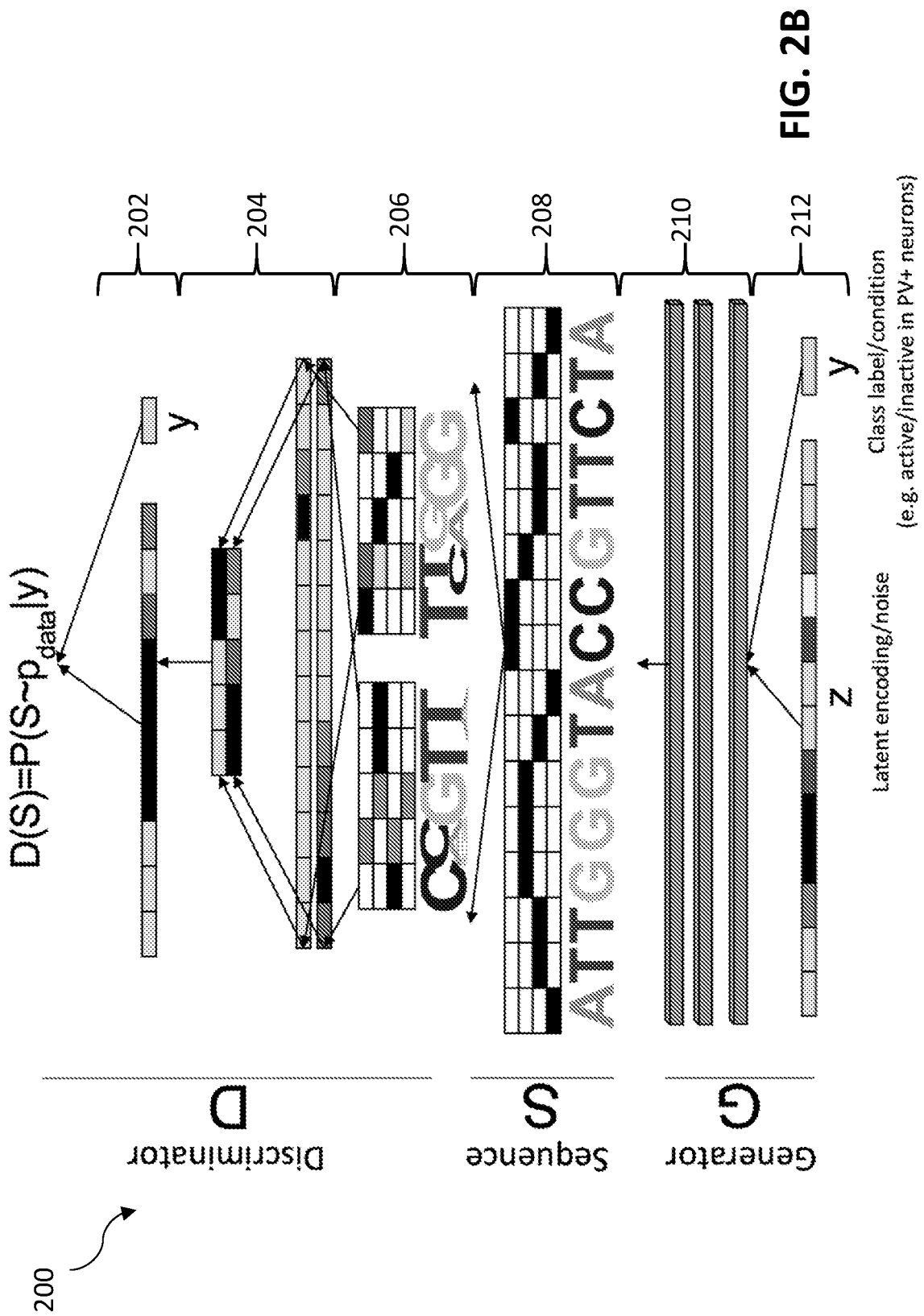
FIG. 2B is a schematic of a conditional generative adversanal network (GAN) for generating synthetic enhancers to label cell types using SNAIL

In some implementations, the machine learning model includes a GAN. The GAN generally includes a generator network configured to receive latent random noise data as the input data and generate the synthetic genetic sequence and a discriminator network configured to generate a probability value representing whether the input sequence is drawn from the synthetic genetic sequence from the generator network or from a distribution of natural genetic sequences. Turning briefly to FIG. 2B, an example machine learning model 200 is shown for generating data representing a synthetic genetic sequence configured for labeling at least one cell type by causing expression of a marker in the at least one cell type.

Generally, the machine learning model 200 is configured to generate data that models the SNAIL constructs (e.g., viral probes) discussed throughout this specification. The model 200 is a particular model including a DCGAN that has a generator G, a sequence S, and a discriminator D. However, as previously described, while the DCGAN is shown for illustrative purposes, other machine learning models are possible, such as support vector machines (SVNs), neural networks (NN) such as CNNs. and so forth. The models for generating regulatory sequences is not specific for SVM and CNNs, but also can utilize generative components to the CNNs that relate genomic sequences to regulatory activity and use them to construct synthetic enhancer sequences. Machine learning models, such as model 200, are configured to construct synthetic enhancer sequences that are computationally optimized to drive cell type-specific labeling when used in an AAV construct, more so than the endogenous genomic sequences that were used to train the CNN classifiers.

Returning to FIG. 2A, in some implementations, the machine learning model is configured for generating a nucleic acid sequence comprising the synthetic genetic sequence. In this example, the nucleic acid sequence comprises the synthetic genetic sequence operably linked to a nucleotide sequence encoding a marker. For example, the marker can include a Sun1GFP fusion polypeptide. In another example, the nucleic acid sequence further comprises a virus nucleic acid sequence. Here, the virus can include an adeno-associated virus (AAV).

The machine learning model is configured for receiving results data representing a delivery of a nucleic acid including the synthetic genetic sequence to an organism. The results data represents a successful labeling of the at least one cell type or an unsuccessful labeling of the at least one cell type. To train the model, the model is updated using the results data. The model is then configured to generate an updated synthetic genetic sequence based on the updated model. Updating the model can also be done by receiving training data including the hallmark representing marker positive results marker negative results, or both. The at least one feature corresponding to the marker positive result or to the marker negative result is extracted. The at least one feature is then added to the model. In some implementations, the feature is a set of k-mer or gapped k-mer counts. Extracting the at least one feature can include scanning the sequence to determine the set of k-mer counts that form the sequence.

Other models besides the GAN of FIG. 2B can be used. For example, a support vector machine includes a feature space a support vector representing a classification border in the feature space. The model is executed to add, to the support vector of the support vector machine, a given set of k-mer counts within a predefined distance of the classification border in the feature space of the support vector machine.

In another example, the machine learning model includes a neural network. For example, the machine learning model can include a convolutional neural network. The neural network is loaded with one or more weight values (also called activation values) each associated with a feature of the synthetic genetic sequence. For example, a feature of the neural network can include a set of k-mer counts of the genetic sequence. In some implementations, the feature represents a transcription factor binding motif.

In any of the machine learning models described in this specification, the synthetic genetic sequence that is generated from the model is configured to distinguish between cell types. The particular cell types are based on the training data used. For example, the genetic sequence that is generated from the model can be configured to distinguish between parvalbumin positive (PV+) and parvalbumin negative (PV−) cells (e.g., the generated sequence can lead to expression in at least 70%, at least 80%, at least 90%, at least 95%, or at least 99% of all PV+ neurons that are transduced by the virus and have the chance to express the machinery, but would not lead to expression in at least 70%, at least 80%, at least 90%, at least 95%, or at least 99% of PV− cells). For example, the genetic sequence that is generated from the model can be configured to distinguish between PV+ and excitatory (EXC) neurons (e.g., the generated sequence can lead to expression in at least 70%, at least 80%, at least 90%, at least 95%, or at least 99% of all PV+ neurons that are transduced by the virus and have the chance to express the machinery, but would not lead to expression in at least 70%, at least 80%, at least 90%, at least 95%, or at least 99% of EXC neurons). For example, the generated genetic sequence that is generated from the model can be configured to distinguish between PV+ and vasoactive intestinal peptide-expressing (VIP+) neurons (e.g., the generated sequence can lead to expression in at least 70%, at least 80%, at least 90%, at least 95%, or at least 99% of all PV+ neurons that are transduced by the virus and have the chance to express the machinery, but would not lead to expression in at least 70%, at least 80%, at least 90%, at least 95%, or at least 99% of VIP+ neurons). However, other cell types can be distinguished by the generated genetic sequence based on the training data used. These examples are non-exhaustive and illustrate possible examples from hundreds or thousands of cell types. The regulatory sequence features learned may extend beyond cell types as well as to cellular states, such as neurons that in the process or responding to neural activity or cells that are responding to DNA damage.

As shown in FIG. 2B, the DCGAN for labeling at least one cell type by causing expression of a marker in the at least one cell type includes two neural network modules, a generator network G and a discriminator network D. The generator G receives latent random noise input (z) and outputs a synthetic sequence. The discriminator network is configured to generate probability value representing a probability that an input sequence is drawn from a distribution of real sequences. The parameters of both G and D can be tuned together using alternating phases of training with real sequences from existing data sources and synthetic sequences generated from G. As the models are trained, G generally generates synthetic sequences that are closer to the real data distribution than before. The discriminator is more likely to classify these generate sequences as genuine.

The generator is training G to generate realistic sequence data. For example, a GAN could be applied to generate synthetic enhancers that are likely highly active in PV+ or PV– neurons by training on real data drawn from endogenous genomic sequences underlying previously profiled open chromatin regions in PV+ and PV– neurons. Further, to optimize specific properties of the sequence, a conditional GAN can be used where an additional class label (y) is input to both G and D. For example, to generate sequences specific to PV+ neurons relative to PV– neurons, a GAN could be trained on real sequences active in both PV+ and PV– neurons, but the generation can be forced to be specific to PV+ neurons by setting y to be 1 for all sequences active in PV+ neurons and 0 for all sequences active in PV– neurons. This enables discriminative generation of sequences, where the optimized property is enhancer activity in a cell type relative to surrounding or background cell types.

Generally, using the GAN includes training the generator network and the discriminator network of the GAN by alternating the input data between synthetic sequence derived from the latent noise data input to the generator network and natural genetic sequence data. The GAN receives input data representing endogenous genomic sequences underlying previously profiled open chromatin regions of at least two cell types and then updates the discriminator network for distinguishing between the at least two cell types. In an example, the at least two cell types include parvalbumin positive (PV+) and parvalbumin negative (PV–) neurons; however, other cell types can be used, and am described throughout this specification. In this example, the discriminator network is configured to distinguish between the PV+ and PV– neurons based on the input data, but other cell types can be used as well, such as excitatory (EXC) neurons, vasoactive intestinal peptide-expressing (VIP+) neurons, and so forth.

The GAN is configured for optimizing a feature of the synthetic genetic sequence by applying a class label to both the generator network and the discriminator network. The class label is configured to force a first probability value for a first input type and a second probability value for a second input type that is different from the first input type. In some implementations, the feature represents an enhancer of an activity in a cell type.

The model 200 is configured to receive (212) the noise and condition input together to generate a compressed representation of the output sequence. The compressed representation is unpacked (210) using a deconvolution process. Fully connected layers can be used in the model 200 to generate a synthetic sequence. The model 200 is configured to generate (208) sequence binary encoding to input to the discriminator. The discriminator is configured to determine whether the sequence it receives is a synthetic sequence or a naturally occurring sequence. The discriminator includes a one dimensional (ID) convolution layer configured to scan (206) the received sequences for patterns. Max pooling can be used (204) to down-sample the input sequence. This convolution and max pooling process can be iterated as needed. The class label (e.g., condition) and compressed output from multiple fully connected layers are output (202) into an output unit.

For SNAIL viral probes, a cell type-specific regulatory element is required to drive targeted gene expression in the desired cell type of interest. In one embodiment, a regulatory element can be configured to label one specific cell type, parvalbumin positive (PV+) inhibitory interneurons. In an experiment, profiles of cell type-specific open chromatin were used for this neuron subtype to train machine learning models that link genome sequence to parvalbumin-specific regulatory activity. Specifically, three gapped k-mer support vector machines were built that discriminate between the comparative regulatory sequence activity in PV+ vs. PV– neurons, PV+ vs. excitatory neurons, and PV+ vs. vasoactive intestinal peptide-expressing (VIP+) neurons. In addition to gapped k-mer support vector machines, another example embodiment trained similar convolutional neural networks (CNNs) which are the state-of-the-art model for relating raw genomic sequence to regulatory function. All of these models were used to screen PV+ neuron-specific regions of open chromatin for their ability to independently drive cell type-specific gene expression. The resulting data 300 are shown in graphs 302, 304, 306, and 308 of FIG. 3 and subsequently described. A top candidate is chosen based on the predicted cell type-specificity, its length, and its proximity to cell type-specific genes. That candidate regulatory sequence was cloned into a plasmid vector in which it drives the expression of Sun1GFP and the vector was transduced into the mouse brain using AAV-PHP.eB.

This document also provides methods for using the constructs described herein to label and isolate nuclei and/or cells of a select type. The methods can include, for example providing a cSNAIL or SNAIL nucleic acid construct as described herein, introducing the construct into a population of different cell types, and culturing or incubating the cells under conditions in which a tagged Sun1 fusion polypeptide encoded by the cSNAIL or SNAIL construct is expressed in the selected cell type (and is not expressed in cells that are not of the selected type), thereby labeling the selected cell type. When a cSNAIL nucleic acid construct is used, the methods also include introducing a nucleic acid construct encoding a Cre recombinase into the population of different cell types, where the sequence encoding the Cre recombinase is operably linked to a promoter that is specific for the selected cell type. In addition, when a cSNAIL construct is used, the conditions under which the cell population is cultured or incubated permit the Cre recombinase to be expressed in the selected cell type, thus leading to excision of the sequence encoding the tagged Sun1 fusion polypeptide from its nucleic acid construct and re-insertion of the tagged Sun1 fusion polypeptide coding sequence in the correct orientation for expression. It is to be noted that in some cases, the population of cells is within a mammal.

Any appropriate method can be used to introduce the SNAIL construct or the cSNAIL and Cre recombinase constructs into a population of cells. As used herein, "transformed" and "transfected" encompass the introduction of one or more nucleic acid molecules (e.g., one or more expression vectors) into a cell by any of a number of techniques. Suitable methods for transforming and transfecting host cells can be found, for example, in Sambrook et al., *Molecular Cloning: A Laboratory Manual* (2nd edition), Cold Spring Harbor Laboratory, New York (1989). For example, calcium phosphate precipitation, electroporation, heat shock, lipofection, microinjection, and virus-mediated nucleic acid transfer can be used introduce nucleic acid molecules into cells. In addition, naked DNA can be delivered directly to cells in vivo (see, e.g., U.S. Pat. Nos. 5,580,859 and 5,589,466). The isolated nucleic acid molecule transformed into a host cell can be integrated into the genome of the cell or maintained in an episomal state. Thus, host cells can be stably or transiently transfected with a construct containing an isolated nucleic acid molecule provided herein. In some cases, one or more nucleic acid constructs can be incorporated into virus particles (e.g., AAV or lentivirus particles), and the virus particles can be delivered to cells in order to transfer their nucleic acid contents to the cells.

The invention will be further described in the following examples, which do not limit the scope of the invention described in the claims.

EXAMPLES

Example 1

Figure 1B:
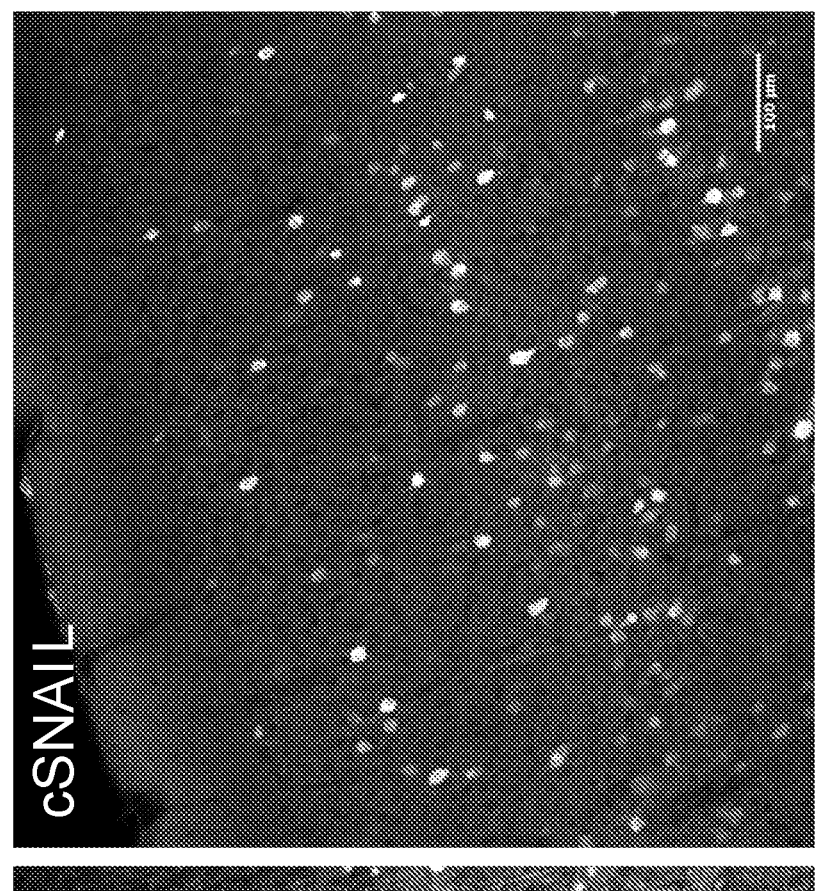
Figure 1B:
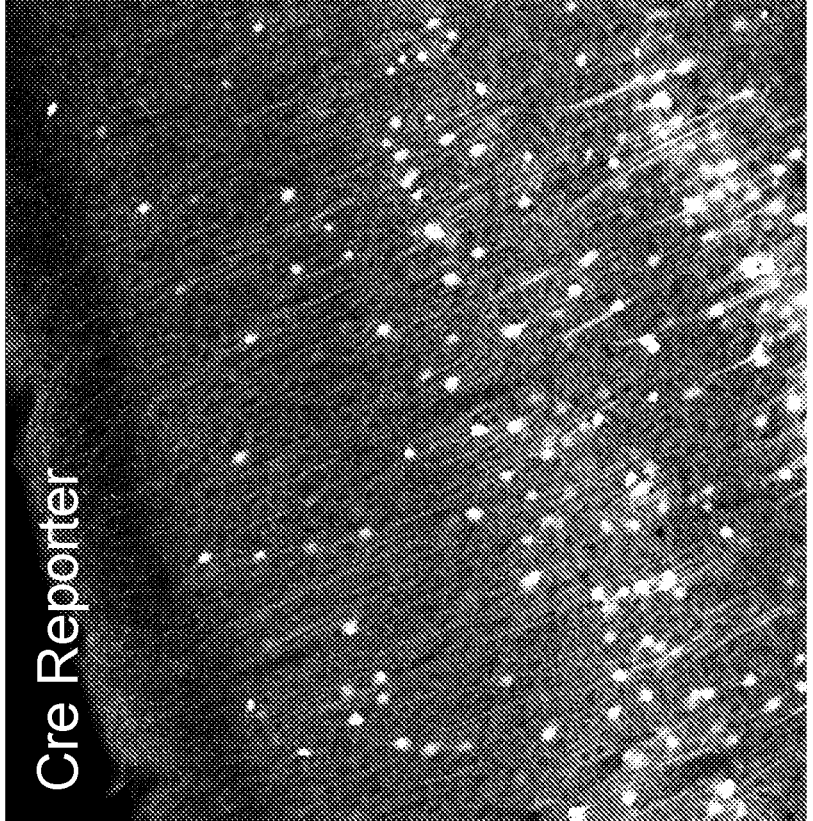
Figure 1C:
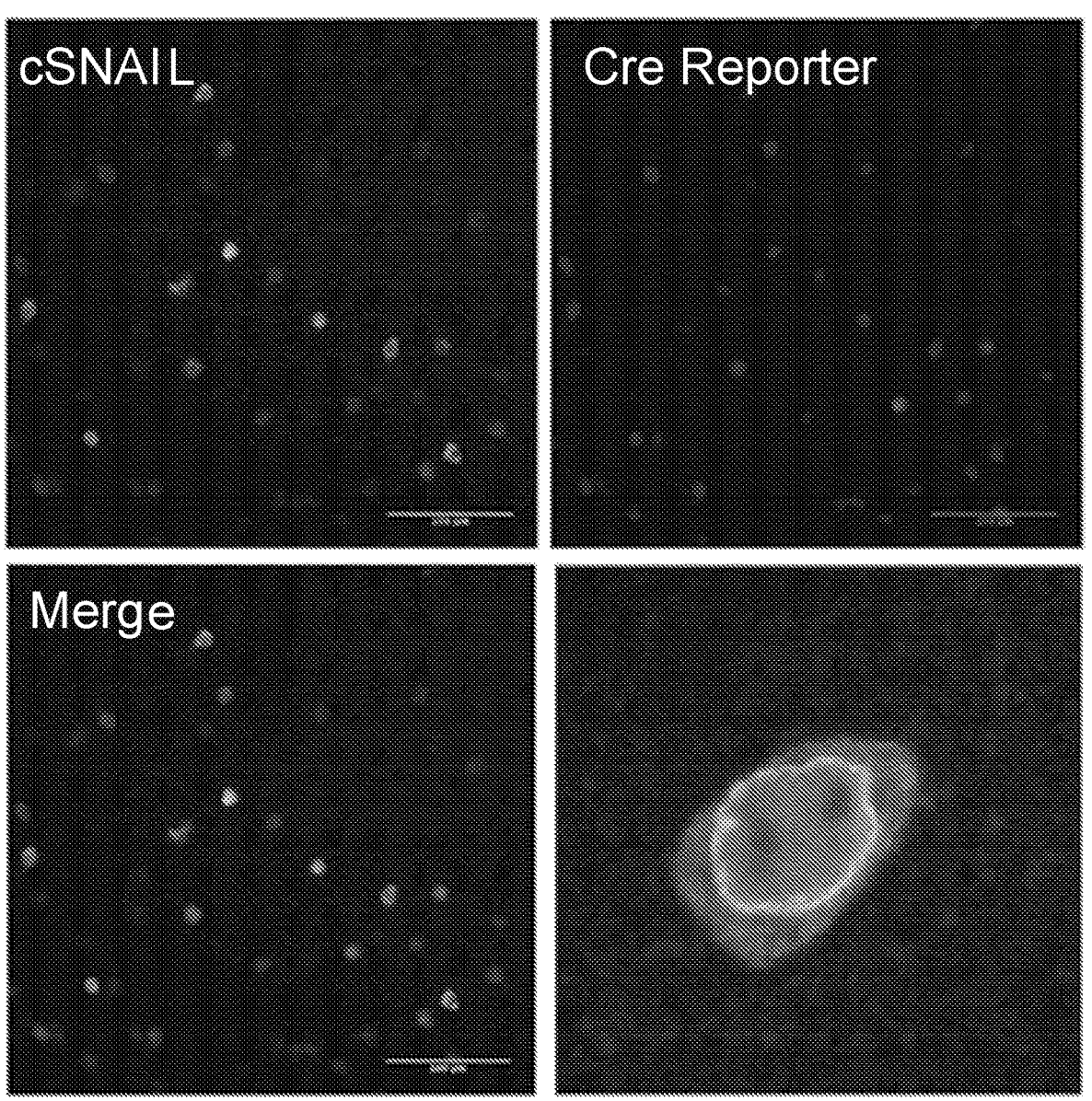
Figure 1D:
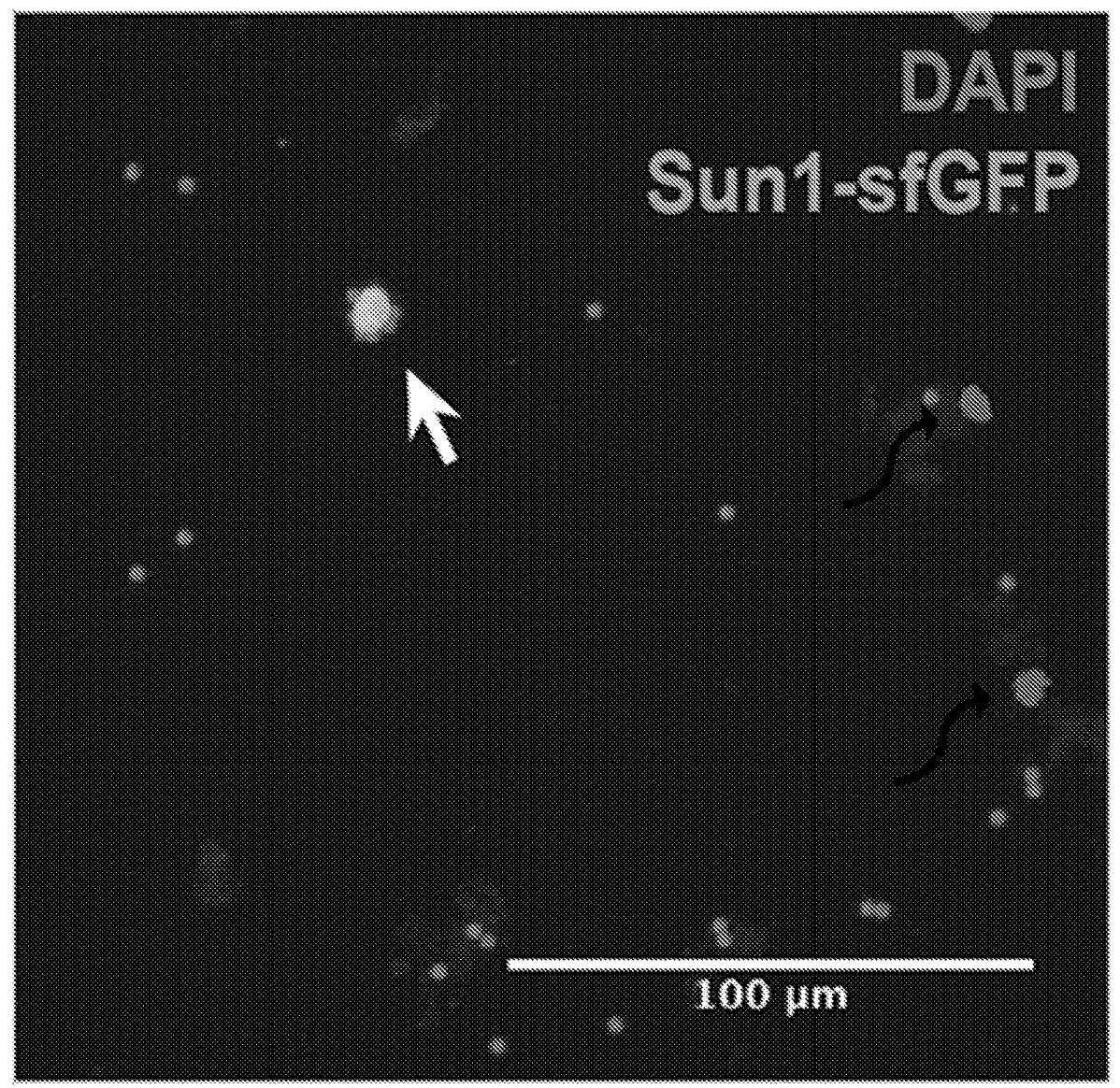
Figure 1E:
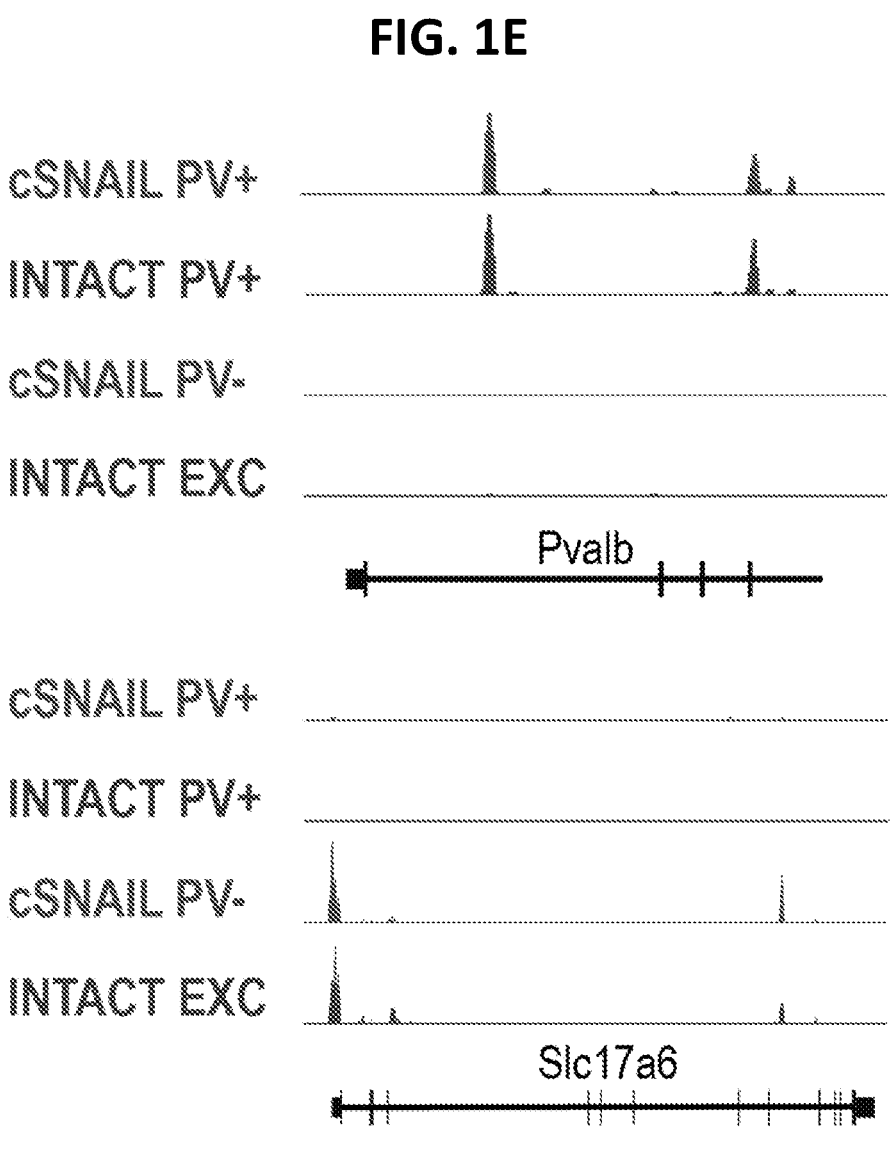
FIGS. 1E and 1F are schematics showing that when compared with the INTACT (Isolation of Nuclei TAgged in Specific Cell Types) method. Assay for Transposase-Accessible Chromatin (ATAC-seq) data from cSNAIL probes yielded similar cell type-specific open chromatin profiles.
Figure 1F:
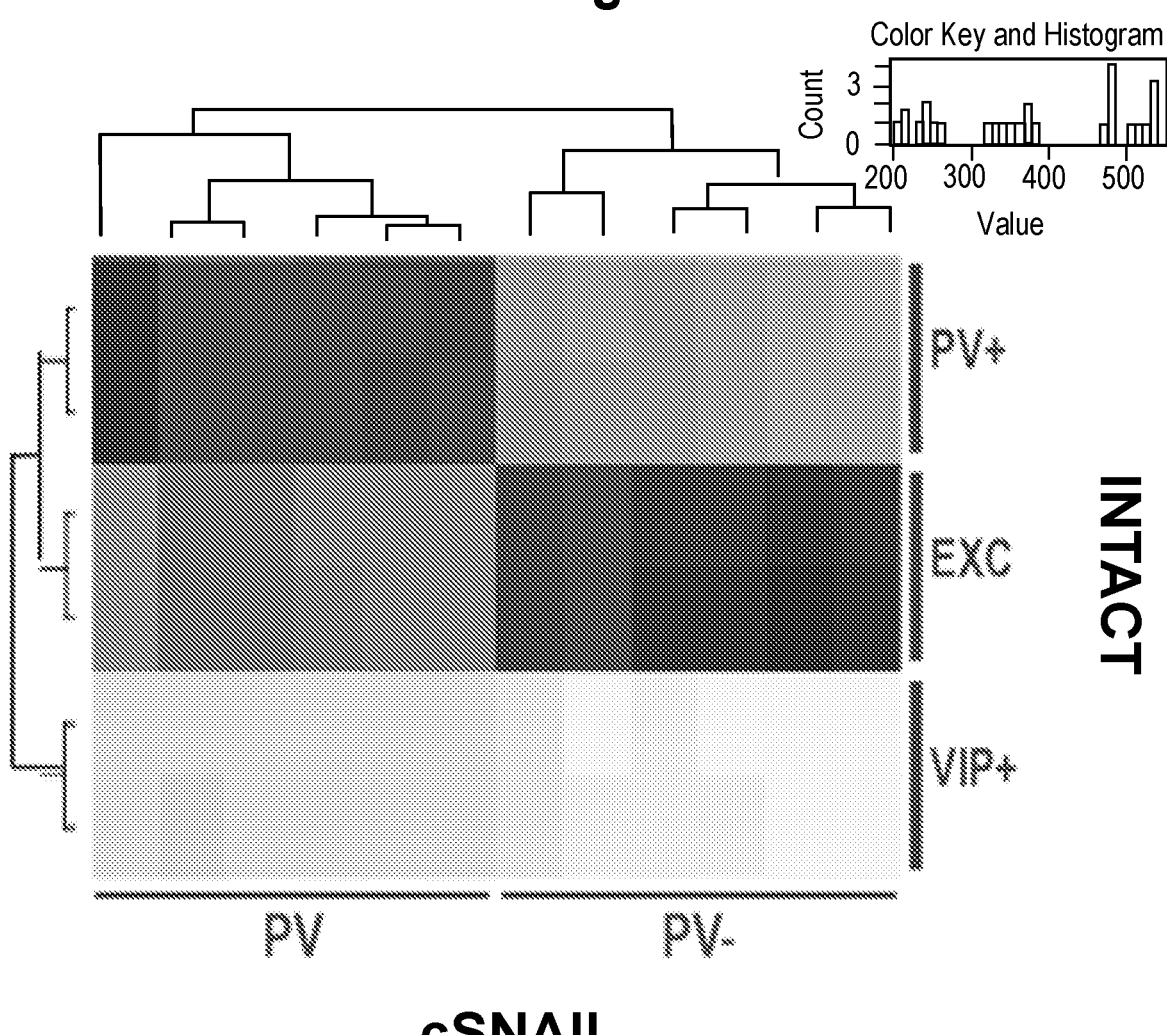

A cSNAIL viral probe was injected into PVcre mice, and Sun1GFP expression was selectively activated in Cre+ cells due to viral expression of Sun1GFP in PV+ neurons (FIGS. 1B and 1C). The success of this probe was quantified against the traditional double-transgenic strategy using different fluorophores in the same mouse. In the primary motor cortex (M1) of PVcre mice, the viral probe had an efficiency of 80.5% and a specificity of 94.1% (N=1088 cells). In SSTcre mice, the cSNAIL probe labeled SST neurons in M1 with an efficiency of 67.9% and a specificity of 94.7% (N=3359 cells). The efficiency was expected to be substantially less than 100% because it was limited by viral transduction rates, as AAV PHP.eB reportedly transduces 55-70% of neurons in the cortex (Chan et al., supra). The data for these neuron subtypes were in concordance or more optimistic than this characterization. Using cSNAIL technology, PV+ and PV– were isolated neurons from the mouse cortex, open chromatin assays (Buenrostro et al., *Curr. Protoc. Mol. Biol.* 109:21.29.1-21.29.9, 2015; and Buenrostro et al., *Nat. Methods* 10:1213-1218, 2013) were performed to identify active gene regulatory elements in these populations (FIGS. 1E and 1F). The resulting data were high quality and exhibited characteristic PV+ or PV– gene regulatory activity as previously described using INTACT. This demonstrated that the probes and methods provided herein are capable of generating comparable data as current state-of-the art technology.

A SNAIL viral probe for nuclei isolation of PV+ neurons also was validated. When a successful candidate sequence is cloned upstream of the modified Sun1GFP gene in the virus construct, it can only activate fluorescence expression in cells that can recognize and activate the promoter sequence. Thus, while a SNAIL viral probe will transduce cells indiscriminately, it will only express Sun1GFP in the targeted cell population.

To prioritize PV+ neuron-specific enhancer candidates, predictions from the SVM and CNN models were used. Three pairwise classifiers of each type (SVM and CNN) were built to discriminate sequences of open chromatin specific to PV+ versus PV– cell, excitatory neurons (EXC), and vasoactive intestinal peptide-expressing (VIP) neurons. The training data for the PV+ vs. PV– models were based on ATAC-seq collected using cSNAIL in Pvalb-2A-Cre transgenic mice. The training data for the two other models were based on published ATAC-seq conducted with the double-transgenic INTACT method (Mo et al., supra). All ATAC-seq data were processed using the ENCODE ATAC-seq pipeline (github.com/kundajelab/atac_dnase_pipelines), and reproducible peaks were called on 2-3 replicates of each cell type. Peak regions were tested for differential accessibility between two cell types using the negative binomial model in DESeq2 (Love et al., *Genome Biol* 15:1-21). Differential peaks (adjusted p<0.01 and |log 2FoldDifference|) were summit centered and unified to 500 bp in length. Where more than one peak summit was called within a differential region and it these summits were further than 100 bp apart, both were included in the training data. These regions were filtered to remove promoters, because promoters tend to be less cell type-specific than enhancers and may have different sequence properties. Regions that overlapped with super enhancers were also removed, as they are too long for viral constructs and may exhibit unique sequence features. To be able to test for over-fitting of the models, the data were divided by chromosome into separate training (chromosomes 3, 4, 5, 6, 10, 11, 12, 13, 14, 15, 16, 17, 18, 19, and X), validation (chromosomes 8 and 9), and test sets (chromosomes 1 and 2).

Figure 3:
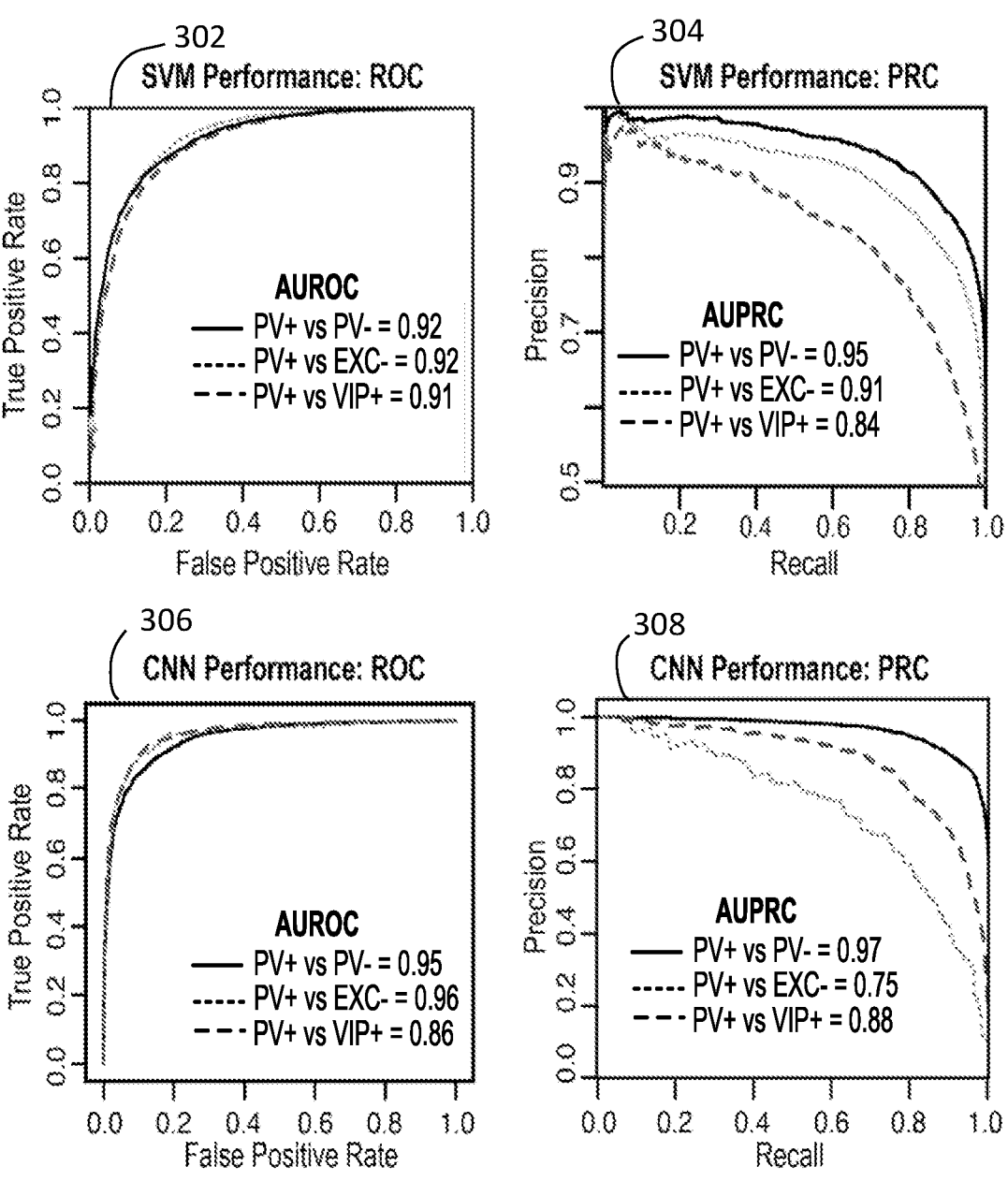
FIG. 3 is a series of graphs plotting the performance of gapped k-mer support vector machine (SVM) and convolutional neural network (CNN) models on predicting cell type-specific regulatory activity of genomic sequences in PV+ neurons relative to PV− neurons, excitatory neurons, and VIP+ neurons.

The SVM models were built using the center weighted gapped k-mer kernel (Ghandi et al., *PLoS Comp Bio* 10:e1003711, 2014: code available at github.com/Dongwon-Lee/lsgkm), option -t 4. The models with the best performance were constructed using the with the following parameters, PV+ vs. PV– model: -l 8 -d 2 -c 0.4 -k 6, PV+ vs. EXC model: -l 8 -d 2 -c 0.4 -k 6, PV+ vs. VIP model: -l 7 -d 1 -c 0.3 -k 6. After the training period, the models were evaluated on the held out validation set of enhancers with known cell type-specific activity. All three SVMs achieved a validation set AUROC>0.9 and AUPRC>0.83, shown in graphs 302 and 304 (FIG. 3). Of the top 100 most confident PV+ neuron-specific predictions in each model, 97-100 were true positives. Model performance on the PV+ and excitatory ATAC-seq peaks (Mo et al., supra) also was evaluated. On this independent data, the PV+ vs. PV– classifier achieved an accuracy of 77% and an F1 of 0.76. All three CNN models also achieved strong performance on the training set, as well as a held-out validation chromosome (AUROC>0.94, AUPRC>0.74), shown in graphs 306 and 308 (FIG. 3).

Figure 4A:
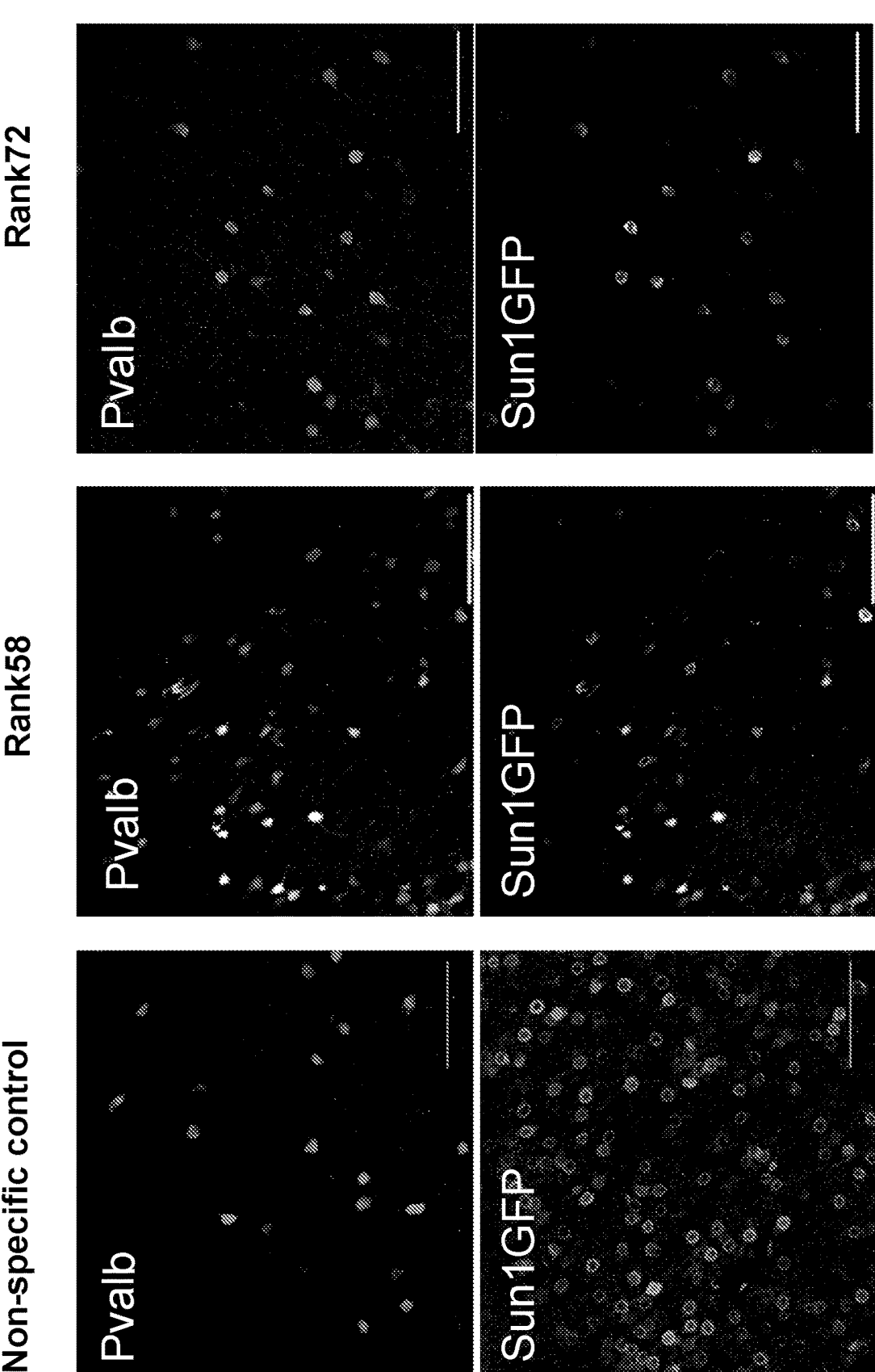
FIG. 4A is a set of images showing validation of two SNAIL probes for parvalbumin positive neurons, alongside a non-specific control virus. The images show Sun1GFP labeled cells and parvalbumin-immunoreactive neurons (Swant PV27-Alexa Fluor 594) within mouse cortical tissue. The scale bars measure 100 μm.
Figure 4B:
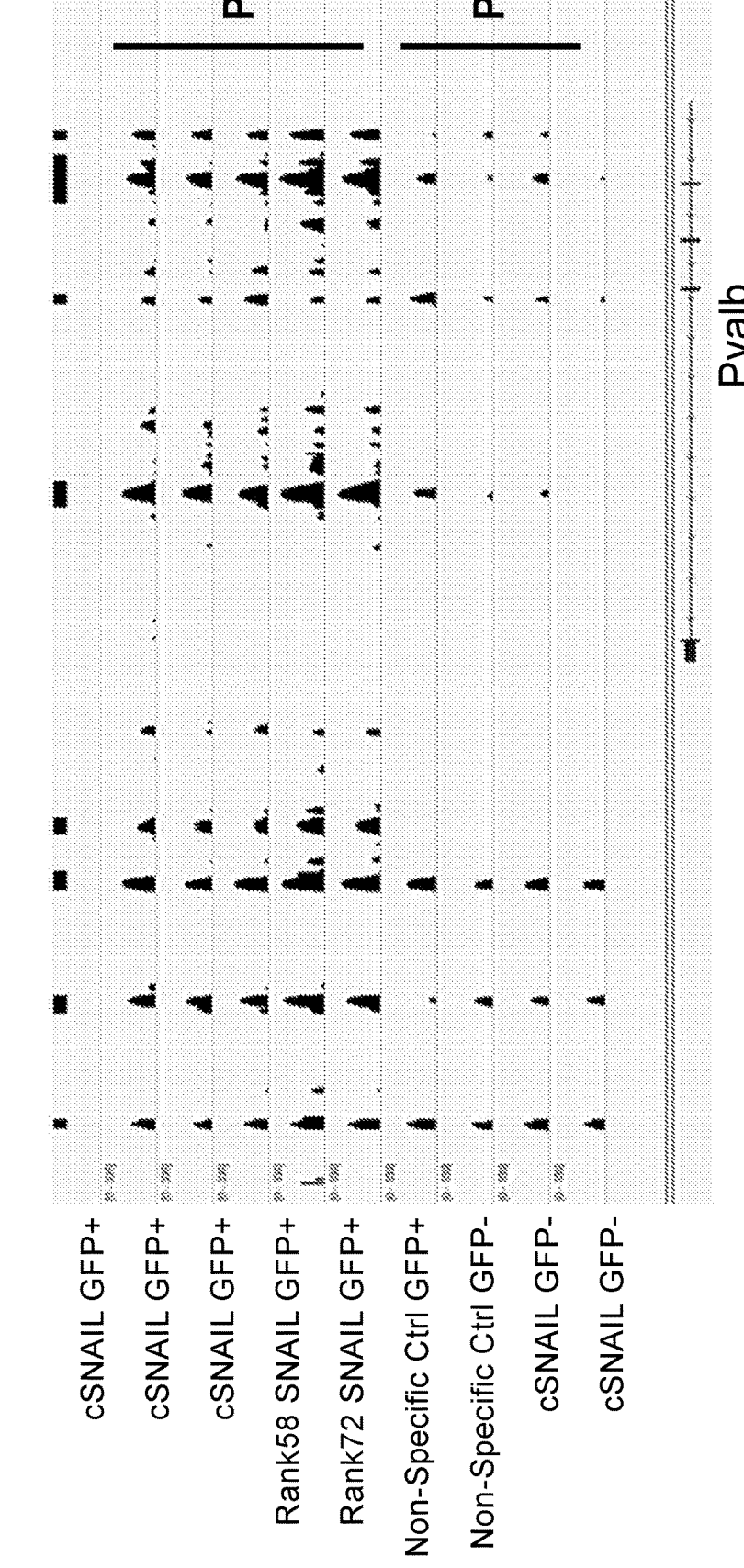
FIGS. 4B and 4C show that open chromatin signatures derived from SNAIL-isolated PV+ cells recapitulate known PV+ features from cSNAIL and single nucleus ATAC-seq data.
Figure 4C:
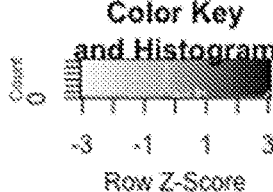
Figure 4C:
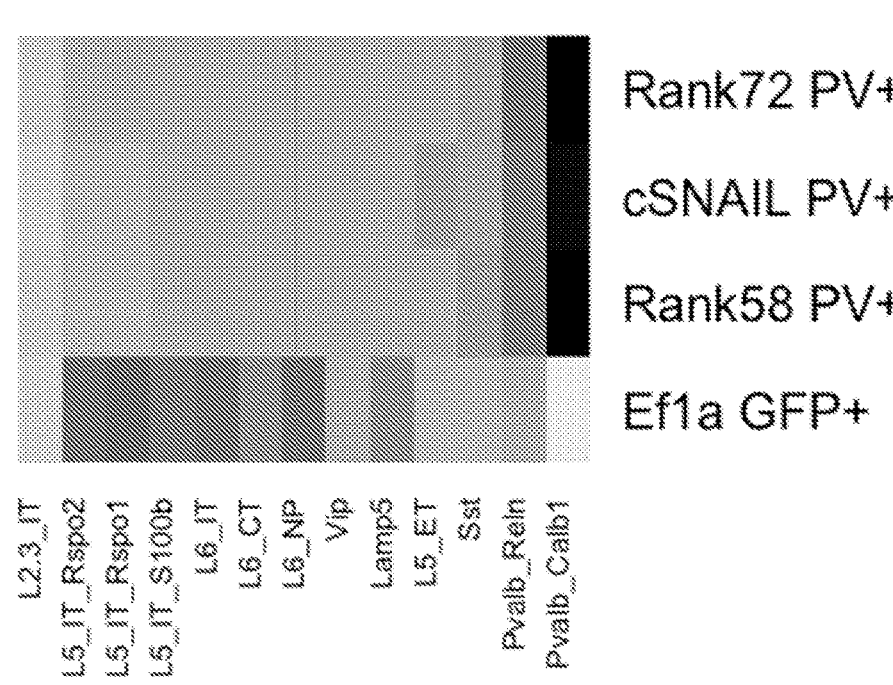

Using scores across all models and manual curation, four highly consistent PV+ neuron-specific regulatory sequences were identified as being most likely to induce PV+ specific Sun1GFP expression in an independent viral probe. These candidate sequences were incorporated into separate pAAV vectors, operably linked to the expression of a Sun1GFP fusion gene. A non-specific control vector also was designed with the same sequence except for the promoter region, which was replaced with a constitutive Ef1a promoter. After packaging into virus, these probes were assessed for their ability to drive PV+ specific expression of Sun1GFP in AAV by comparing Sun1GFP to PV neurons identified with antibodies against parvalbumin. Two of four viruses were successful at restricting Sun1GFP expression to PV+ neurons, hereafter referred to as Rank58 and Rank72 (FIG. 4A). Using affinity purification and ATAC-seq, it also was determined that the Rank58 and Rank72 viruses had chromatin landscapes that were similar to PV+ signatures collected with cSNAIL (FIG. 4B) or single nucleus ATAC-seq (FIG. 4C), indicating shared identity.

The materials and methods described herein have the striking benefit of strain independence. Because of this, the materials and methods can be used in wild type mice or any organism for which AAV can be used as a delivery method. Additionally, they can be used in conjunction with transgenic strains, such as disease models, which generally cannot be interbred with INTACT transgenic mice.

Thus, applications of cSNAIL and SNAIL are wide-ranging. For example, cSNAIL viral probes are an immediate alternative to double transgenic mice for cell isolation. These can be used with any existing cell type-specific Cre mouse strain that researchers may already be using. SNAIL probes provide an extremely powerful tool for cell isolation in any strain of mouse, and potentially other mammals.

Beyond cell labeling and isolation, applications of this viral gene driving technology also include, without limitation, cell type-specific CRISPR Cas9 expression, gene overexpression, and optogenetic stimuli. The SNAIL platform will give users unprecedented control over circuit manipulation at the resolution of individual neuronal subtypes. In one example, the AAV-based cell type-specific label of parvalbumin positive neurons can be used to therapeutically manipulate this specific neuron population in humans. This particular cell type has been causally linked to schizophrenia, Parkinson's disease, and Alzheimer's disease. Additionally, AAV-based therapies have shown promise in human subjects.

The exon-only sequence encoding the N-truncated version of Sun1GFP (SEQ ID NO:3), the Rank72 candidate PV specific enhancer (SEQ ID NO:4), the full plasmid including Rank72 and Sun1GFP (SEQ ID NO:5), and the Sun1GFP amino acid sequence (SEQ ID NO:6) were as follows:

```
N-truncated exon-only version of Sun1GFP (SNAIL Sun1GFP)
DNA sequence)
                                          (SEQ ID NO: 3)
ATGACCTCCAGGGTGTACTCCAGAGACAGGACTCTCAAACCACGGAAGGCAG

CCTCGGGAACCTTCTGGTGGCTAGGGAGCGGCTGGTACCAATTTGTTACTTTG

ATTCTTGGCTGAATGTCTTTCTTCTTACCAGGTGCCTTCGAAATATTTGCAAG

GTTTTTGTCTTGCTCCTCCCACTCCTACTTTTACTAGGTGCTGGTGTCTCCCTG

TGGGGCCAGGGAAACTTCTTCTCACTCCTACCAGTGCTGAACTGGACGGCCAT

GCAGCCAACACAGAGGGTGGACGATTCCAAGGGCATGCATAGACCTGGCCCT

CTTCCCCCGAGCCCACCTCCAAAGGTTGATCACAAGGCTTCCCAGTGGCCTCA

GGAGAGTGACATGGGGCAGAAGGTAGCTTCTTTGAGTGCGCAGTGCCACAAC

CATGATGAGAGACTTGCAGAGCTGACAGTCCTGCTTCAGAAACTACAGATAC

GGGTAGACCAAGTGGATGACGGCAGGGAAGGGCTGTCACTGTGGGTCAAGA

ATGTGGTTGGACAGCACCTGCAGGAGATGGGCACCATAGAACCACCTGATGC

TAAGACTGACTTCATGACTTTCCACCATGACCATGAAGTGCGTCTCTCCAACT

TGGAAGATGTTCTTAGAAAACTGACAGAAAAATCTGAGGCTATCCAGAAGGA

GCTGGAAGAAACCAAGCTGAAAGCAGGCAGCAGGGATGAAGAGCAGCCCCT

CCTTGACCGTGTGCAGCACCTAGAACTGGAACTGAACCTGTTGAAGTCACAG

CTGTCAGACTGGCAGCATCTGAAGACCAGCTGTGAGCAGGCTGGGGCCCGCA

TCCAGGAGACTGTGCAGCTCATGTTCTCTGAGGATCAGCAGGGCGGTTCCCTC

GAGTGGCTATTAGAGAAGCTTTCTTCTCGGTTCGTGAGCAAGGATGAGCTGC

AGGTGCTCTTACATGACCTTGAGCTGAAACTGCTGCAGAATATCACACACCA

CATCACCGTGACAGGACAGGCCCCGACATCCGAGGCTATTGTGTCTGCCGTG

AATCAGGCAGGGATTTCAGGAATCACAGAAGCGCAAGCACATATCATTGTGA

ACAATGCTCTGAAGCTGTACTCCCAAGACAAGACGGGGATGGTGGACTTTGC

TCTGGAGTCTGGAGGTGGCAGCATCCTAAGCACTCGGTGCTCTGAGACCTAT

GAGACCAAGACGGCACTGCTGAGCCTGTTTGGGGTCCCACTGTGGTACTTCTC

ACAGTCACCTCGAGTGGTGATCCAGCCCGACATCTACCCAGGGAATTGCTGG

GCGTTCAAAGGTTCCCAGGGGTACCTGGTGGTGCGGTTGTCCATGAAGATCT

ACCCAACCACATTCACCATGGAACACATTCCAAAGACACTATCACCCACTGG

TAACATCTCCAGTGCCCCCAAAGACTTTGCAGTCTATGGACTGGAAACGGAG

TATCAAGAAGAGGGGCAGCCTCTGGGACGGTTCACCTATGACCAGGAAGGAG

ACTCACTCCAGATGTTCCACACACTGGAAAGACCTGACCAAGCCTTCCAGAT

AGTAGAGCTCCGGGTCCTGTCCAACTGGGGCCACCCTGAGTACACTTGCCTCT

ACCGGTTCCGAGTCCACGGAGAGCCCATCCAGATGAGCAAAGGAGAAGAAC

TTTTCACTGGAGTTGTCCCAATTCTTGTTGAATTAGATGGTGATGTTAATGGG
```

-continued

CACAAATTTTCTGTCCGTGGAGAGGGTGAAGGTGATGCTACAAACGGAAAAC

TCACCCTTAAATTTATTTGCACTACTGGAAAACTACCTGTTCCATGGCCAACA

CTTGTCACTACTCTGACCTATGGTGTTCAATGCTTTTCCCGTTATCCGGATCAC

ATGAAACGGCATGACTTTTTCAAGAGTGCCATGCCCGAAGGTTATGTACAGG

AACGCACTATATCTTTCAAAGATGACGGGACCTACAAGACGCGTGCTGAAGT

CAAGTTTGAAGGTGATACCCTTGTTAATCGTATCGAGTTAAAAGGTATTGATT

TTAAAGAAGATGGAAACATTCTCGGACACAAACTCGAGTACAACTTTAACTC

ACACAATGTATACATCACGGCAGACAAACAAAAGAATGGAATCAAAGCTAA

CTTCAAAATTCGCCACAACGTTGAAGATGGTTCCGTTCAACTAGCAGACCATT

ATCAACAAATACTCCAATTGGCGATGGCCCTGTCCTTTTACCAGACAACCAT

TACCTGTCGACACAATCTGTCCTTTCGAAAGATCCCAACGAAAAGCGTGACC

ACATGGTCCTTCTTGAGTTTGTAACTGCTGCTGGGATTACACATGGCATGGAT

GAGCTCTACAAATAA

Rank72 candidate PV specific enhancer
(SNAIL_Rank72_PromoterSequence)
                                                    (SEQ ID NO: 4)
attggtttgccttacacgctttgttgaactgcatttgccatgactccatagag aaaaacacgccgaaaagcttctctaggtggttcccacatcttcttgtggattc cgtggactcgggtcaactagcagagtgatgtcagctgctatacatagactcac atggagttttgctaagacaggctcacgtgctgaggcaagacacgtggtaaggc aagacctgtagaggacacttggtgattttgaggcagtataaataggactcaac ggacggtgatggaggctgggcttgcttgcataactagctttgcagtgcttctt ggtctcgcgtcttcactgaccttcgatttgttgagagcggcacagttgagaac ttccctggcatccctggtggtcctaattcctcctgctaactccagccaattc ggctgaagcctggcagtttctgctaggtcgggccaccgctgctgattcgtatt tgctatcccaactctaccaatctg Full plasmid including Rank72 and Sun1GFP
(SNAIL_Rank72.dna)
                                                    (SEQ ID NO: 5)
CCTGCAGGCAGCTGCGCGCTCGCTCGCTCACTGAGGCCGCCCGGGCAAAGCC

CGGGCGTCGGGCGACCTTTGGTCGCCCGGCCTCAGTGAGCGAGCGAGCGCGC

AGAGAGGGAGTGGCCAACTCCATCACTAGGGGTTCCTGCGGCCGCACGCGTG

CGATCGCCATATGAGGCCTCATTGGCCATTGTAATTGGTTTGCCTTACACGCT

TTGTTGAACTGCATTTGCCATGACTCCATAGAGAAAAACACGCCGAAAAGCT

TCTCTAGGTGGTTCCCACATCTTCTTGTGGATTCCGTGGACTCGGGTCAACTA

GCAGAGTGATGTCAGCTGCTATACATAGACTCACATGGAGTTTTGCTAAGAC

AGGCTCACGTGCTGAGGCAAGACACGTGGTAAGGCAAGACCTGTAGAGGAC

ACTTGGTGTTTTGAGGCAGTATAAATAGGACTCAACGGACGGTGATGGAGGC

TGGGCTTGCTTGCATAACTAGCTTTGCAGTGCTTCTTGGTCTCGCGTCTTCACT

GACCTTCGATTTGTTGAGAGCGGCACAGTTGAGAACTTCCCCTGGCATCCCTG

GTGGTCCTAATTCCTCCTGCTAACTCCAGCCAATTCGGCTGAAGCCTGGCAGT

TTCTGCTAGGTCGGGCCACCGCTGCTGATTCGTATTTGCTATCCCAACTCTAC

CAATCTGGAATTAATTCGCTGTCTGCGAGGGCCAGCTGTTGGGGTGAGTACTC

CCTCTCAAAAGCGGGCATGACTTCTGCGCTAAGATTGTCAGTTTCCAAAAACG

AGGAGGATTTGATATTCACCTGGCCCGCGGTGATGCCTTTGAGGGTGGCCGC

GTCCATCTGGTCAGAAAAGACAATCTTTTTGTTGTCAAGCTTGAGGTGTGGCA

GGCFTGAGATCTGGCCATACACTTGAGTGACAATGACATCCACTTTGCCTTTC

TCTCCACAGGTGTCCACTCCCAGGTCCAACTGCAGGTCGCGACTAGCGGATCC

AATGAGCTCCAGGGTGTACTCCAGAGACAGGACTCTCAAACCACGGAAGGCA

GCCTCGGGAACCTTCTGGTGGCTAGGGAGCGGCTGGTACCAATTTGTTACTTT

GATTTCTTGGCTGAATGTCTTTCTTCTTACCAGGTGCCTTCGAAATATTTGCAA

GGTTTTTGTCTTGCTCCTCCCACTCCTACTTTTACTAGGTGCTGGTGTCTCCCT

GTGGGGCCAGGGAAACTTCTTCTCACTCCTACCAGTGCTGAACTGGACGGCC

ATGCAGCCAACACAGAGGGTGGACGATTCCAAGGGCATGCATAGACCTGGCC

CTCTTCCCCCGAGCCCACCTCCAAAGGTTATCACAAGGCTTCCCAGTGGCCT

CAGGAGAGTGACATGGGGCAGAAGGTAGCTTCTTTGAGTGCGCAGTGCCACA

ACCATGATGAGAGACTTGCAGAGCTGACAGTCCTGCTTCAGAAACTACAGAT

ACGGGTAGACCAAGTGGATGACGGCAGGGAAGGGCTGTCACTGTGGGTCAA

GAATGTGGTTGGACAGCACCTGCAGGAGATGGGCACCATAGAACCACCTGAT

GCTAAGACTGACTTCATGACTTTCCACCATGACCATGAAGTGCGTCTCTCCAA

CTTGGAAGATGTTCTTAGAAAACTGACAGAAAAATCTGAGGCTATCCAGAAG

GAGCTGGAAGAAACCAAGCTGAAAGCAGGCAGCAGGGATGAAGAGCAGCCC

CTCCTTGACCGTGTGCAGCACCTAGAACTGGAACTGAACCTGTTGAAGTCAC

AGCTGTCAGACTGGCAGCATCTGAAGACCAGCTGTGAGCAGGCTGGGGCCCG

CATCCAGGAGACTGTGCAGCTCATGTICTCTGAGGATCAGCAGGGCGGTTCC

CTCGAGTGGCTATTAGAGAAGCTTTCTTCTCGGTTCGTGAGCAAGGATGAGCT

GCAGGTGCTCTTACATGACCTTGAGCTGAAACTGCTGCAGAATATCACACAC

CACATCACCGTGACAGGACAGGCCCCGACATCCGAGGCTATTGTGTCTGCCG

TGAATCAGGCAGGGATTTCAGGAATCACAGAAGCGCAAGCACATATCATTGT

GAACAATGCTCTGAAGCTGTACTCCCAAGACAAGACGGGGATGGTGGACTTT

GCTCTGGAGTCTGGAGGTGGCAGCATCCTAAGCACTCGGTGCTCTGAGACCT

ATGAGACCAAGACGGCACTGCTGAGCCTGTTTGGGGTCCCACTGTGGTACTTC

TCACAGTCACCTCGAGTGGTGATCCaGCCCGACATCTACCCAGGGAATTGCT

GGGCGTTCAAAGGTTCCCAGGGGTACCTGGTGGTGCGGTTGTCCATGAAGAT

CTACCCAACCACATTCACCATGGAACACATTCCAAAGACACTATCACCCACT

GGTAACATCTCCAGTGCCCCCAAAGACTTTGCAGTCTATGGACTGGAAACGG

AGTATCAAGAAGAGGGGCAGCCTCTGGGACGGTTCACCTATGACCAGGAAGG

AGACTCACTCCAGATGTTCCACACACTGGAAAGACCTGACCAAGCCTTCCAG

ATAGTAGAGCTCCGGGTCCTGTCCAACTGGGGCCACCCTGAGTACACTTGCCT

CTACCGGTTCCGAGTCCACGGAGAGCCCATCCAGATGAGCAAAGGAGAAGA

ACTTTTCACTGGAGTTGTCCCAATTCTTGTTGAATTAGATGGTGATGTTAATG

GGCACAAATTTTCTGTCCGTGGAGAGGGTGAAGGTGATGCTACAAACGGAAA

ACTCACCCTTAAATTTATTTGCACTACTGGAAAACTACCTGTTCCATGGCCAA

CACTTGTCACTACTCTGACCTATGGTGTTCAATGCTTTTCCCGTTATCCGGATC

ACATGAAACGGCATGACTTTTTCAAGAGTGCCATGCCCGAAGGTTATGTACA

GGAACGCACTATATCTTTCAAAGATGACGGGACCTACAAGACGCGTGCTGAA

GTCAAGTTrGAAGGTGATACCCTTGTTAATCGTATCGAGTTAAAAGGTATTGA

TTTTAAAGAAGATGGAAACATTCTCGGACACAAACTCGAGTACAACTTTAAC

TCACACAATGTATACATCACGGCAGACAAACAAAAGAATGGAATCAAAGCTA

ACTTCAAAATTCGCCACAACGTTGAAGATGGTTCCGTTCAACTAGCAGACCAT

TATCAACAAAATACTCCAATTGGCGATGGCCCTGTCCTTTTACCAGACAACCA

TTACCTGTCGACACAATCTGTCCTTTCGAAAGATCCCAACGAAAAGCGTGACC

ACATGGTCCTTCTTGAGTTTGTAACTGCTGCTGGGATTACACATGGCATGGAT

GAGCTCTACAAATAAGGCGCGGAATTCGATATCAAGCTTATCGATAATCAAC

CTCTGGATTACAAAATTTGTGAAAGATTGACTGGTATTCTTAACTATGTTGCT

CCTTTTACGCTATGTGGATACGCTGCTTTAATGCCTTTGTATCATGCTATTGCT

TCCCGTATGGCTTTCATTTTCTCCTCCTTGTATAAATCCTGGTTGCTGTCTCTTT

ATGAGGAGTTGTGGCCCGTTGTCAGGCAACGTGGCGTGGTGTGCACTGTGTTT

GCTGACGCAACCCCCACTGGTTGGGGCATTGCCACCACCTGTCAGCTCCTTTC

CGGGACTTTCGCTTTCCCCCTCCCTATTGCCACGGCGGAACTCATCGCCGCCT

GCCTTGCCCGCTGCTGGACAGGGGCTCGGCTGTTGGGCACTGACAATTCCGTG

GTGTTGTCGGGGAAATCATCGTCCTTTCCTTGGCTGCTCGCCTGTGTTGCCAC

CTGGATTCTGCGCGGGACGTCCTTCTGCTACGTCCCTTCGGCCCTCAATCCAG

CGGACCTTCCTTCCCGCGGCCTGCTGCCGGCTCTGCGGCCTCTTCCGCGTCTTC

GCCTTCGCCCTCAGACGAGTCGGATCTCCCTTTGGGCCGCCTCCCCGCATCGA

TACCGAGCGCTGCTCGAGAGATCTACGGGTGGCATCCCTGTGACCCCTCCCCA

GTGCCTCTCCTGGCCCTGGAAGTTGCCACTCCAGTGCCCACCAGCCTGTCCT

AATAAAATTAAGTTGCATCATTTTGTCTGACTAGGTGTCCTTCTATAATATTAT

GGGGTGGAGGGGGGTGGTATGGAGCAAGGGGCAAGTTGGGAAGACAACCTG

TAGGGCCTGCGGGGTCTATTGGGAACCAAGCTGGAGTGCAGTGGCACAATCT

TGGCTCACTGCAATCTCCGCCTCCTGGGTTCAAGCGATTCTCCTGCCTCAGCC

TCCCGAGTTGTTGGGATTCCAGGCATGCATGACCAGGCTCAGCTAATTTTTGT

TTmTGGTAGAGACGGGGTTTCACCATATTGGCCAGGCTGGTCTCCAACTCC

TAATCTCAGGTGATCTACCCACCTTGGCCTCCCAAATTGCTGGGATTACAGGC

GTGAACCACTGCTCCCTTCCCTGTCCTTCTGATTTTGTAGGTAACCACGTGCG

GACCGAGCGGCCGCAGGAACCCCTAGTGATGGAGTTGGCCACTCCCTCTCTG

CGCGCTCGCTCGCTCACTGAGGCCGGGCGACCAAAGGTCGCCCGACGCCCGG

GCTTTGCCCGGGCGGCCTCAGTGAGCGAGCGAGCGCGCAGCTGCCTGCAGGG

GCGCCTGATGCGGTATTTTCTCCTTACGCATCTGTGCGGTATTTCACACCGCA

TACGTCAAAGCAACCATAGTACGCGCCCTGTAGCGGCGCATTAAGCGCGGCG

GGTGTGGTGGTTACGCGCAGCGTGACCGCTACACTTGCCAGCGCCCTAGCGC

CCGCTCCTTTCGCTTTCTTCCCTTCCTTTCTCGCCACGTTCGCCGGCTTTCCCCG

TCAAGCTCTAAATCGGGGGCTCCCTTTAGGGTTCCGATTTAGTGCTTTACGGC

ACCTCGACCCCAAAAAACTTGATTTGGGTGATGGTTCACGTAGTGGGCCATC

GCCCTGATAGACGGTTTTTCGCCCTTTGACGTTGGAGTCCACGTTCTTTAATA

-continued

```
GTGGACTCTTGTTCCAAACTGGAACAACACTCAACCCTATCTCGGGCTATTCT

TTTGATTTATAAGGGATTTTGCCGATTTCGGCCTATTGGTTAAAAAATGAGCT

GATTTAACAAAAATTrAACGCGAATTTTAACAAAATATTAACGTTTACAATTT

TATGGTGCACTCTCAGTACAATCTGCTCTGATGCCGCATAGTTAAGCCAGCCC

CGACACCCGCCAACACCCGCTGACGCGCCCTGACGGGCTTGTCTGCTCCCGG

CATCCGCTTACAGACAAGCTGTGACCGTCTCCGGGAGCTGCATGTGTCAGAG

GTTTTCACCGTCATCACCGAAACGCGCGAGACGAAAGGGCCTCGTGATACGC

CTATTTTTATAGGTTAATGTCATGATAATAATGGTTTCTTAGACGTCAGGTGG

CACTTTTCGGGGAAATGTGCGCGGAACCCCTATTTGTTTATTTTTCTAAATAC

ATTCAAATATGTATCCGCTCATGAGACAATAACCCTGATAAATGCTTCAATAA

TATTGAAAAAGGAAGAGTATGAGTATTCAACATTTCCGTGTCGCCCTTATTCC

CTTTTTTGCGGCATTTTGCCTTCCTGTTTTTGCTCACCCAGAAACGCTGGTGAA

AGTAAAAGATGCTGAAGATCAGTTGGGTGCACGAGTGGGTTACATCGAACTG

GATCTCAACAGCGGTAAGATCCTTGAGAGTTTTCGCCCCGAAGAACGTTTTCC

AATGATGAGCACTTTTAAAGTTCTGCTATGTGGCGCGGTATTATCCCGTATTG

ACGCCGGGCAACGAGCAACTCGGTCGCCGCATACACTATTCTCAGAATGACTT

GGTTGAGTACTCACCAGTCACAGAAAAGCATCTTACGGATGGCATGACAGTA

AGAGAATTATGCAGTGCTGCCATAACCATGAGTGATAACACTGCGGCCAACT

TACTTCTGACAACGATCGGAGGACCGAAGGAGCTAACCGCTTTTTTGCACAA

CATGGGGGATCATGTAACTCGCCTTGATCGTTGGGAACCGGAGCTGAATGAA

GCCATACCAAACGACGAGCGTGACACCACGATGCCTGTAGCAATGGCAACAA

CGTTGCGCAAACTATTAACTGGCGAACTACTTACTCTAGCTTCCCGGCAACAA

TTAATAGACTGGATGGAGGCGGATAAGTTGCAGGACCACTTCTGCGCTCGG

CCCTICCGGCTGGCTGGTTTATTGCTGATAAATCTGGAGCCGGTGAGCGTGGG

TCTCGCGGTATCATTGCAGCACTGGGGCCAGATGGTAAGCCCTCCCGTATCGT

AGTTATCTACACGACGGGGAGTCAGGGAACTATGGATGAACGAAATAGACAG

ATCGCTGAGATAGGTGCCTCACTGATTAAGCATTGGTAACTGTCAGACCAAG

TTTACTCATATATACTTTAGATTGATTTAAAACTTCATTTTTAATTTAAAAGGA

TCTAGGTGAAGATCCTTTTTGATAATCTCATGACCAAAATCCCTTAACGTGAG

TTTTCGTTCCACTGAGCGTCAGACCCCGTAGAAAAGATCAAAGGATCTTCTTG

AGATCCTTTTTTCTGCGCGTAATCTGCTGCTTGCAAACAAAAAAACCACCGC

TACCAGCGGTGGTTTGTTTGCCGGATCAAGAGCTACCAACTCTTTTTCCGAAG

GTAACTGGCTTCAGCAGAGCGCAGATACCAAATACTGTCCTTCTAGTGTAGCC

GTAGTTAGGCCACCACTTCAAGAACTCTGTAGCACCGCCTACATACCTCGCTC

TGCTAATCCTGTTACCAGTGGCTGCTGCCAGTGGCGATAAGTCGTGTCTTACC

GGGTTGGACTCAAGACGATAGTTACCGGATAAGGCGCAGCGGTCGGGCTGAA

CGGGGGGTTCGTGCACACAGCCCAGCTTGGAGCGAACGACCTACACCGAACT

GAGATACCTACAGCGTGAGCTATGAGAAAGCGCCACGCTTCCCGAAGGGAGA

AAGGCGGACAGGTATCCGGTAAGCGGCAGGGTCGGAACAGGAGAGCGCACG

AGGGAGCTTCCAGGGGGAAACGCCTGGTATCTTTATAGTCCTGTCGGGTTTCG
```

-continued

```
CCACCTCTGACTTGAGCGTCGATTTTTGTGATGCTCGTCAGGGGGGCGGAGCC

TATGGAAAAACGCCAGCAACGCGGCCTTTTTACGGTTCCTGGCCTTTTGCTGG

CCTTTTGCTCACATGT

Sun1GFP polypeptide
                                          (SEQ ID NO: 6)
MTSRVYSRDRTLKPRKAASGTFWWLGSGWYQFVTLISWLNVFLLTRCLRNICKV

FVLLLPLLLLLGAGVSLWGQGNFFSLLPVLNWTAMQPTQRVDDSKGMHRPGPLP

PSPPPKVDHKASQWPQESDMGQKVASLSAQCHNHDERLAELTVLLQKLQIRVDQ

VDDGREGLSLWVKNVVGQHLQEMGTIEPPDAKTDFMTFFIHDHEVRLSNLEDVL

RKLTEKSEAIQKELEETKLKAGSRDEEQPLLDRVQHLELELNLLKSQLSDWQHLK

TSCEQAGARIQETVQLMFSEDQQGGSLEWLLEKLSSRFVSKDELQVLLHDLELKL

LQNITHHITVTGQAPTSEAIVSAVNQAGISGITEAQAHHVNNALKLYSQDKTGMV

DFALESGGGSILSTRCSEITETKTALLSLFGVPLWYFSQSPRVVIQPDIYPGNCWA

FKGSQGYLVVRLSMKIYPTTFTMEHIPKTLSPTGNISSAPKDFAVYGLETEYQEEG

QPLGRFIYDQEGDSLQMFHTLERPDQAFQIVELRVLSNWGHPEYTCLYRFRVHG

EPIQMSKGEELFTGVVPILVELDGDVNGHKFSVRGEGEGDATNGKLTLKFICTTGKLP

VPWPTLVTTLTYGVQCFSRYPDHMKRHDFFKSMIPEGYVQERTISFKDDGTYKTRAE

VKFEGDTLVNRIELKGIDFKEDGNILGHKLEYNFNSHNVYITADKQKNGIKANFKIRH

NVEDGSVQLADHYQQNTPIGDGPVLLPFDNHYLSTQSVISKDPNEKRDHMVLLEFVTA

AGITHGMDELYK
[residues 2-551 are amino acids 208-757 of
the Mus musculus Sun1 transcript variant 5 (GENBANK ®
Accession No. NM_001256118.1), and residues 552-789
(in italics) are the superfolder GFP amino acid sequence]
```

35

Example 2—Cell Type-Specific Oxidative Stress Genomic Signatures in the Globus Pallidus of Dopamine Depleted Mice Neuron subtype dysfunction is a key contributor to the motor deficits observed in dopamine depleted mouse models of Parkinson's disease. For example, cell type-specific optogenetic stimulation of external globus pallidus (GPe) parvalbumin-expressing neurons (PV+)—but not global GPe stimulation—rescues normal motor behavior in dopamine depleted mice. Despite the importance of these cells in the disease process, the molecular correlates of GPe PV+ neuron performance after DD remain unknown due to the difficulty of isolating specific neuron subtypes in the brain. To address this issue, the cSNAIL viral affinity purification strategy was developed to isolate Cre recombinase-expressing (Cre+) nuclei from the adult mouse brain. Specifically, cSNAIL was used to isolate PV+ neurons from the cortex, striatum, and GPe of 6-hydroxydopamine (6-OHDA) lesioned mice and sham controls. In parallel, RNA-seq and ATAC-seq (Buenrostro et al. 2013, supra; and Buenrostro et al. 2015, supra) were conducted on cSNAIL-isolated PV+ populations and the remaining PV– cells in each brain region. With this strategy, GPe PV+ neuron-specific epigenetic and transcriptional responses to DD were identified that are related to cellular oxygen sensing and oxidative stress, providing new insight into the molecular pathology of PD.

Materials and Methods

AAV Design.

Several modifications were made to the INTACT system to allow it to be delivered using AAV. First, an N-truncated version of the human SUN1 gene (amino acids 208-913) was used. This version retained the ability to localize to the nuclear envelope in a manner that was resistant to detergent tissue homogenization as characterized by Haque et al. (*J Biol Chem* 285:3487-3498, 2010). Second, only the DNA sequence of exonic regions of SUN1 was incorporated into the construct. Third, the SUN1GFP fusion gene included one copy of superfolder GFP instead of two. Finally, the Cre-dependent mechanism was adjusted from a loxp-flanked stop codon to the double inverted orientation (DIO) system. In the initial cSNAIL genome, the SUN1GFP gene is in the reverse orientation with respect to the promoter such that the gene cannot be expressed. When the virus encounters Cre recombinase protein (Cre), it acts on the double flanking lox sites to excise the SUN1GFP gene and re-insert it in the correct orientation for transcription (FIG. 1A).

Vector Construction.

The modified SUN1GFP fusion sequence fragment was synthesized by Integrated DNA Technologies (IDT; Coralville, IA) and contained flanking restriction sites for SgsI and Bspol. The SUN1GFP sequence was inserted into an AAV DIO backbone vector with an Ef1a promoter using standard restriction cloning, pAAV-Ef1a-DIO-EGFP-WPRE-pA was obtained from Bernardo Sabatini (n2t.net/addgene:37084; RRID: Addgene_37084)(Saunders et al., Front Neural Circuits 6:47, 2012). The ligation was transformed into electrocompetent bacteria, and positive clones were selected and sequences were confirmed with Sanger sequencing. The cSNAIL genome vector (pAAV-Ef1a-DIO-SUN1GFP-WPRE-pA) is shown in FIG. 5A.

AAV Production.

The AAV was produced by triple co-transfection of pAAV-Ef1a-DIO-SUN1GFP-WPRE-pA, an AAV helper plasmid, and pUCmini-iCAP-PHP.eB into AAVpro® 293T cells (Takara Bio USA, Inc., Mountain View, CA; cat #632273). pUCmini-iCAP-PHP.eB was obtained from Viviana Gradinaru (http://n2t.net/addgene:103005; RRID: Addgene 103005) (Chan et al., supra). After cell expansion, the AAV particles were precipitated with polyethylene glycol (PEG) and purified with ultracentrifugation on an iodixanol gradient. The virus was titrated using the AAVpro® Titration Kit (Takara, cat #6233), diluted in PBS to a concentration of $8.0 \times 10^9$ vg/μl, and stored at −80° until injection.

Animals.

All molecular experiments were performed on Pvalb-2A-Cre mice (B6.Cg-Pvalb$^{tm1.1(cre)Aibs}$/J; The Jackson Laboratory, Bar Harbor, ME, stock no: 012358) (Madisen et al., *Nat Neurosci* 13:133-140, 2010). Imaging experiments for the validation of cSNAIL (FIGS. 6A-6C) were performed with double-transgenic Pvalb-2A-Cre and Ai14 mice (Ai14 strain; B6.Cg-Gt(ROSA)26Sor$^{tm14(CAG-tdTomato)Hze}$/J; Jackson Stock No: 007914)(Madisen et al., supra). Experiments related to Hif2a staining (FIG. 9D) were conducted on wild type mice (C57BL/6J: Jackson Stock No: 000664).

AAV delivery.

Mice were anesthetized with isoflurane for 2-5 minutes until breathing slowed and the animal had no pedal reflex. AAV ($4 \times 10^{10}$ vg) was injected into the retro-orbital cavity. The mice received 0.5% Proparacaine Hydrochloride Ophthalmic Solution for comfort and were monitored for physical and behavioral abnormalities post-procedure, but no such abnormalities were observed. The virus incubated for 21 to 28 days to reach peak expression before downstream experiments.

Dopamine Depletion Surgery.

The molecular experiments were designed to reproduce previous conditions and maximize cell yield. Therefore, bilateral acute 6-OHDA or saline injections were administered to the medial forebrain bundle as described elsewhere (Mastro et al., *Nat Neurosci* 20:815-823, 2017).

Immunofluorescence Staining and Imaging.

Wherever possible, tissue for imaging was preserved by 4% paraformaldehyde (PFA) perfusion. The brains were dissected and incubated overnight at 4° C. in 4% PFA. Shortly after, they were sectioned coronally with a vibratome at 100 μm for antibody staining and slide mounting. To visualize cSNAIL specificity (FIG. 6B-6D) tissues were stained with primary anti-NeuN (Cell Signaling Technology, Danvers, MA: #12943) and secondary Alexafluor 405 (Invitrogen, Waltham, MA; #A-31556) to label neurons. For images related to FIG. 9D, tissues were stained with primary anti-Pvalb (Swant, PV 27) paired with secondary Alexafluor 405 (Invitrogen, #A-31556) or Alexafluor 488 (Cell Signaling Technology, #4408S) and primary anti-Hif2a (Novus Biologicals, Centennial, CO; #NB100-132) paired with secondary Alexafluor 594 (Cell Signaling Technology, #8890S). For tissues involved in both genomic assays and imaging, one fresh coronal slice including caudate putamen, but anterior to the GPe, was fixed in 4% PFA for 24 hours. Tissues were stained with primary anti-tyrosine hydroxylase (Pelfreez, Rogers, AR; #P40101-150) and secondary Alexafluor 647 (Invitrogen, #A-31573) to assess dopamine levels in the striatum. All imaging sections were mounted onto slides using ProLong Diamond Antifade mounting media (Life Technologies Corp., Rockville, MD; #P36961) and imaged with confocal microscopy.

Image Analysis.

Single-channel and co-labeled cells were manually counted for FIGS. 6A-6C and FIG. 9D. To quantify the levels of tyrosine hydroxylase as a proxy for dopamine depletion, mean pixel intensity was measured with Fiji (Schindelin et al., *Nat Methods* 9:676-682, 2019). Measurements were performed on one 500×500 μm square from the striatum of each hemisphere.

Nuclei Collection.

Fresh mouse brain tissue was sliced on a vibratome in cold, oxygenated artificial cerebrospinal fluid. Brain regions of interest were then dissected under a light microscope and transferred into cold ATAC-seq lysis buffer (Buenrostro et al. 2015, supra). The nuclei were extracted from each tissue using 30 strokes of loose pestle dounce homogenization, followed by 70 μm filtration and one centrifugation wash for 10 minutes at 2000×g.

Affinity Purification of SUN1GFP+ Nuclei.

The nuclei suspension was pre-cleared for 10-15 minutes with Protein G Dynabeads (Thermo Fisher Scientific, Waltham, MA; cat. 10004D) to remove nuclei or debris that had native affinity for the beads. Free nuclei were incubated with anti-GFP antibody (Invitrogen, #G10362) for 30 minutes before fresh beads were added to the reaction and incubated for another 20 minutes. All incubations took place at 4° C. with 40 rpm end-to-end rotation. After this process, the bead-bound nuclei (SUN1GFP+ fraction) were purified and washed on a magnet, while the unbound nuclei were spun down and resuspended in water to preserve the SUN1GFP-fraction.

RNA-Seq Library Construction.

After setting aside 50.000 nuclei for ATAC-seq, total RNA was extracted from all remaining nuclei in each sample using the QIAGEN RNEASY® Micro Kit. (QIAGEN, Germantown, MD). Total RNA (10 pg to 10 ng per sample) was processed using the OVATION® SoLo RNA-seq System with mouse AnyDepletc® (Tecan, Redwood City, CA; cat. 0501-32) to remove ribosomal RNA. Because many nuclear transcripts are immature, no polyA selection was performed. Libraries were paired-end sequenced at 3-9 million reads per sample on the NEXTSEQ™ 500 System (Illumina, Inc., San Diego, CA).

RNA-seq Processing.

The sequencing output files were mapped to the mm10 mouse genome assembly using Hisat2 and sorted. Duplicate UMIs were removed using NuDup (online at github.com/tecangenomics/nudup). The quality of the filtered data was assessed using Picard CollectRnaSeqMetrics (online at broadinstitute.github.io/picard). A counts per gene per sample matrix was constructed using Rsubread featureCounts (Liao and Smyth. *Nucleic Acids Res* 47:e47, 2019) for input into DESeq2 (Love et al., supra).

ATAC-Seq Library Construction.

A small subset of nuclei was stained with DAPI and fluorescent nuclei were manually counted using a hemocytometer. About 50,000 nuclei were transferred to a new tube in 22.5 μl water and mixed with 2.5 μl Tagment DNA Enzyme I and 25 μl Tagment DNA Buffer (Illumina, cat. 20034198). The tn5 transposition reaction was carried out at 37° C., 300 rpm for 30 minutes. After tagmentation, the samples were taken through column purification, amplification, and double-sided size selection (100-1000 bp) with AmpureXP beads (Beckman Coulter, Indianapolis, IN; cat. A63881). To reduce amplification bias, a side qPCR reaction was evaluated for each sample to determine the optimal number of PCR cycles for each sample to reach ⅓ maximum intensity. The samples were pooled and paired-end sequenced on a Novaseq 6000 (Illumina) to about 25 million unique, non-mitochondrial reads per sample.

ATAC-Seq Processing.

The fastq files from each sample were processed with the ENCODE ATAC-seq pipeline (online at github.com/kundajelab/atac_dnase_pipelines). Peaks were called on biological replicates of the same cell type, brain region, and treatment with an Irreproducible Discovery Rate (IDR) threshold 0.1 (github.com/kundajelab/idr; Li et al., *Annals Appl Stat* 5(3):1752-1779, 2011). The merged union of IDR peaks of the relevant cell populations were evaluated for differential accessibility using DESeq2 (Love et al., supra), where the reads per peak for each sample were quantified using Rsubread featureCounts (Liao and Smyth, supra) on the filtered bam alignments. For analysis of cellular identity (FIGS. 7A-7C and 8A-8F), the regions tested were the union of IDR peaks from all sham animal samples. For FIG. 8E, instead of ATAC-seq peaks, counts were computed over 10 kb windows around the transcription start sites for all genes assessed in the RNA-seq analysis. For assessment of DD-affected regions (FIG. 10), six separate count tables were constructed for the six cell populations and represented the union of IDR peaks from sham and DD animals for the given cell type and brain region.

snATAC-Seq and snRNA-Seq Processing.

Figure 7A:
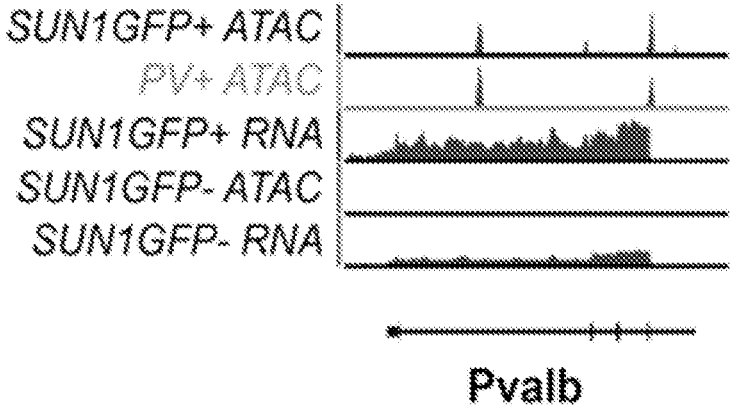
FIGS. 7A-7C show that cSNAIL-isolated nuclei from Pvalb-2A-Cre mice recapitulate PV+ transcriptomic and epigenomic signals from external data.
Figure 7B:
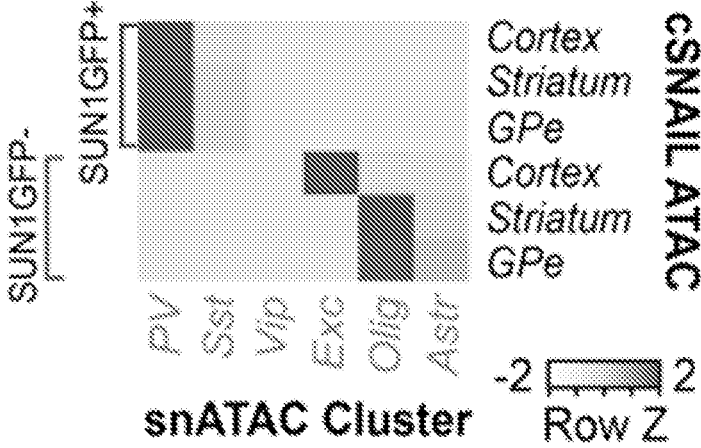

To compare cSNAIL-isolated cell types with single nucleus sequencing data, two publicly available datasets from adult mouse cortex were reprocessed. 10× snATAC-seq data was downloaded and processed following the Signac vignette for the purposes of FIG. 7B (online at github.com/timoast/signac). For the snRNA-seq comparison, raw count matrices derived from 10× chromium v3 experiments conducted in primary motor cortex were downloaded from NEMO (portal.nemoarchive.org). The sample meta data is provided online at drive.google.com/open?id=1uDeGI-IPZoiX4aYGNZIWFcGWjaNqTHCd. Empty droplets were removed using the DropletUtils package (Griffiths et al., *Nat Commun* 9:2667, 2018) defaultDrops method. Doublets were predicted and removed using the SCDS package (Bais et al., *Bioinformatics* 36:1150-1158, 2019) cxds_bcds_hybrid method with score cutoff of 1.0. The UMI count values were normalized using pooled size factor normalization (Lun et al., *Genome Biol* 17:75, 2016) implemented in the Scran package (Lun et al., *F1000 Res* 5:2122, 2016). Size factor normalization requires a preclustering step which was computed using the Scanpy (Wolf et al., *Genome Biol* 19:15, 2018) package's Leiden community detection algorithm (Traag et al., *Sci Rep* 9:5233, 2018). To create the UMAP (Mcinnes et al., *arXiv* 1802.03426, 2018) for visualization the Scanpy package was also used. Principle components were computed on the top 7500 most variable genes. The UMAP was then computed based on the PCA reduced single nucleus gene expression matrix.

Experimental Design and Statistical Analysis.

The statistical methods used for the quantification of cSNAIL specificity and efficiency by imaging co-fluorescence are described in the description of FIG. 6A-6D. For molecular assessment of cSNAIL isolated cell fractions (FIGS. 7A-7C and 8A-8F), data were collected from two sham animals, one male and one female. Differentially expressed genes and differentially accessible ATAC-seq regions between SUN1GFP+ and SUN1GFP– samples in each brain region were assessed using the negative binomial model in DESeq2: read count=~sex+SUN1GFPstatus. To restrict DESeq2 dispersion estimates to the relevant samples, each model was built separately and only included the samples from one brain region.

For comparing cSNAIL ATAC-seq markers to snATAC-seq cluster markers (FIG. 7B), the hypergeometric enrichment test was used, sampling cell type-specific cSNAIL peaks in each brain region from an expected frequency of cluster-specific snATAC-seq peaks. Only the set of peaks present in both data (112,082) were evaluated. For simplicity, cluster-specific peaks from all excitatory neuron clusters were combined into one category. For visualization, the hypergeometric test enrichments were converted into a z-score for each cSNAIL cell population and plotted using gplots heatmap.2 in R (online at github.com/talgalili/gplots). Annotation enrichments were assessed in differential gene sets using g:Profiler (FIG. 8C) (Peterson et al., supra).

Differential motif enrichment analyses was performed with AME (McLeay and Bailey, supra), with peak sets of interest summit-centered and unified to 500 bp. Where more than one summit was called within a peak and these summits were more than 100 bp apart, both entries were included in the analysis. Enrichments were assessed relative to a background of all ATAC-seq peaks in that cell type or population.

Unless otherwise noted, molecular comparisons between DD and sham animals were conducted with data from two sham animals and four DD animals. Both treatment groups consisted of equal numbers of males and females. The three female animals were littermates at 12 weeks of age at endpoint and the three male animals were littermates 9 weeks of age, all from the same colony. Animals were euthanized consistently in the morning, 2-3 hours after the light cycle began. ATAC-seq and RNA-seq were performed on partitions of the same source pools of nuclei.

Sample similarities for RNA-seq and ATAC-seq were assessed by principal component analysis (PCA) and hierarchical clustering in DESeq2 (FIGS. 11A-11B, and 12A-12D). Because transcript levels are quantitative, the RNA-seq counts were modeled continuously according to the anti-TH imaging intensities of each animal, which reflect the extent of DD: DESeq2 read count=~sex+THintensity. To follow up on RNA-seq results related to Hif2a, image quantification was performed as noted in the description of FIGS. 10A-10C and related results. For DD-affected open chromatin analyses (FIG. 10A-10C), a binary model of treatment state (DD vs. saline) was used, controlling for sex differences: DESeq2 read count=~sex+treatment. Again, models for each cell population were built separately and only included samples for one comparison. DD-affected ATAC-seq peak sets were subjected to pathway enrichment analysis using GREAT version 3.0.0 (McLean et al., *Nat Biotechnol* 28:495-501, 2010) and motif enrichment using AME as described above.

Results cSNAIL Isolates Cre+ Nuclei with High Precision.

cSNAIL technology is a viral strategy for labeling and isolating the nuclei of Cre-expressing cells. The cSNAIL viral genome expresses a nuclear envelope anchored GFP fusion protein in a Cre-dependent manner. To achieve nuclei isolation compatible epigenomic profiling, a similar strategy to the SUN1GFP INTACT transgenic mouse strain (Mo et al., supra) was used. SUN1 is a highly conserved nuclear envelope protein that helps connect the nucleoskeleton and the cytoskeleton (Haque et al., supra). Because of its tight association with the inner nuclear envelope, the SUN1GFP fusion protein localizes the GFP protein on the nuclear surface. This positioning allows for affinity purification of nuclei, whereby after tissue is homogenized into a single-nuclei suspension, magnetic beads coated with anti-GFP antibody specifically bind SUN1GFP+ nuclei, thus separating them from SUN1GFP- nuclei. Several modifications to the INTACT mouse transgene design (described above) to package the cSNAIL SUN1GFP vector into AAV variant PHP.eB, which is capable of crossing the blood brain barrier to broadly transduce many cells in the central nervous system (Chan et al., supra).

Figure 6A:
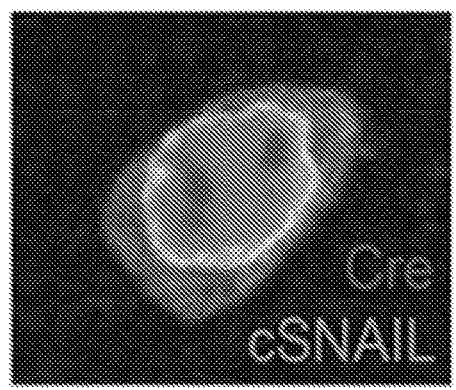
FIGS. 6A-6C show that cSNAIL targets Cre+ nuclei with high precision.
Figure 6B:
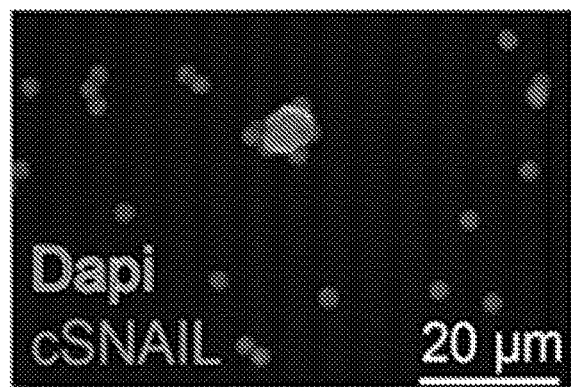
Figure 6C:
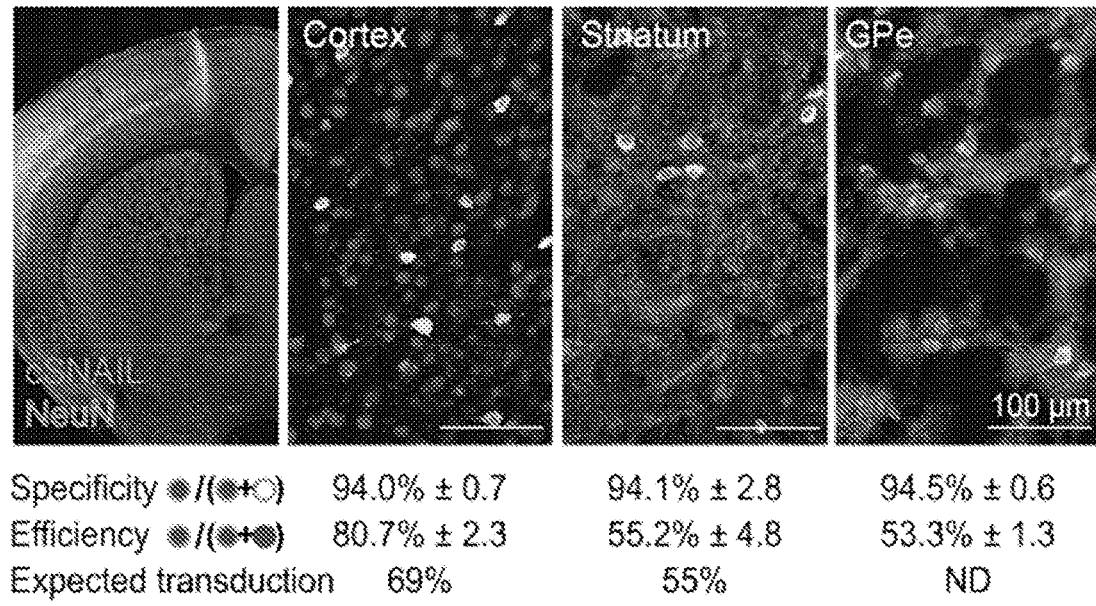

The ability of cSNAIL to drive Cre-specific nuclear anchored independent labeling in Pvalb-2A-Cre mouse lines was evaluated using imaging and molecular data (FIGS. 6A-6C and 7A-7C). Fluorescent imaging confirmed that cSNAIL promoted SUN1GFP expression that was properly localized to the nuclear envelope in tissue (FIG. 6A). The expression was sufficient to bind anti-GFP coated magnetic beads after tissue dissociation (FIG. 6B). To quantify the ability of cSNAIL to correctly target Cre+ cells, the expression of cSNAIL was compared to the expression of Cre reporter tdTomato of the Ai14 mouse strain (FIG. 6C). For the purposes of this analysis, virus specificity was defined as the percent of SUN1GFP+ cells that also expressed tdTomato, and virus efficiency was defined as the percent of tdTomato+ cells that also expressed SUN1GFP. cSNAIL exhibited very strong (>94%) specificity in the cortex, striatum, and GPe. The efficiency ranged from 53% to 81%, reflecting the expected transduction of the viral capsid in these brain regions (Chan et al., supra).

After affinity purification, bead-bound nuclei and free nuclei were counted using a manual hemocytometer on a fluorescent microscope to determine the purity and yield of cSNAIL nuclei isolation. Of the nuclei bound to beads, 97.18% had observable SUN1GFP expression. Based on the numbers of SUN1GFP+ nuclei in the bound and unbound fractions, it was estimated that the bound fraction captured up to 65% of the total SUN1GFP+ nuclei. These results demonstrated that nuclei isolation with cSNAIL was as good as SUN1GFP nuclei affinity purification using transgenic expression.

To confirm the molecular identity of the cSNAIL-isolated nuclei from Pvalb-2A-Cre mice, ATAC-seq and RNA-seq from sham animal SUN1GFP+ and SUN1GFP-fractions were compared to publicly available PV+ and PV- data. cSNAIL ATAC-seq and RNA-seq exhibited the expected cell type-specific patterns at the Pvalb locus compared with signals from INTACT-isolated populations (Mo et al., supra) (FIG. 7A). When comparing the identified cell type-specific ATAC-seq markers to single nucleus (sn)ATAC-seq clusters from the adult mouse cortex (github.com/timoast/signac), the SUN1GFP+ peaks from each brain region were enriched for PV+ cluster markers (FIG. 7B). Aligning with the expected cell type proportions in each brain region, SUN1GFP-fractions were most enriched for snATAC-seq markers of excitatory neuron clusters (cortex only) and glial clusters.

Figure 7C:
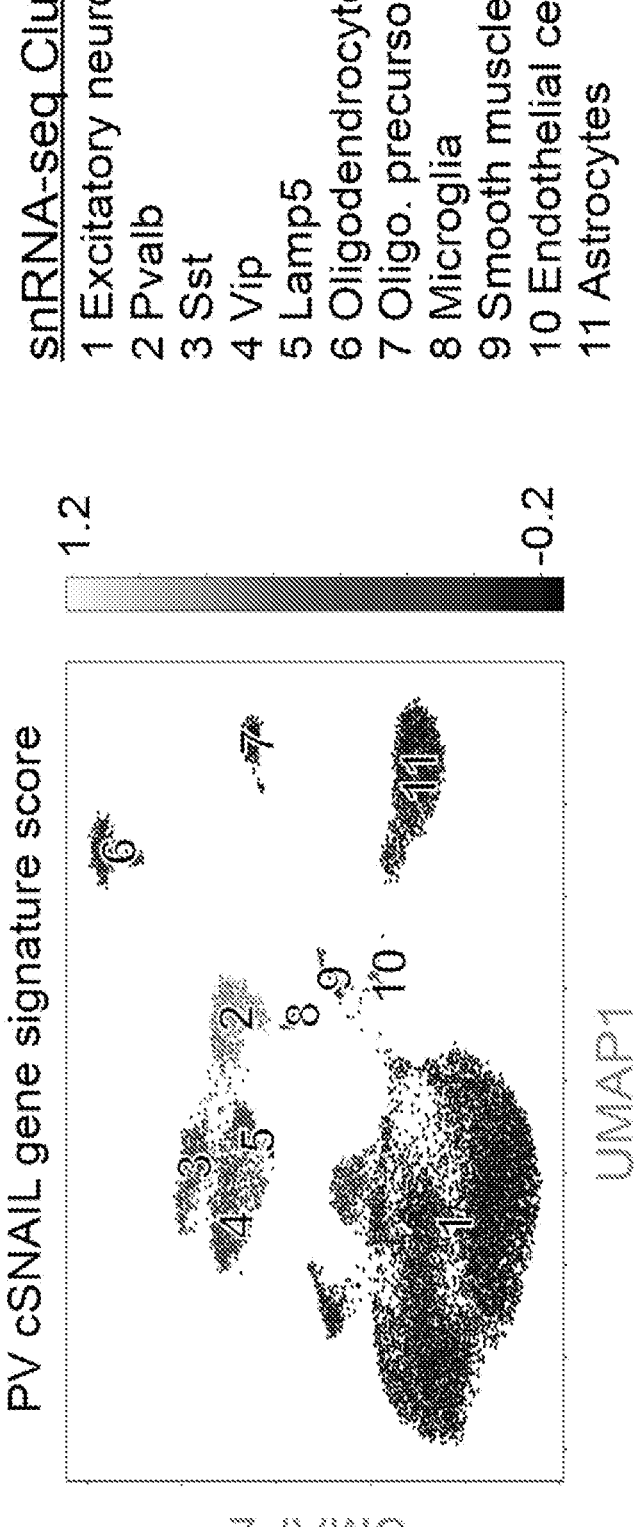
Figures 13A, 13B:
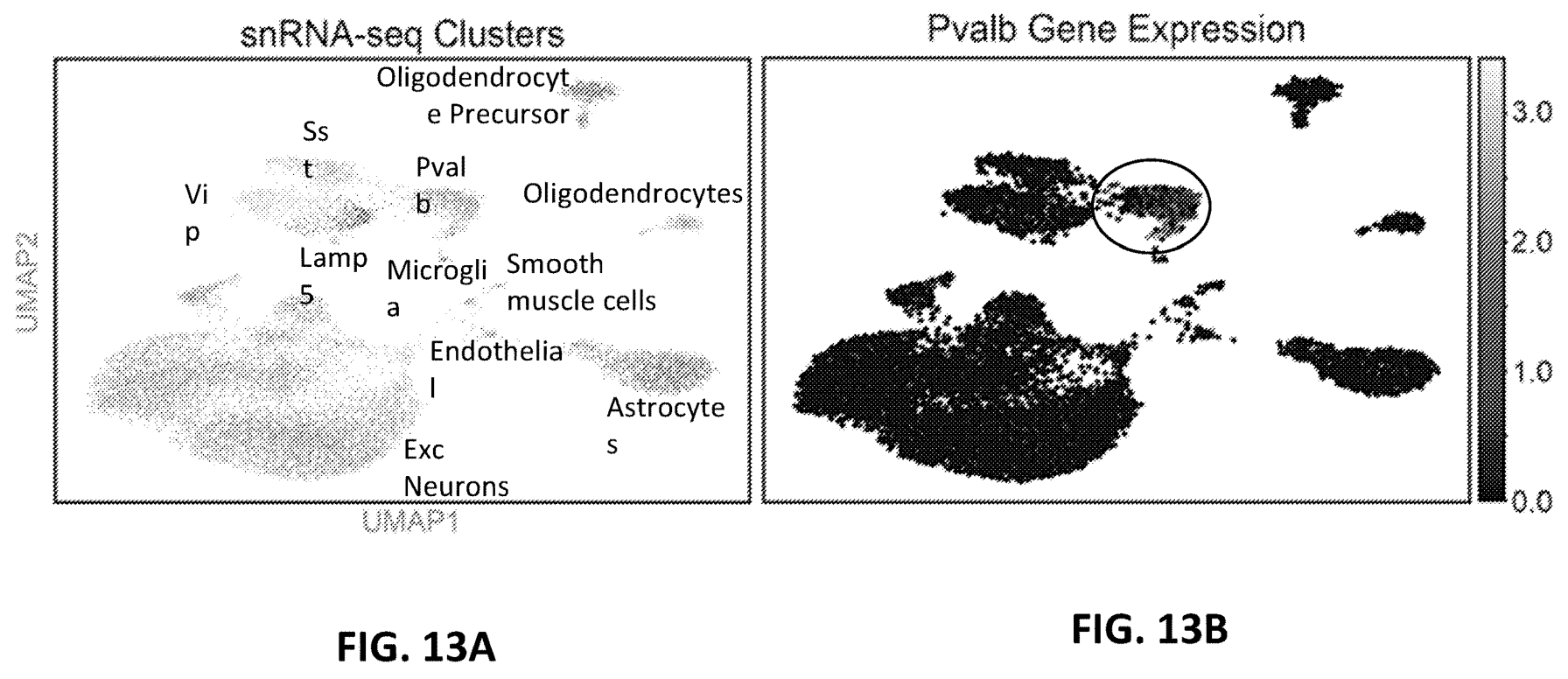

Comparison of cSNAIL RNA-seq in Pvalb-2A-Cre mice with mouse cortex snRNA-seq further corroborated the desired enrichment. For this analysis, cSNAIL SUN1GFP+ and cSNAIL SUN1GFP- gene expression signatures (i.e., strongly differentially expressed genes) were defined in the cortex. snRNA-seq cells were then assessed for similar expression patterns by scoring their expression of the cSNAIL SUN1GFP+ gene signature (FIGS. 7C, 13A, and 13B). The SUN1GFP+ scores were computed by averaging across the scaled (0 mean centered, unit variance) expression of signature genes across all cells. As expected, cells in the PV+ interneuron cluster (circled in FIG. 13B) had the strongest expression of the cSNAIL SUN1GFP+ gene signature, followed by other interneuron clusters. These comparisons provided evidence that cSNAIL SUN1GFP+ samples are indeed strongly enriched for PV+ neurons. Therefore, throughout the remainder of this Example, cSNAIL SUN1GFP+ and SUN1GFP- cells are referred to as PV+ and PV- cells, respectively.

Molecular Signatures of cSNAIL-Isolated PV+ and PV- Cells.

Figures 14A, 14B:
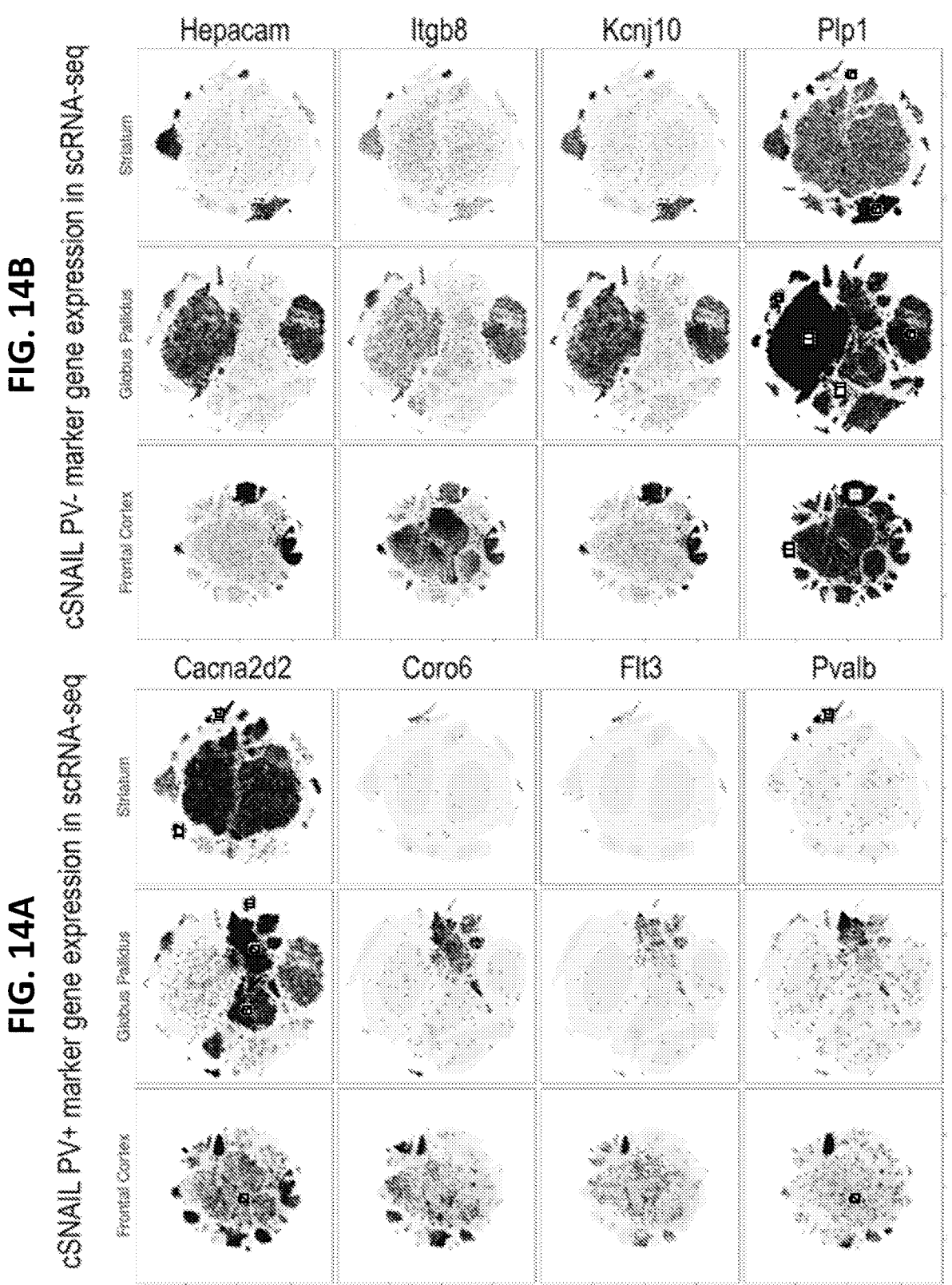
FIGS. 14A and 14B show that PV+ and PV− marker genes from cSNAIL were expressed in relevant cell clusters from scRNA-seq. DropViz was used to define scRNA-seq clusters in the frontal cortex, striatum, and globus pallidus. Per cell expression of each indicated gene is shown by the size of the points. Where meta-cell expression of a gene was greater than 70% of the maximum expression in that meta-cell, the cluster is labeled by its cluster number.

In each brain region, hundreds of differentially expressed genes and thousands of differentially accessible ATAC-seq regions were recovered between PV+ and PV- cell populations (FIGS. 8A-8F). 35 PV+ and 29 PV- marker genes with high specificity (DESeq2 $p_{adj}<0.01$ and $|LFC|>1$) across all three tissues were defined. Of these genes, a small number also had corresponding cell type-specific chromatin accessibility within a 10 kb window around the gene transcription start site, including those highlighted in FIGS. 8B and 8E. The PV+ marker genes Coro6, Flt3, and Cacna2d2 also tended to be restricted to PV+ clusters in DropViz snRNA-seq from the mouse cortex, striatum, and globus pallidus, although Cacna2d2 also was prevalent in Chat neurons (FIG. 14A)(Saunders et al., *Cell* 174:1015-1030.e16, 2018). This further demonstrated that cSNAIL enrichment for PV+ neurons was generalized to brain regions outside the cortex. PV- gene expression signatures that were consistent across all three brain regions appeared to be dominated by glial cells, especially oligodendrocytes (e.g., Hepacam and Kcnj10) (FIG. 14B). This was not surprising given that neuron composition varies greatly between the cortex, striatum, and GPe. Functional gene enrichment on pan-PV+ and pan-PV- differential genes was consistent with these observations, implicating neuron-related pathways among PV+ genes and glial pathways among PV- genes (FIG. 8C).

Next, studies were conducted to identify transcription factor binding motifs that might play a role in epigenetically defining PV+ neurons, by testing for enriched motifs in sequences underlying PV+ and PV- specific ATAC-seq peaks in each brain region (FIG. 8F). Among the most significantly enriched PV+ motifs in all three brain regions was Tcef3, which was previously implicated in PV+ neuron-specific gene regulation (Mo et al., supra). Additionally, consistent PV+ enrichment for the Esrrg and Hoxa2 motifs was observed. The Esrrg transcript itself also was upregulated in PV+ neurons in all three brain regions ($p_{adj}<0.001$), but Tcef3 or Hoxa2 were not. Consistent PV- motif enrichments across all brain regions included the motif for Sox10, which is necessary for the differentiation and survival of oligodendrocytes (Pozniak et al., *Proc Natl Acad Sci USA* 107:21795-21800, 2010; and Takada et al., *Glia* 58:996-1006, 2010). There also were significant enrichments for many other Sox family motifs and the Meis1 motif among PV- ATAC-seq sequences. The representation of glial signatures among PV- cell ATAC-seq and RNA-seq indicates that the nuclei dissociation during cSNAIL affinity purification was not restricted to neurons.

Gene Expression Differences in Dopamine Depleted Animals.

Figures 11A, 11B:
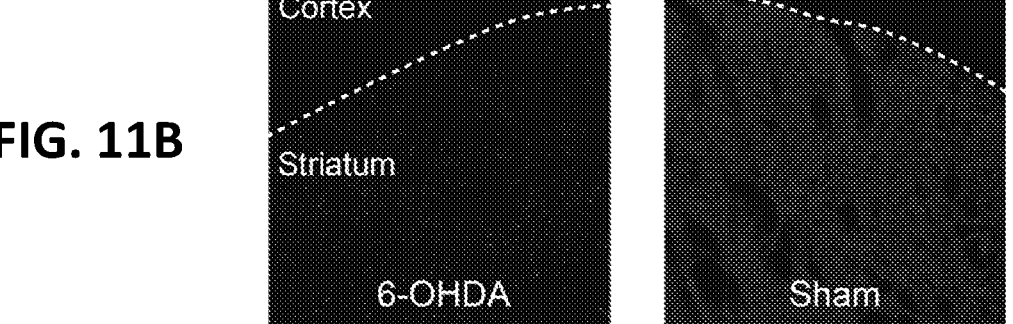
FIGS. 11A-11B show the quantification of dopamine depletion per hemisphere.
Figures 15A, 15B:
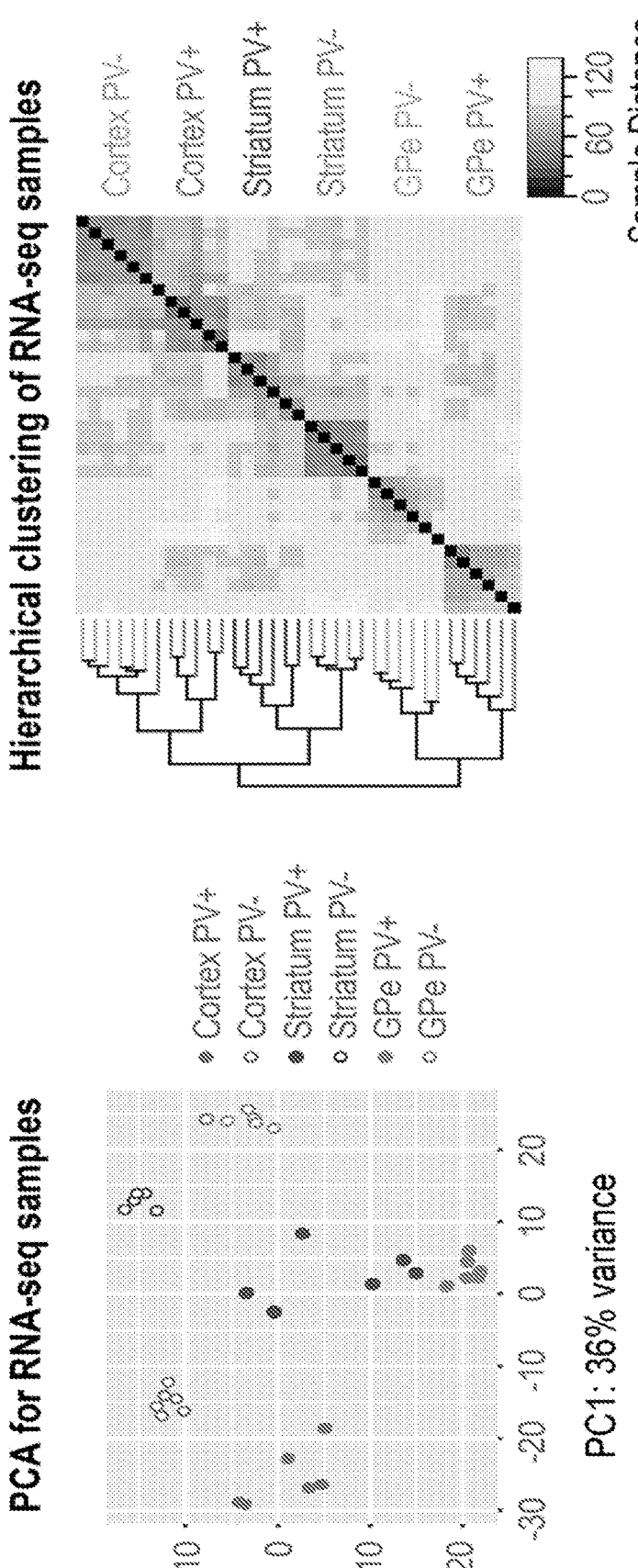
FIGS. 15A and 15B show RNA-seq sample similarities.

Striatal tissue from 6-OHDA lesioned animals had significantly lower levels of dopamine production enzyme tyrosine hydroxylase than sham animals, indicating successful depletions (FIGS. 11A-11B). All depletions were bilateral except in one animal, DD2, where one hemisphere was only weakly depleted. The RNA-seq data was high quality for all samples except one striatum PV- sample from a DD animal, which was excluded from the analysis. Samples were separated by tissue and cell type in PCA and hierarchical clustering, indicating higher variability between cell types than between biological replicates (FIGS. 15A and 15B).

Figure 9B:
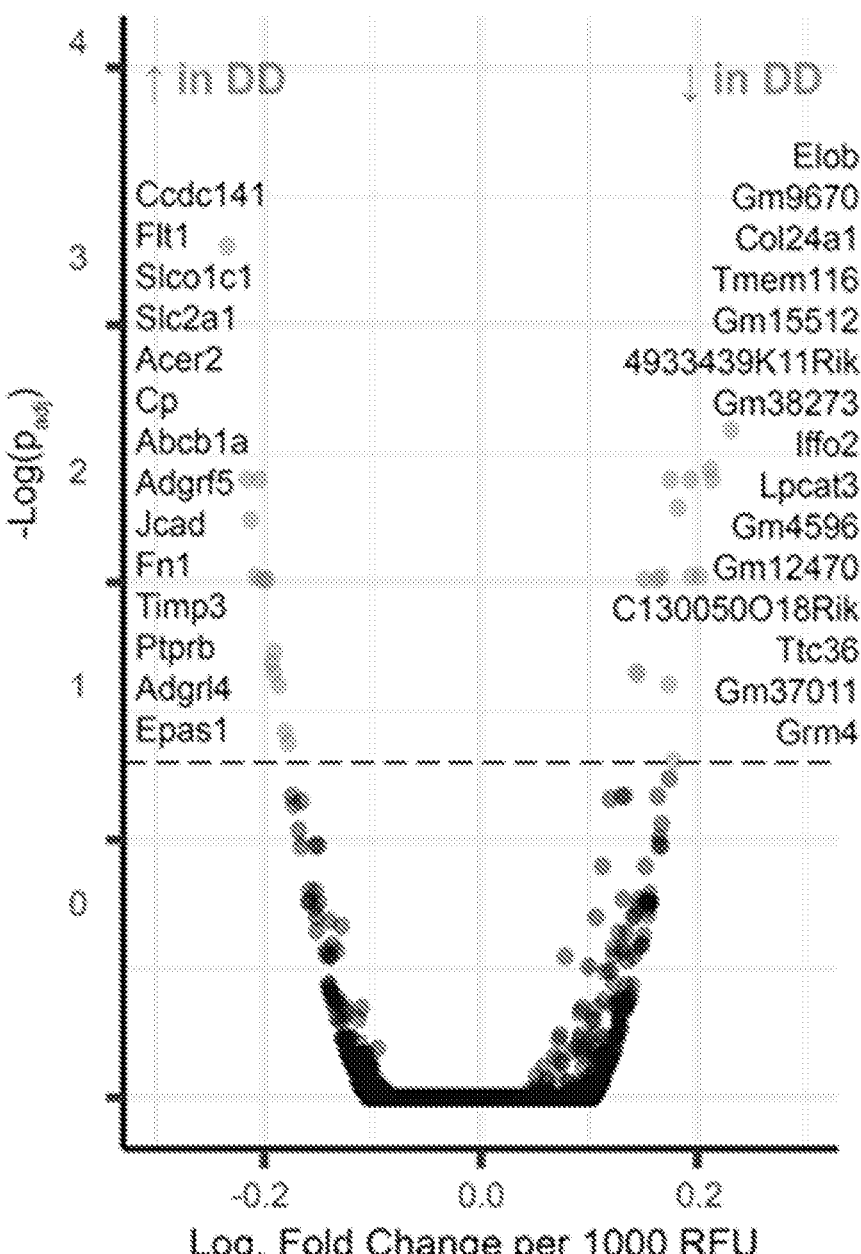
Figure 9D:
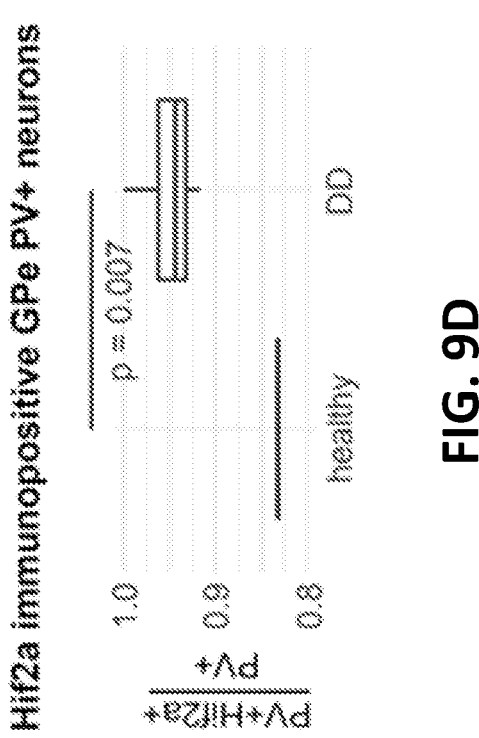
Figure 9C:
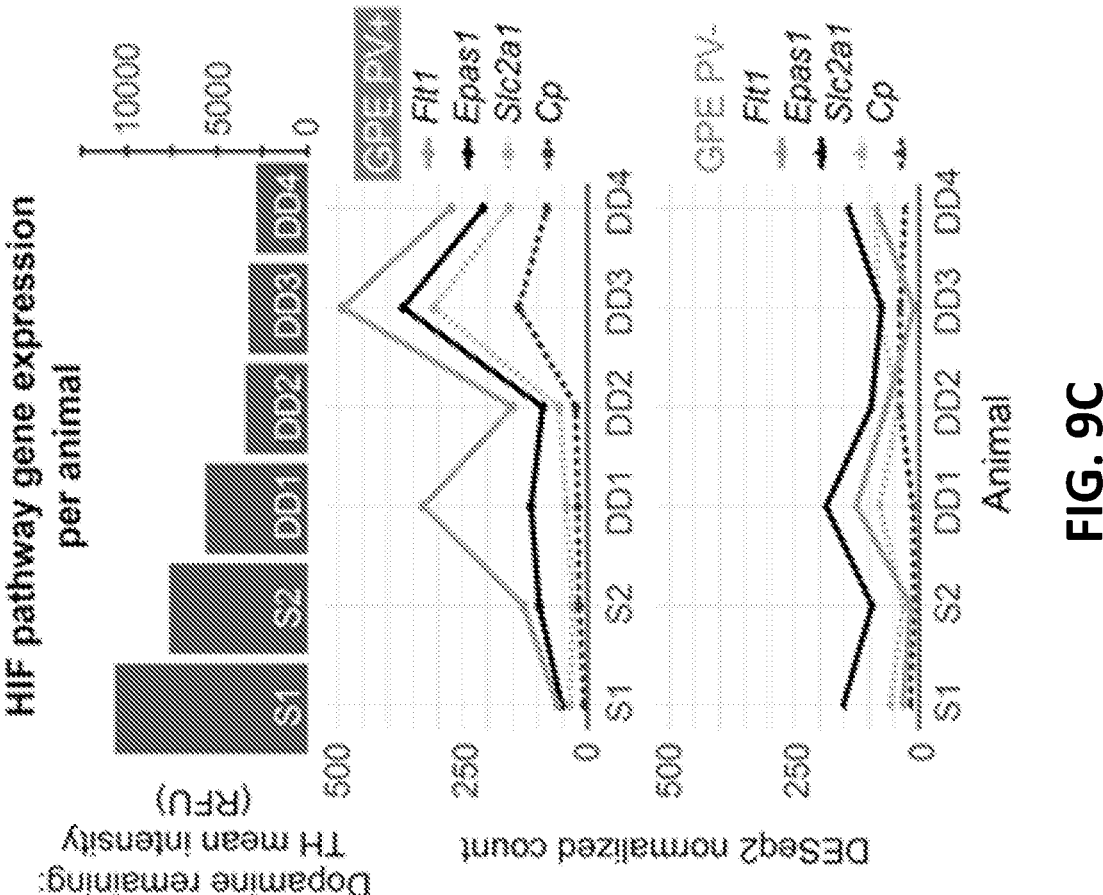

In the RNA-seq data from DD and sham animals, very few significant DD-affected genes were recovered in any cortical cell types, striatal cell types, or the GPe PV-population. In contrast. GPe PV+ neurons contained 29 differentially expressed genes in DD ($p_{adj}$<0.05) (FIGS. 9A and 9B). It was readily apparent that there were many genes involved in cellular oxygen homeostasis and neuroprotection among the fourteen genes that were upregulated in the GPe PV+ neurons of DD animals. These included Epas1, which encodes for Hypoxia-inducible factor 2 alpha (transcription factor Hif2a), and three of its targets: Cp, Slc2a1, and Flt1 (Schofield and Ratcliffe, *Nat Rev Mol* 5:343-354, 2004; Dengler et al., *Crit Rev Biochem Mol Biol* 49:1-15, 2015; and Smeyne et al., *Neurosci* 295:23-38, 2015)(FIG. 9C). The downregulated set also included Elob, a moderator of free oxygen sensing that inhibits Hif2a (Ohh et al., *Nat Cell Biol* 2:423-427, 2000). These results suggested that GPe PV+ neurons may react to DD through hypoxia-inducible factor (HIF) signaling and associated transcriptional response.

Figure 16:
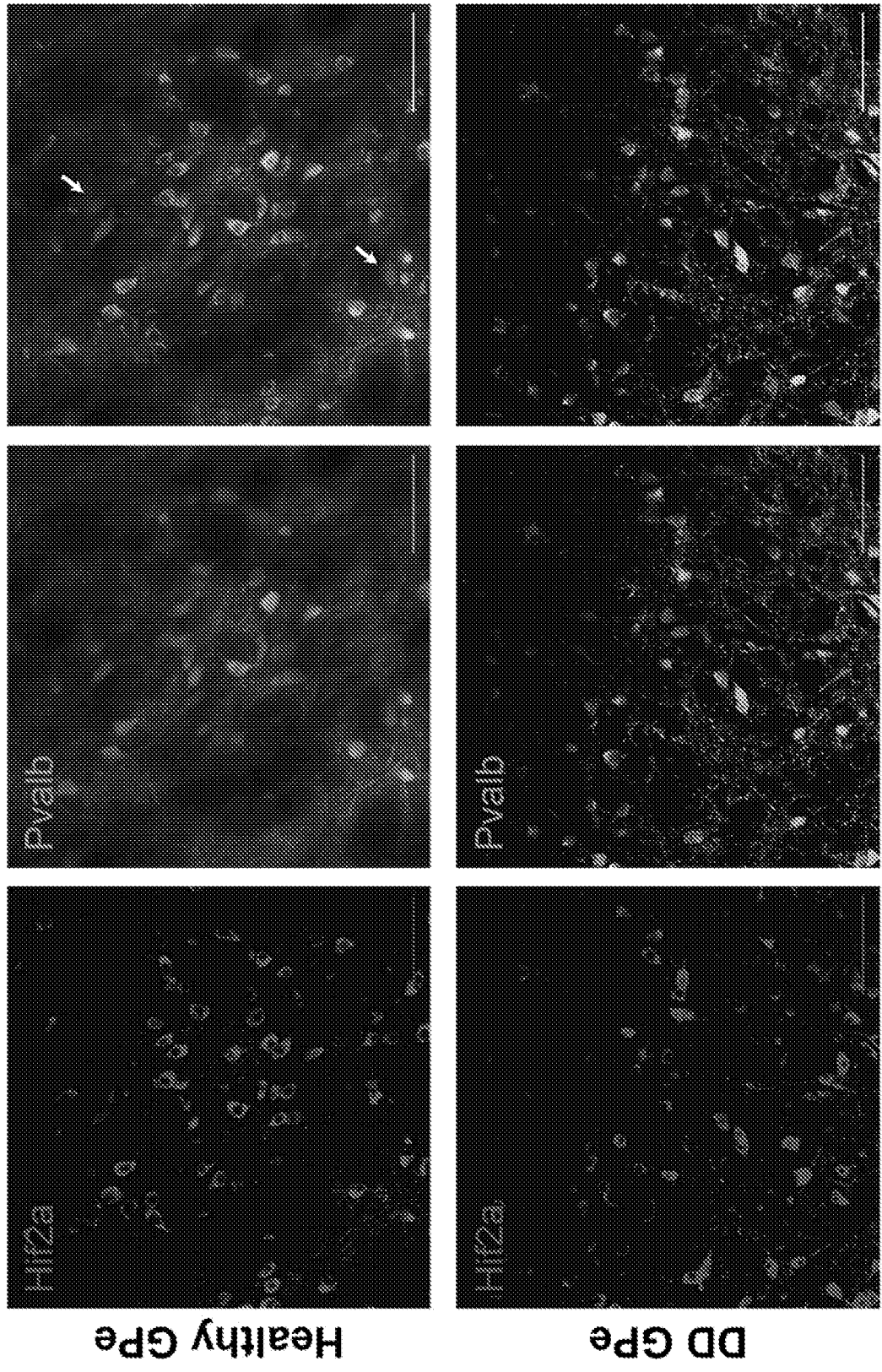
FIG. 16 is a series of images showing that with dopamine depletion, the proportion of GPe PV+ neurons that express Hif2a protein increases. Example images from healthy and DD GPe tissue are shown. Some instances of PV+Hif2a− cells are highlighted by white arrows. The scale bars measure 100 μm.

To see whether increased Epas1 transcription in GPe PV+ neurons was accompanied by increased Hif2a protein levels, double immuno-fluorescent staining for Pvalb and Hif2a was performed in healthy and DD mouse tissue. Indeed, a higher proportion of GPe PV+ neurons expressed Hif2a in images from DD animals compared with healthy animals (FIGS. 9D and 16). The change in mean proportion was 11.3% and this difference was significant (t-test, p=0.007).

Other differentially expressed genes in the GPe PV+ neurons of DD mice have also been implicated in processes of neurodegeneration and/or neuroprotection. For example, overexpression of Timp3, a key inhibitor of matrix metalloproteinases that contribute to dopaminergic neuron apoptosis in PD (Kim et al., *FASEB J* 21:179-187, 2007), was observed. Timp3 expression in neurons is protective against blood-brain barrier damage, but high levels of Timp3 can lead to cell death (Rosenberg, *Lancet Neurol* 8:205-216, 2009). Lpcat3, a gene found to have reduced expression in GPe PV+ neurons upon DD, is necessary for ferroptosis, which has been linked to neurodegeneration in PD and Alzheimer's disease (Angeli et al., *Cell* 171:273-285, 2017). Due to the small number of regulated genes, functional enrichment for specific pathways was low.

Open Chromatin Differences in Dopamine Depleted Animals.

Figures 10A, 10B, 10C:
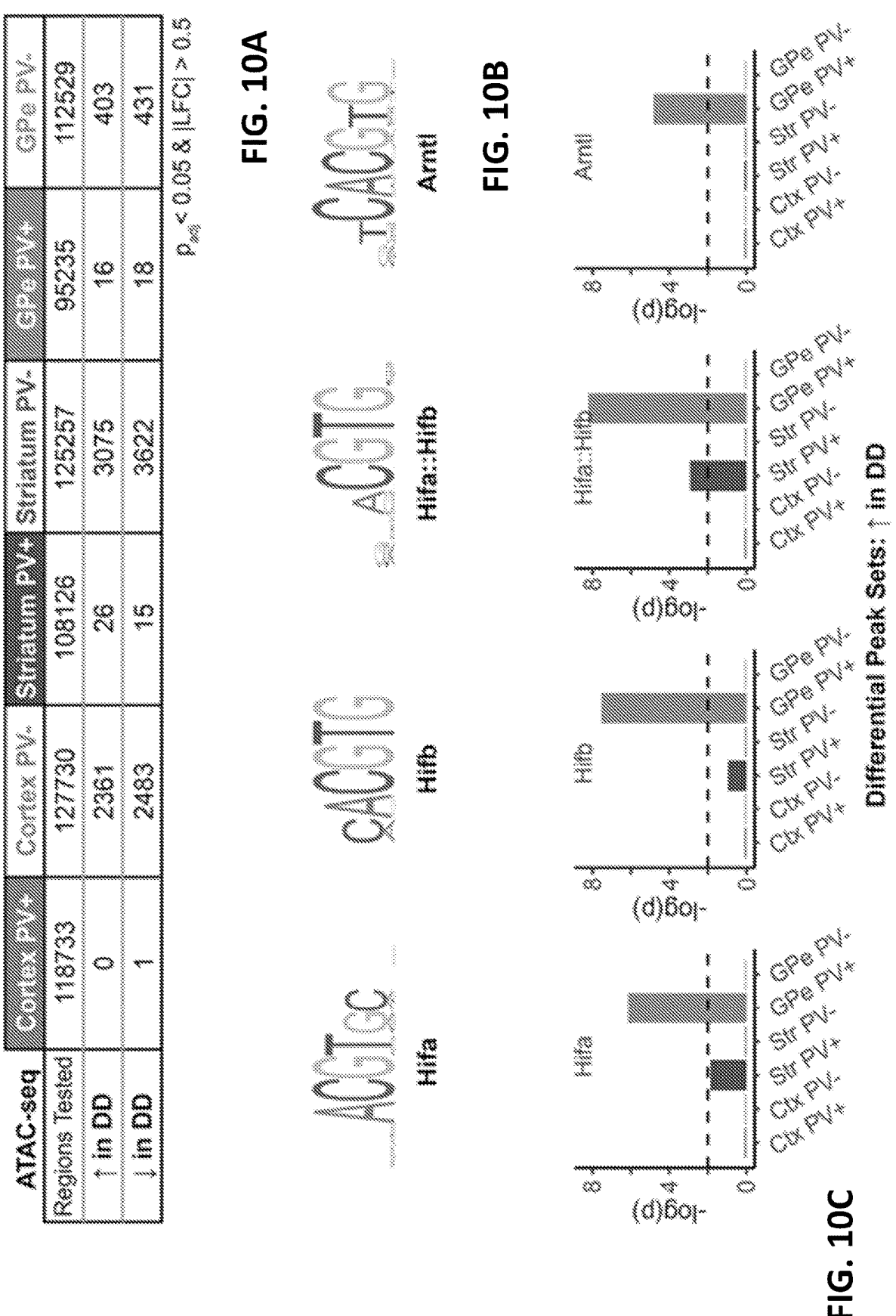
FIGS. 10A-10C show that open chromatin changes associated with DD showed cell type-specific HIF motif enrichment.
Figure 17:
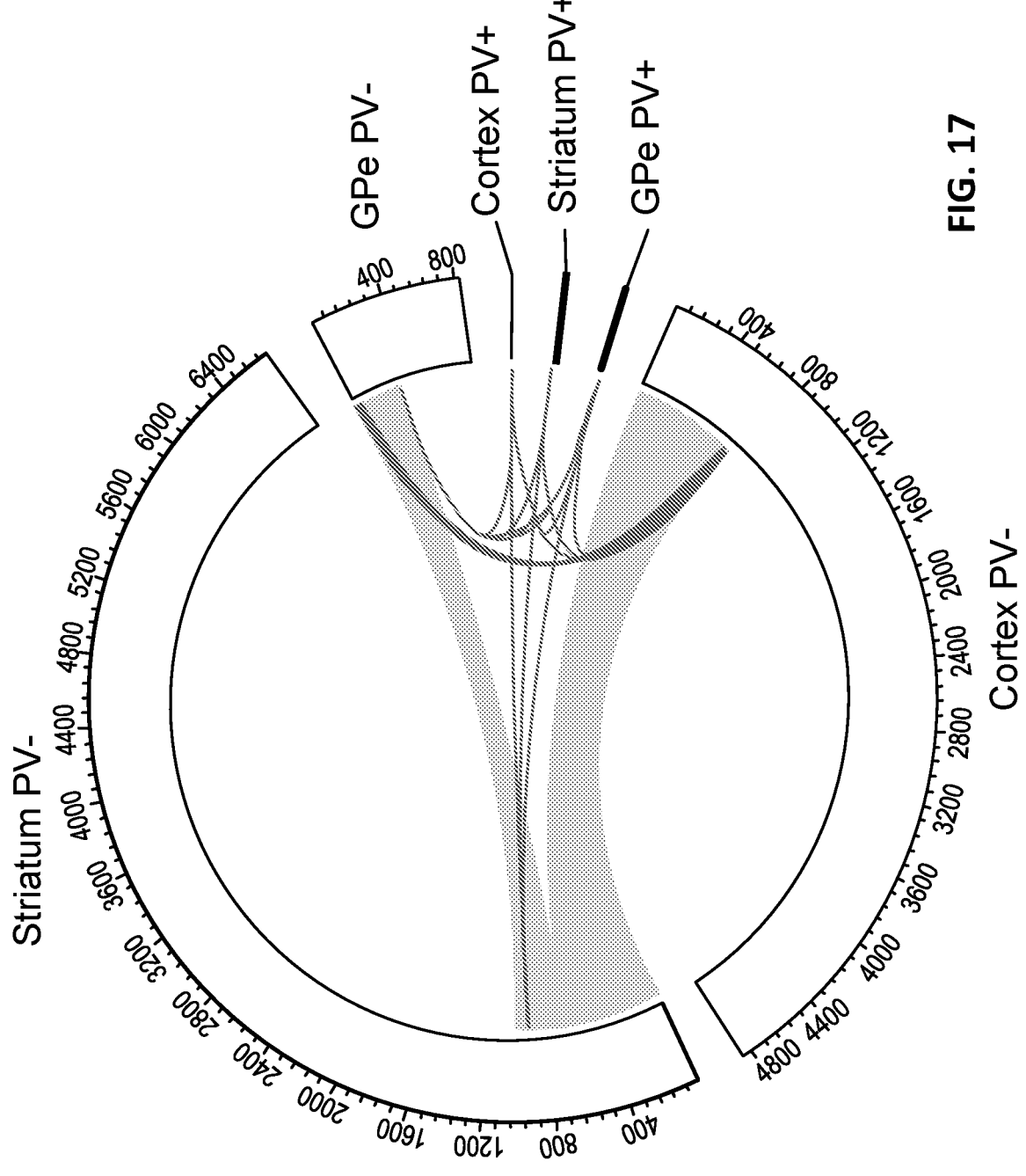
FIG. 17 shows the overlap between DD-affected ATAC-seq peaks of different cell types. The width of each outer segment of the circle shows how many DD-affected peaks were recovered in that cell type. Bidirectional arcs between two cell types signify shared DD-affected peaks where the width of the connection represents the number of shared peaks. The data were plotted with circlize (Gu et al., *Bioinformatics* 30:2811-2812, 2014).
Figure 18:
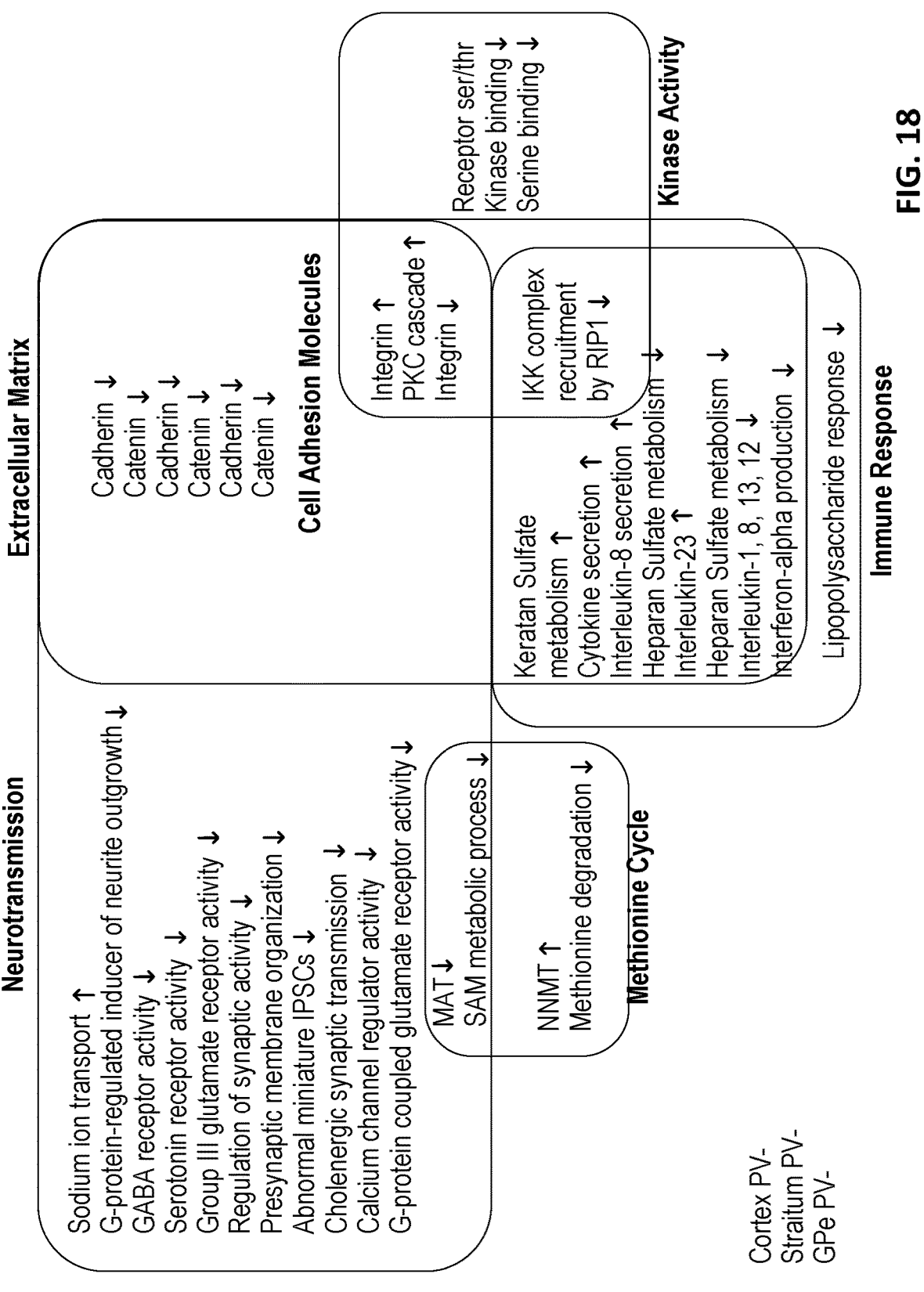
FIG. 18 is a summary of enriched annotations in DD-affected ATAC-seq peak sets. Enrichments were determined using GREAT for each differential set of peaks against a background of all peaks in that cell type. The arrow of a term indicates that it was enriched in DD-increasing peaks (up arrow) or DD-decreasing peaks (down arrow).

Based on standard QC metrics (see above), the ATAC-seq data was high quality for all samples except one cortex PV+ sample from a DD animal, which was excluded from the analysis (FIGS. 12A-12D). In DD animals, a small number of confident open chromatin changes were observed in PV+ cell types, and many changes were observed within PV− cell types that met significance at a cutoff of $p_{adj}$<0.05 (FIG. 10A). The DD-affected open chromatin regions in different cell types had some redundancy, but the majority were cell type-specific at the level of the individual regulatory element (FIG. 17). However, DD-affected regions in multiple cell types tended to converge around areas of the genome enriched for certain functions including neurotransmission, immune response, and the methionine cycle (FIG. 18).

Figure 19:
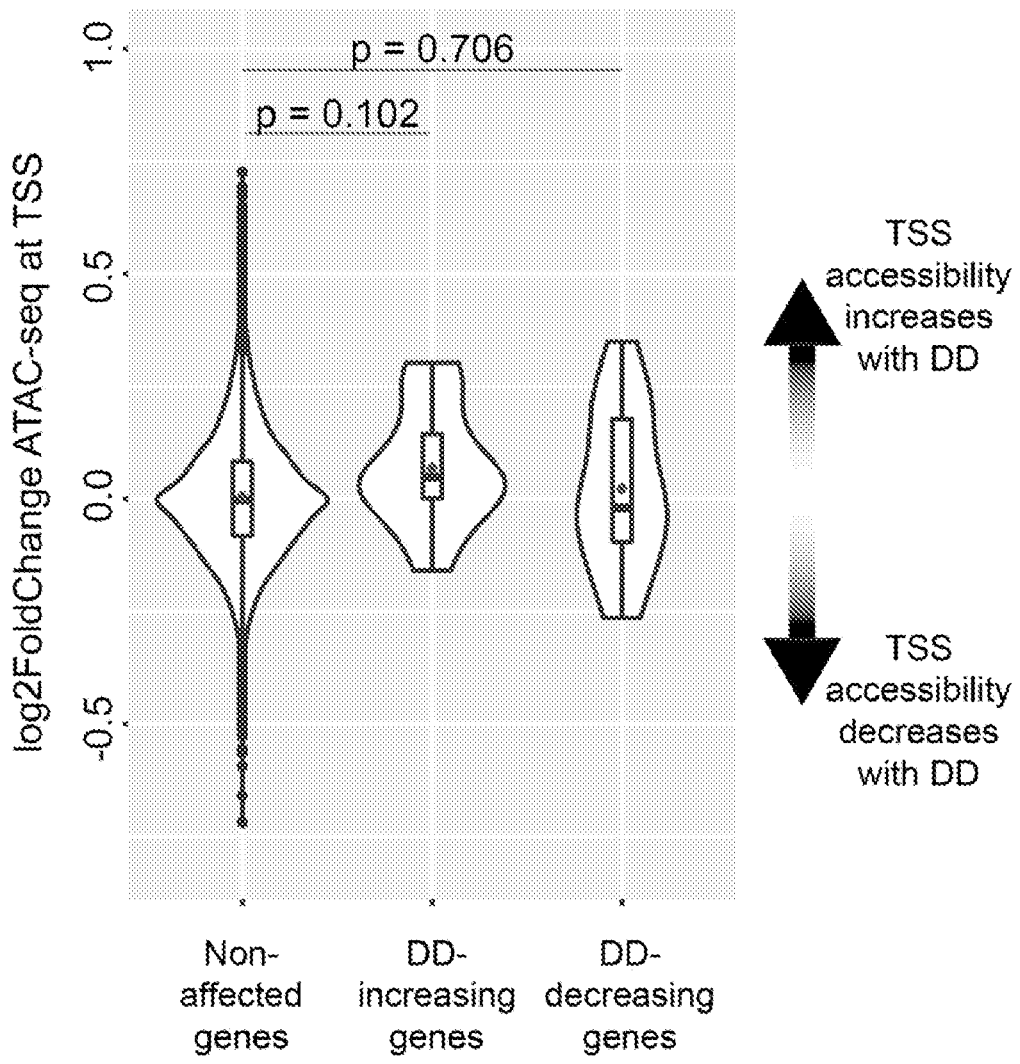
FIG. 19 is a graph plotting TSS accessibility trends with differential gene expression in GPe PV+ neurons (t-test).

Further studies were conducted to assess whether the observed differences in open chromatin could be responsible for the transcriptional differences observed in the GPe PV+ population. Genes with increased expression in DD had higher levels of open chromatin nearby (hypergeometric p=0.0003), while genes that decreased in expression had lower levels (hypergeometric p=0.002) (FIG. 19). However, there were no overlaps in the most significantly differential genes and peaks.

Due to the increased expression of HIF-related transcripts in GPe PV+ neurons in DD, it was hypothesized that changing open chromatin regions in this cell type would contain HIF transcription factor binding motif sites. Upon activation, Hifa subunits heterodimerize with Hifb and the complex binds regulatory elements in the genome to affect transcription. Therefore, a motif enrichment analysis was conducted for four HIF family motifs with Fisher's exact test statistics. These included the JASPAR motifs for (i) Hif1a (MA1106.1), which has core motif redundancy with Hif2a (Schodel et al., *Nat Rev Mol* 5:343-354, 2011), (ii) Arnt aka Hif1b (MA0004.1), (iii) the Hifa-Hifb complex (MA0259.1), and a related Hifa binding partner Arntl (M0603.1) (FIG. 10B). Because there are few examples of DD-affected PV+ peaks at this threshold, PV+ enrichments were assessed within peaks that met a more lenient threshold of adjusted p-value<0.2 in DESeq2. As predicted, all four motifs were highly enriched within GPe PV+ DD-increasing peaks (the set of ATAC-seq peaks with increased accessibility upon DD) (FIG. 10C). Moreover, the motifs were not enriched in DD-increasing peak sets from other cell types with the exception of some weaker enrichment in Striatal PV+ neurons. Finally, sets of ATAC-seq peaks with decreased accessibility in DD (DD-decreasing) were not enriched for HIF motifs in any cell type including GPe PV+. These results provided further support for a cell type-specific induction of HIF signaling in GPe PV+ neurons upon DD.

To assess which additional transcription factors may be involved in the epigenetic response to DD, the analysis was extended to all motifs within the non-redundant JASPAR 2018 core vertebrates database (Khan et al., supra). Specific to DD-increasing GPe PV+ peaks and to a lesser extent also DD-increasing Striatal PV+ peaks, an enrichment for Ets-related transcription factor motifs including Gabpa was observed (GPe $p_{adj}$=1.25e-30: Striatum $p_{adj}$=1.41e-10). Gabpa is an essential regulator of many cellular respiration genes, including multiple cytochrome c oxidase subunits (Ongwijitwat et al., *Gene* 374:39-49, 2006).

DD-affected open chromatin regions in other cell types contained enrichments for several additional transcription factor binding motifs. Notably, DD-increasing peak sets in every cell population except for GPe PV+ were all enriched for the binding motifs of glucocorticoid receptor transcription factors Nr3c1, Nr3c2, and Ar ($p_{adj}$<0.01). Glucocorticoid receptors are emerging as key regulators of neuroinflammation and disruption of their proper regulation is thought to play a role in the onset of PD by allowing the infiltration of cytotoxins in the SNpc (Herrero et al., *Front Neuroanat* 9:1-12, 2015). These findings were consistent with similar stressors in the cortex, striatum, and GPe, which may contribute to the progression of PD.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A nucleic acid construct comprising:
(a) a nucleotide sequence encoding a tagged Sun1 fusion polypeptide, wherein the tagged Sun1 fusion polypeptide comprises (i) an N-truncated fragment of a Sun1 polypeptide that is 400 to 600 amino acids in length, and (ii) a tag polypeptide, and
(b) a promoter sequence specific for a selected neuronal cell type, wherein the selected neuronal cell type is parvalbumin positive (PV+) neurons,
wherein the promoter sequence is operably linked to the nucleotide sequence encoding the tagged Sun1 fusion polypeptide and is effective to drive expression of the sequence encoding the tagged Sun1 fusion polypeptide in the selected cell type, and wherein said tagged Sun1 fusion polypeptide localizes to the nuclear membrane after said expression.

2. The nucleic acid construct of claim 1, wherein the N-truncated fragment of the Sun1 polypeptide has at least 95% sequence identity to amino acids 208-757 of the mouse Sun1 protein having the amino acid sequence set forth in SEQ ID NO: 1.

3. The nucleic acid construct of claim 1, wherein the tag polypeptide is a fluorescent polypeptide.

4. The nucleic acid construct of claim 3, wherein the fluorescent polypeptide is a green fluorescent protein (GFP).

5. The nucleic acid construct of claim 4, wherein the amino acid sequence of the GFP is at least 95% identical to the superfolder GFP sequence set forth in SEQ ID NO:2.

6. The nucleic acid construct of claim 1, wherein the construct further comprises a virus sequence.

7. The nucleic acid construct of claim 6, wherein the virus sequence is an adeno-associated virus (AAV) sequence or a lentivirus sequence.

8. A virus particle comprising the nucleic acid construct of claim 1.

9. The virus particle of claim 8, wherein the virus is AAV or lentivirus.

10. A nucleic acid construct comprising:
(a) a nucleotide sequence encoding a tagged Sun1 fusion polypeptide, wherein the tagged Sun1 fusion polypeptide comprises (i) an N-truncated fragment of a Sun1 polypeptide that is 400 to 600 amino acids in length, and (ii) a sequence encoding a tag polypeptide,
(b) a first lox sequence flanking the 5' end of the sequence encoding the tagged Sun 1 fusion polypeptide and a second lox sequence flanking the 3' end of the sequence encoding the tagged Sun1 fusion polypeptide, and
(c) a promoter sequence specific for a selected neuronal cell type downstream of the lox sequence flanking the 3' end of the sequence encoding the tagged Sun1 fusion polypeptide, wherein the selected neuronal cell type is parvalbumin positive (PV+) neurons, such that the sequence encoding the tagged Sun1 fusion polypeptide is in reverse orientation with respect to the promoter, wherein said tagged Sun1 fusion polypeptide localizes to the nuclear membrane after being expressed.

11. The nucleic acid construct of claim 10, wherein the N-truncated Sun1 polypeptide has at least 95% sequence identity to amino acids 208-757 of the mouse Sun1 protein having the amino acid sequence set forth in SEQ ID NO:1.

12. The nucleic acid construct of claim 10, wherein the tag polypeptide is a fluorescent polypeptide.

13. The nucleic acid construct of claim 12, wherein the fluorescent polypeptide is a GFP.

14. The nucleic acid construct of claim 13, wherein the amino acid sequence of the GFP is at least 95% identical to the superfolder GFP sequence set forth in SEQ ID NO:2.

15. The nucleic acid construct of claim 10, wherein the construct further comprises a virus sequence.

16. The nucleic acid construct of claim 15, wherein the virus sequence is an AAV sequence or a lentivirus sequence.

17. A virus particle comprising the nucleic acid construct of claim 10.

18. The virus particle of claim 17, wherein the virus is AAV or lentivirus.

19. A method for labeling a selected neuronal cell type within a population of different cell types, comprising introducing into the population of different cell types a nucleic acid construct comprising:

(a) a nucleotide sequence encoding a tagged Sun1 fusion polypeptide, wherein the tagged Sun1 fusion polypeptide comprises (i) an N-truncated fragment of a Sun1 polypeptide that is 400 to 600 amino acids in length, and (ii) a sequence encoding a tag polypeptide, and (b) a promoter sequence specific for the selected neuronal cell type, wherein the selected neuronal cell type is parvalbumin positive (PV+) neurons, wherein the promoter sequence is operably linked to the sequence encoding the tagged Sun1 fusion polypeptide, and is effective to drive expression of the sequence encoding the tagged Sun1 fusion polypeptide in the selected cell type, and wherein the tagged Sun1 fusion polypeptide is expressed in and thereby labels the selected cell type, and wherein the tagged Sun1 fusion polypeptide localizes to the nuclear membrane after being expressed.

20. The method of claim 19, wherein the N-truncated fragment of the Sun1 polypeptide has at least 95% sequence identity to amino acids 208-757 of the mouse Sun1 protein having the amino acid sequence set forth in SEQ ID NO: 1.

21. A method for labeling a selected neuronal cell type within a population of different cell types, comprising:

(a) introducing into the population of different cell types:

(i) a first nucleic acid construct comprising:

(1) a nucleotide sequence encoding a tagged Sun1 fusion polypeptide and (2) a nucleotide sequence encoding a tag polypeptide, wherein the tagged Sun1 fusion polypeptide comprises an N-truncated fragment of a Sun1 polypeptide that is 400 to 600 amino acids in length, and (2) a first lox sequence flanking the 5' end of the sequence encoding the tagged Sun1 fusion polypeptide and a second lox sequence flanking the 3' end of the sequence encoding the tagged Sun1 fusion polypeptide, and (3) a promoter sequence downstream of the lox sequence flanking the 3' end of the sequence encoding the tagged Sun1 fusion polypeptide, such that the sequence encoding the tagged Sun1 fusion polypeptide is in reverse orientation with respect to the promoter, and (ii) a second nucleic acid construct comprising a sequence encoding a Cre recombinase operably linked to a promoter sequence specific for the selected neuronal cell type, wherein the selected cell type is parvalbumin positive (PV+) neurons and (b) incubating the population of different cell types under conditions in which the Cre recombinase is expressed in the selected neuronal cell type, wherein the expressed Cre recombinase excises the sequence encoding the tagged Sun1 fusion polypeptide from the nucleic acid construct and irreversibly re-inserts the sequence encoding the tagged Sun1 fusion polypeptide in the correct orientation for expression in the selected neuronal cell type.

22. The method of claim 21, wherein the N-truncated fragment of the Sun1 polypeptide has at least 95% sequence identity to amino acids 208-757 of the mouse Sun1 protein having the amino acid sequence set forth in SEQ ID NO: 1.

\* \* \* \* \*

SEQUENCE LISTING

<160> NUMBER OF SEQ ID NOS: 6

<210> SEQ ID NO 1
<211> LENGTH: 757
<212> TYPE: PRT
<213> ORGANISM: Mus musculus

<400> SEQUENCE: 1

Met Asp Phe Ser Arg Leu His Thr Tyr Thr Pro Pro Gln Cys Val Pro
1               5                   10                  15

Glu Asn Thr Gly Tyr Thr Tyr Ala Leu Ser Ser Ser Tyr Ser Ser Asp
            20                  25                  30

Ala Leu Asp Phe Glu Thr Glu His Lys Leu Glu Pro Val Phe Asp Ser
        35                  40                  45

Pro Arg Met Ser Arg Arg Ser Leu Arg Leu Val Thr Thr Ala Ser Tyr
    50                  55                  60

Ser Ser Gly Asp Ser Gln Ala Ile Asp Ser His Ile Ser Thr Ser Arg
65                  70                  75                  80

Ala Thr Pro Ala Lys Gly Arg Glu Thr Arg Thr Val Lys Gln Arg Arg
                85                  90                  95

Ser Ala Ser Lys Pro Ala Phe Ser Ile Asn His Leu Ser Gly Lys Gly
            100                 105                 110

Leu Ser Ser Ser Thr Ser His Asp Ser Ser Cys Ser Leu Arg Ser Ala
            115                 120                 125

Thr Val Leu Arg His Pro Val Leu Asp Glu Ser Leu Ile Arg Glu Gln
    130                 135                 140

Thr Lys Val Asp His Phe Trp Gly Leu Asp Asp Asp Gly Asp Leu Lys
145                 150                 155                 160

Gly Gly Asn Lys Ala Ala Thr Gln Gly Asn Gly Glu Leu Ala Ala Glu
                165                 170                 175

Val Ala Ser Ser Asn Gly Tyr Thr Cys Arg Asp Cys Arg Met Leu Ser
            180                 185                 190

Ala Arg Thr Asp Ala Leu Thr Ala His Ser Ala Ile His Gly Thr Thr
            195                 200                 205

Ser Arg Val Tyr Ser Arg Asp Arg Thr Leu Lys Pro Arg Lys Ala Ala
    210                 215                 220

Ser Gly Thr Phe Trp Trp Leu Gly Ser Gly Trp Tyr Gln Phe Val Thr
225                 230                 235                 240

Leu Ile Ser Trp Leu Asn Val Phe Leu Leu Thr Arg Cys Leu Arg Asn
                245                 250                 255

Ile Cys Lys Val Phe Val Leu Leu Leu Pro Leu Leu Leu Leu Leu Gly
            260                 265                 270

Ala Gly Val Ser Leu Trp Gly Gln Gly Asn Phe Phe Ser Leu Leu Pro
            275                 280                 285

Val Leu Asn Trp Thr Ala Met Gln Pro Thr Gln Arg Val Asp Asp Ser
    290                 295                 300

Lys Gly Met His Arg Pro Gly Pro Leu Pro Pro Ser Pro Pro Lys
305                 310                 315                 320

Val Asp His Lys Ala Ser Gln Trp Pro Gln Glu Ser Asp Met Gly Gln
            325                 330                 335

Lys Val Ala Ser Leu Ser Ala Gln Cys His Asn His Asp Glu Arg Leu
            340                 345                 350

Ala Glu Leu Thr Val Leu Leu Gln Lys Leu Gln Ile Arg Val Asp Gln
    355                 360                 365

-continued

```
Val Asp Asp Gly Arg Glu Gly Leu Ser Leu Trp Val Lys Asn Val Val
    370             375             380

Gly Gln His Leu Gln Glu Met Gly Thr Ile Glu Pro Pro Asp Ala Lys
385             390             395             400

Thr Asp Phe Met Thr Phe His His Asp His Glu Val Arg Leu Ser Asn
            405             410             415

Leu Glu Asp Val Leu Arg Lys Leu Thr Glu Lys Ser Glu Ala Ile Gln
            420             425             430

Lys Glu Leu Glu Glu Thr Lys Leu Lys Ala Gly Ser Arg Asp Glu Glu
        435             440             445

Gln Pro Leu Leu Asp Arg Val Gln His Leu Glu Leu Glu Leu Asn Leu
    450             455             460

Leu Lys Ser Gln Leu Ser Asp Trp Gln His Leu Lys Thr Ser Cys Glu
465             470             475             480

Gln Ala Gly Ala Arg Ile Gln Glu Thr Val Gln Leu Met Phe Ser Glu
            485             490             495

Asp Gln Gln Gly Gly Ser Leu Glu Trp Leu Leu Glu Lys Leu Ser Ser
            500             505             510

Arg Phe Val Ser Lys Asp Glu Leu Gln Val Leu Leu His Asp Leu Glu
            515             520             525

Leu Lys Leu Leu Gln Asn Ile Thr His His Ile Thr Val Thr Gly Gln
    530             535             540

Ala Pro Thr Ser Glu Ala Ile Val Ser Ala Val Asn Gln Ala Gly Ile
545             550             555             560

Ser Gly Ile Thr Glu Ala Gln Ala His Ile Ile Val Asn Asn Ala Leu
            565             570             575

Lys Leu Tyr Ser Gln Asp Lys Thr Gly Met Val Asp Phe Ala Leu Glu
            580             585             590

Ser Gly Gly Gly Ser Ile Leu Ser Thr Arg Cys Ser Glu Thr Tyr Glu
            595             600             605

Thr Lys Thr Ala Leu Leu Ser Leu Phe Gly Val Pro Leu Trp Tyr Phe
    610             615             620

Ser Gln Ser Pro Arg Val Val Ile Gln Pro Asp Ile Tyr Pro Gly Asn
625             630             635             640

Cys Trp Ala Phe Lys Gly Ser Gln Gly Tyr Leu Val Val Arg Leu Ser
            645             650             655

Met Lys Ile Tyr Pro Thr Thr Phe Thr Met Glu His Ile Pro Lys Thr
            660             665             670

Leu Ser Pro Thr Gly Asn Ile Ser Ser Ala Pro Lys Asp Phe Ala Val
            675             680             685

Tyr Gly Leu Glu Thr Glu Tyr Gln Glu Glu Gly Gln Pro Leu Gly Arg
        690             695             700

Phe Thr Tyr Asp Gln Glu Gly Asp Ser Leu Gln Met Phe His Thr Leu
705             710             715             720

Glu Arg Pro Asp Gln Ala Phe Gln Ile Val Glu Leu Arg Val Leu Ser
            725             730             735

Asn Trp Gly His Pro Glu Tyr Thr Cys Leu Tyr Arg Phe Arg Val His
            740             745             750

Gly Glu Pro Ile Gln
        755
```

<210> SEQ ID NO 2
<211> LENGTH: 238
<212> TYPE: PRT

```
<213> ORGANISM: Artificial
<220> FEATURE:
<223> OTHER INFORMATION: synthetic polypeptide

<400> SEQUENCE: 2

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Asn Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Thr Tyr Lys Thr Arg Ala Glu Val
                100                 105                 110

Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Lys Ile Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Val Leu Ser
            195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 3
<211> LENGTH: 2370
<212> TYPE: DNA
<213> ORGANISM: Artificial
<220> FEATURE:
<223> OTHER INFORMATION: synthetic oligonucleotide

<400> SEQUENCE: 3
atgacctcca gggtgtactc cagagacagg actctcaaac cacggaaggc agcctcggga      60
accttctggt ggctagggag cggctggtac caatttgtta ctttgatttc ttggctgaat     120
gtctttcttc ttaccaggtg ccttcgaaat atttgcaagg tttttgtctt gctcctccca     180
ctcctacttt tactaggtgc tggtgtctcc ctgtggggcc agggaaactt cttctcactc     240
ctaccagtgc tgaactggac ggccatgcag ccaacacaga gggtggacga ttccaagggc     300
atgcatagac ctggccctct tcccccgagc ccacctccaa aggttgatca caaggcttcc     360
cagtggcctc aggagagtga catggggcag aaggtagctt ctttgagtgc gcagtgccac     420
aaccatgatg agagacttgc agagctgaca gtcctgcttc agaaactaca gatacgggta     480
gaccaagtgg atgacggcag ggaagggctg tcactgtggg tcaagaatgt ggttggacag     540
```

-continued

```
cacctgcagg agatgggcac catagaacca cctgatgcta agactgactt catgactttc      600
caccatgacc atgaagtgcg tctctccaac ttggaagatg ttcttagaaa actgacagaa      660
aaatctgagg ctatccagaa ggagctggaa gaaaccaagc tgaaagcagg cagcagggat      720
gaagagcagc ccctccttga ccgtgtgcag cacctagaac tggaactgaa cctgttgaag      780
tcacagctgt cagactggca gcatctgaag accagctgtg agcaggctgg ggcccgcatc      840
caggagactg tgcagctcat gttctctgag gatcagcagg gcggttccct cgagtggcta      900
ttagagaagc tttcttctcg gttcgtgagc aaggatgagc tgcaggtgct cttacatgac      960
cttgagctga aactgctgca gaatatcaca caccacatca ccgtgacagg acaggccccg     1020
acatccgagg ctattgtgtc tgccgtgaat caggcaggga tttcaggaat cacagaagcg     1080
caagcacata tcattgtgaa caatgctctg aagctgtact cccaagacaa gacggggatg     1140
gtggactttg ctctggagtc tggaggtggc agcatcctaa gcactcggtg ctctgagacc     1200
tatgagacca agacggcact gctgagcctg tttgggggtcc cactgtggta cttctcacag     1260
tcacctcgag tggtgatcca gcccgacatc tacccaggga attgctgggc gttcaaaggt     1320
tcccaggggt acctggtggt gcggttgtcc atgaagatct acccaaccac attcaccatg     1380
gaacacattc caaagacact atcacccact ggtaacatct ccagtgcccc caaagacttt     1440
gcagtctatg gactggaaac ggagtatcaa gaagaggggc agcctctggg acggttcacc     1500
tatgaccagg aaggagactc actccagatg ttccacacac tggaaagacc tgaccaagcc     1560
ttccagatag tagagctccg ggtcctgtcc aactggggcc accctgagta cacttgcctc     1620
taccggttcc gagtccacgg agagcccatc cagatgagca aggagaaga actttttcact     1680 ggagttgtcc caattcttgt tgaattagat ggtgatgtta atgggcacaa attttctgtc     1740
cgtggagagg gtgaaggtga tgctacaaac ggaaaactca cccttaaatt tatttgcact     1800
actggaaaac tacctgttcc atggccaaca cttgtcacta ctctgaccta tggtgttcaa     1860
tgcttttccc gttatccgga tcacatgaaa cggcatgact ttttcaagag tgccatgccc     1920
gaaggttatg tacaggaacg cactatatct ttcaaagatg acgggaccta caagacgcgt     1980
gctgaagtca gtttgaagg tgatacccctt gttaatcgta tcgagttaaa aggtattgat     2040
tttaaagaag atggaaacat tctcggacac aaactcgagt acaactttaa ctcacacaat     2100
gtatacatca cggcagacaa acaaaagaat ggaatcaaag ctaacttcaa aattcgccac     2160
aacgttgaag atggttccgt tcaactagca gaccattatc aacaaaatac tccaattggc     2220
gatggccctg tccttttacc agacaaccat tacctgtcga cacaatctgt cctttcgaaa     2280
gatcccaacg aaaagcgtga ccacatggtc cttcttgagt ttgtaactgc tgctgggatt     2340
acacatggca tggatgagct ctacaaataa                                     2370
```

```
<210> SEQ ID NO 4
<211> LENGTH: 500
<212> TYPE: DNA
<213> ORGANISM: Artificial
<220> FEATURE:
<223> OTHER INFORMATION: synthetic oligonucleotide

<400> SEQUENCE: 4
attggtttgc cttacacgct ttgttgaact gcatttgcca tgactccata gagaaaaaca       60
cgccgaaaag cttctctagg tggttccac atcttcttgt ggattccgtg gactcgggtc      120
aactagcaga gtgatgtcag ctgctataca tagactcaca tggagttttg ctaagacagg      180
ctcacgtgct gaggcaagac acgtggtaag gcaagacctg tagaggacac ttggtgtttt      240
```

```
gaggcagtat aaataggact caacggacgg tgatggaggc tgggcttgct tgcataacta      300
gctttgcagt gcttcttggt ctcgcgtctt cactgacctt cgatttgttg agagcggcac      360
agttgagaac ttcccctggc atccctggtg gtcctaattc ctcctgctaa ctccagccaa      420
ttcggctgaa gcctggcagt ttctgctagg tcgggccacc gctgctgatt cgtatttgct      480
atcccaactc taccaatctg                                                  500
```

```
<210> SEQ ID NO 5
<211> LENGTH: 7274
<212> TYPE: DNA
<213> ORGANISM: Artificial
<220> FEATURE:
<223> OTHER INFORMATION: synthetic oligonucleotide

<400> SEQUENCE: 5
```

```
cctgcaggca gctgcgcgct cgctcgctca ctgaggccgc ccgggcaaag cccgggcgtc       60
gggcgacctt tggtcgcccg gcctcagtga gcgagcgagc gcgcagagag ggagtggcca      120
actccatcac taggggttcc tgcggccgca cgcgtgcgat cgccatatga ggcctcattg      180
gccattgtaa ttggtttgcc ttacacgctt tgttgaactg catttgccat gactccatag      240
agaaaaacac gccgaaaagc ttctctaggt ggttcccaca tcttcttgtg gattccgtgg      300
actcgggtca actagcagag tgatgtcagc tgctatacat agactcacat ggagttttgc      360
taagacaggc tcacgtgctg aggcaagaca cgtggtaagg caagacctgt agaggacact      420
tggtgttttg aggcagtata aataggactc aacggacggt gatggaggct gggcttgctt      480
gcataactag ctttgcagtg cttcttggtc tcgcgtcttc actgaccttc gatttgttga      540
gagcggcaca gttgagaact tcccctggca tccctggtgg tcctaattcc tcctgctaac      600
tccagccaat tcggctgaag cctggcagtt tctgctaggt cgggccaccg ctgctgattc      660
gtatttgcta tcccaactct accaatctgg aattaattcg ctgtctgcga gggccagctg      720
ttggggtgag tactccctct caaaagcggg catgacttct gcgctaagat tgtcagtttc      780
caaaaacgag gaggatttga tattcacctg gcccgcggtg atgcctttga gggtggccgc      840
gtccatctgg tcagaaaaga caatcttttt gttgtcaagc ttgaggtgtg gcaggcttga      900
gatctggcca tacacttgag tgacaatgac atccactttg cctttctctc cacaggtgtc      960
cactcccagg tccaactgca ggtcgcgact agcggatcca atgacctcca gggtgtactc     1020
cagagacagg actctcaaac cacggaaggc agcctcggga accttctggt ggctagggag     1080
cggctggtac caatttgtta ctttgatttc ttggctgaat gtctttcttc ttaccaggtg     1140
ccttcgaaat atttgcaagg ttttttgtctt gctcctccca ctcctacttt tactaggtgc     1200
tggtgtctcc ctgtggggcc agggaaactt cttctcactc ctaccagtgc tgaactggac     1260
ggccatgcag ccaacacaga gggtggacga ttccaagggc atgcatagac ctggccctct     1320
tcccccgagc ccacctccaa aggttgatca caaggcttcc cagtggcctc aggagagtga     1380
catggggcag aaggtagctt ctttgagtgc gcagtgccac aaccatgatg agagacttgc     1440
agagctgaca gtcctgcttc agaaactaca gatacgggta gaccaagtgg atgacggcag     1500
ggaagggctg tcactgtggg tcaagaatgt ggttggacag cacctgcagg agatgggcac     1560
catagaacca cctgatgcta agactgactt catgactttc caccatgacc atgaagtgcg     1620
tctctccaac ttggaagatg ttcttagaaa actgacagaa aaatctgagg ctatccagaa     1680
ggagctggaa gaaaccaagc tgaaagcagg cagcagggat gaagagcagc ccctccttga     1740
```

-continued

```
ccgtgtgcag cacctagaac tggaactgaa cctgttgaag tcacagctgt cagactggca    1800
gcatctgaag accagctgtg agcaggctgg ggcccgcatc caggagactg tgcagctcat    1860
gttctctgag gatcagcagg gcggttccct cgagtggcta ttagagaagc tttcttctcg    1920
gttcgtgagc aaggatgagc tgcaggtgct cttacatgac cttgagctga aactgctgca    1980
gaatatcaca caccacatca ccgtgacagg acaggccccg acatccgagg ctattgtgtc    2040
tgccgtgaat caggcaggga tttcaggaat cacagaagcg caagcacata tcattgtgaa    2100
caatgctctg aagctgtact cccaagacaa gacggggatg gtggactttg ctctggagtc    2160
tggaggtggc agcatcctaa gcactcggtg ctctgagacc tatgagacca agacggcact    2220
gctgagcctg tttggggtcc cactgtggta cttctcacag tcacctcgag tggtgatcca    2280
gcccgacatc tacccaggga attgctgggc gttcaaaggt tcccaggggt acctggtggt    2340
gcggttgtcc atgaagatct acccaaccac attcaccatg gaacacattc caaagacact    2400
atcacccact ggtaacatct ccagtgcccc caaagacttt gcagtctatg gactggaaac    2460
ggagtatcaa gaagaggggc agcctctggg acggttcacc tatgaccagg aaggagactc    2520
actccagatg ttccacacac tggaaagacc tgaccaagcc ttccagatag tagagctccg    2580
ggtcctgtcc aactggggcc accctgagta cacttgcctc taccggttcc gagtccacgg    2640
agagcccatc cagatgagca aaggagaaga acttttcact ggagttgtcc caattcttgt    2700
tgaattagat ggtgatgtta atgggcacaa attttctgtc cgtggagagg gtgaaggtga    2760
tgctacaaac ggaaaactca cccttaaatt tatttgcact actggaaaac tacctgttcc    2820
atggccaaca cttgtcacta ctctgaccta tggtgttcaa tgcttttccc gttatccgga    2880
tcacatgaaa cggcatgact ttttcaagag tgccatgccc gaaggttatg tacaggaacg    2940
cactatatct ttcaaagatg acgggaccta caagacgcgt gctgaagtca agtttgaagg    3000
tgataccctt gttaatcgta tcgagttaaa aggtattgat tttaaagaag atggaaacat    3060
tctcggacac aaactcgagt acaactttaa ctcacacaat gtatacatca cggcagacaa    3120
acaaaagaat ggaatcaaag ctaacttcaa aattcgccac aacgttgaag atggttccgt    3180
tcaactagca gaccattatc aacaaaatac tccaattggc gatggccctg tccttttacc    3240
agacaaccat tacctgtcga cacaatctgt cctttcgaaa gatcccaacg aaaagcgtga    3300
ccacatggtc cttcttgagt ttgtaactgc tgctgggatt acacatggca tggatgagct    3360
ctacaaataa ggcgcggaat cgatatcaa gcttatcgat aatcaacctc tggattacaa    3420
aatttgtgaa agattgactg gtattcttaa ctatgttgct ccttttacgc tatgtggata    3480
cgctgcttta atgcctttgt atcatgctat tgcttcccgt atggctttca ttttctcctc    3540
cttgtataaa tcctggttgc tgtctcttta tgaggagttg tggcccgttg tcaggcaacg    3600
tggcgtggtg tgcactgtgt ttgctgacgc aacccccact ggttggggca ttgccaccac    3660
ctgtcagctc ctttccggga ctttcgcttt ccccctccct attgccacgg cggaactcat    3720
cgccgcctgc cttgcccgct gctggacagg ggctcggctg ttgggcactg acaattccgt    3780
ggtgttgtcg gggaaatcat cgtcctttcc ttggctgctc gcctgtgttg ccacctggat    3840
tctgcgcggg acgtccttct gctacgtccc ttcggccctc aatccagcgg accttccttc    3900
ccgcggcctg ctgccggctc tgcggcctct tccgcgtctt cgccttcgcc ctcagacgag    3960
tcggatctcc ctttgggccg cctccccgca tcgataccga gcgctgctcg agagatctac    4020
gggtggcatc cctgtgaccc ctccccagtg cctctcctgg ccctggaagt tgccactcca    4080
gtgcccacca gccttgtcct aataaaatta agttgcatca ttttgtctga ctaggtgtcc    4140
```

-continued

```
ttctataata ttatggggtg gaggggggtg gtatggagca aggggcaagt tgggaagaca      4200
acctgtaggg cctgcggggt ctattgggaa ccaagctgga gtgcagtggc acaatcttgg      4260
ctcactgcaa tctccgcctc ctgggttcaa gcgattctcc tgcctcagcc tcccgagttg      4320
ttgggattcc aggcatgcat gaccaggctc agctaatttt tgtttttttg gtagagacgg      4380
ggtttcacca tattggccag gctggtctcc aactcctaat ctcaggtgat ctacccacct      4440
tggcctccca aattgctggg attacaggcg tgaaccactg ctcccttccc tgtccttctg      4500
attttgtagg taaccacgtg cggaccgagc ggccgcagga acccctagtg atggagttgg      4560
ccactccctc tctgcgcgct cgctcgctca ctgaggccgg gcgaccaaag gtcgcccgac      4620
gcccgggctt tgcccgggcg gcctcagtga gcgagcgagc gcgcagctgc ctgcaggggc      4680
gcctgatgcg gtattttctc cttacgcatc tgtgcggtat ttcacaccgc atacgtcaaa      4740
gcaaccatag tacgcgccct gtagcggcgc attaagcgcg gcgggtgtgg tggttacgcg      4800
cagcgtgacc gctacacttg ccagcgccct agcgcccgct cctttcgctt tcttcccttc      4860
ctttctcgcc acgttcgccg gctttccccg tcaagctcta aatcgggggc tccctttagg      4920
gttccgattt agtgctttac ggcacctcga ccccaaaaaa cttgatttgg gtgatggttc      4980
acgtagtggg ccatcgccct gatagacggt ttttcgccct ttgacgttgg agtccacgtt      5040
ctttaatagt ggactcttgt tccaaactgg aacaacactc aaccctatct cgggctattc      5100
ttttgattta taagggattt tgccgatttc ggcctattgg ttaaaaaatg agctgattta      5160
acaaaaattt aacgcgaatt ttaacaaaat attaacgttt acaattttat ggtgcactct      5220
cagtacaatc tgctctgatg ccgcatagtt aagccagccc cgacacccgc caacacccgc      5280
tgacgcgccc tgacgggctt gtctgctccc ggcatccgct tacagacaag ctgtgaccgt      5340
ctccgggagc tgcatgtgtc agaggttttc accgtcatca ccgaaacgcg cgagacgaaa      5400
gggcctcgtg atacgcctat ttttataggt taatgtcatg ataataatgg tttcttagac      5460
gtcaggtggc acttttcggg gaaatgtgcg cggaacccct atttgtttat ttttctaaat      5520
acattcaaat atgtatccgc tcatgagaca ataaccctga taaatgcttc aataatattg      5580
aaaaaggaag agtatgagta ttcaacattt ccgtgtcgcc cttattccct tttttgcggc      5640
attttgcctt cctgtttttg ctcacccaga aacgctggtg aaagtaaaag atgctgaaga      5700
tcagttgggt gcacgagtgg gttacatcga actggatctc aacagcggta agatccttga      5760
gagttttcgc cccgaagaac gttttccaat gatgagcact tttaaagttc tgctatgtgg      5820
cgcggtatta tcccgtattg acgccgggca agagcaactc ggtcgccgca tacactattc      5880
tcagaatgac ttggttgagt actcaccagt cacagaaaag catcttacgg atggcatgac      5940
agtaagagaa ttatgcagtg ctgccataac catgagtgat aacactgcgg ccaacttact      6000
tctgacaacg atcggaggac cgaaggagct aaccgctttt ttgcacaaca tgggggatca      6060
tgtaactcgc cttgatcgtt gggaaccgga gctgaatgaa gccataccaa acgacgagcg      6120
tgacaccacg atgcctgtag caatggcaac aacgttgcgc aaactattaa ctggcgaact      6180
acttactcta gcttcccggc aacaattaat agactggatg gaggcggata aagttgcagg      6240
accacttctg cgctcggccc ttccggctgg ctggtttatt gctgataaat ctggagccgg      6300
tgagcgtggg tctcgcggta tcattgcagc actggggcca gatggtaagc cctcccgtat      6360
cgtagttatc tacacgacgg ggagtcaggc aactatggat gaacgaaata gacagatcgc      6420
tgagataggt gcctcactga ttaagcattg gtaactgtca gaccaagttt actcatatat      6480
```

-continued

```
actttagatt gatttaaaac ttcattttta atttaaaagg atctaggtga agatcctttt    6540
tgataatctc atgaccaaaa tcccttaacg tgagttttcg ttccactgag cgtcagaccc    6600
cgtagaaaag atcaaaggat cttcttgaga tccttttttt ctgcgcgtaa tctgctgctt    6660
gcaaacaaaa aaaccaccgc taccagcggt ggtttgtttg ccggatcaag agctaccaac    6720 tcttttttccg aaggtaactg gcttcagcag agcgcagata ccaaatactg tccttctagt    6780
gtagccgtag ttaggccacc acttcaagaa ctctgtagca ccgcctacat acctcgctct    6840
gctaatcctg ttaccagtgg ctgctgccag tggcgataag tcgtgtctta ccgggttgga    6900
ctcaagacga tagttaccgg ataaggcgca gcggtcgggc tgaacggggg gttcgtgcac    6960
acagcccagc ttggagcgaa cgacctacac cgaactgaga tacctacagc gtgagctatg    7020
agaaagcgcc acgcttcccg aagggagaaa ggcggacagg tatccggtaa gcggcagggt    7080
cggaacagga gagcgcacga gggagcttcc aggggggaaac gcctggtatc tttatagtcc    7140
tgtcgggttt cgccacctct gacttgagcg tcgatttttg tgatgctcgt cagggggggcg    7200 gagcctatgg aaaaacgcca gcaacgcggc ctttttacgg ttcctggcct tttgctggcc    7260
ttttgctcac atgt                                                      7274
```

<210> SEQ ID NO 6
<211> LENGTH: 789
<212> TYPE: PRT
<213> ORGANISM: Artificial
<220> FEATURE:
<223> OTHER INFORMATION: synthetic polypeptide

<400> SEQUENCE: 6

```
Met Thr Ser Arg Val Tyr Ser Arg Asp Arg Thr Leu Lys Pro Arg Lys
1               5                   10                  15

Ala Ala Ser Gly Thr Phe Trp Trp Leu Gly Ser Gly Trp Tyr Gln Phe
            20                  25                  30

Val Thr Leu Ile Ser Trp Leu Asn Val Phe Leu Leu Thr Arg Cys Leu
        35                  40                  45

Arg Asn Ile Cys Lys Val Phe Val Leu Leu Leu Pro Leu Leu Leu Leu
    50                  55                  60

Leu Gly Ala Gly Val Ser Leu Trp Gly Gln Gly Asn Phe Phe Ser Leu
65                  70                  75                  80

Leu Pro Val Leu Asn Trp Thr Ala Met Gln Pro Thr Gln Arg Val Asp
                85                  90                  95

Asp Ser Lys Gly Met His Arg Pro Gly Pro Leu Pro Pro Ser Pro Pro
            100                 105                 110

Pro Lys Val Asp His Lys Ala Ser Gln Trp Pro Gln Glu Ser Asp Met
        115                 120                 125

Gly Gln Lys Val Ala Ser Leu Ser Ala Gln Cys His Asn His Asp Glu
        130                 135                 140

Arg Leu Ala Glu Leu Thr Val Leu Leu Gln Lys Leu Gln Ile Arg Val
145                 150                 155                 160

Asp Gln Val Asp Asp Gly Arg Glu Gly Leu Ser Leu Trp Val Lys Asn
                165                 170                 175

Val Val Gly Gln His Leu Gln Glu Met Gly Thr Ile Glu Pro Pro Asp
            180                 185                 190

Ala Lys Thr Asp Phe Met Thr Phe His His Asp His Glu Val Arg Leu
        195                 200                 205

Ser Asn Leu Glu Asp Val Leu Arg Lys Leu Thr Glu Lys Ser Glu Ala
    210                 215                 220
```

-continued

```
Ile Gln Lys Glu Leu Glu Glu Thr Lys Leu Lys Ala Gly Ser Arg Asp
225                 230                 235                 240

Glu Glu Gln Pro Leu Leu Asp Arg Val Gln His Leu Glu Leu Glu Leu
                245                 250                 255

Asn Leu Leu Lys Ser Gln Leu Ser Asp Trp Gln His Leu Lys Thr Ser
                260                 265                 270

Cys Glu Gln Ala Gly Ala Arg Ile Gln Glu Thr Val Gln Leu Met Phe
                275                 280                 285

Ser Glu Asp Gln Gln Gly Gly Ser Leu Glu Trp Leu Leu Glu Lys Leu
                290                 295                 300

Ser Ser Arg Phe Val Ser Lys Asp Glu Leu Gln Val Leu Leu His Asp
305                 310                 315                 320

Leu Glu Leu Lys Leu Leu Gln Asn Ile Thr His His Ile Thr Val Thr
                325                 330                 335

Gly Gln Ala Pro Thr Ser Glu Ala Ile Val Ser Ala Val Asn Gln Ala
                340                 345                 350

Gly Ile Ser Gly Ile Thr Glu Ala Gln Ala His Ile Ile Val Asn Asn
                355                 360                 365

Ala Leu Lys Leu Tyr Ser Gln Asp Lys Thr Gly Met Val Asp Phe Ala
                370                 375                 380

Leu Glu Ser Gly Gly Gly Ser Ile Leu Ser Thr Arg Cys Ser Glu Thr
385                 390                 395                 400

Tyr Glu Thr Lys Thr Ala Leu Leu Ser Leu Phe Gly Val Pro Leu Trp
                405                 410                 415

Tyr Phe Ser Gln Ser Pro Arg Val Val Ile Gln Pro Asp Ile Tyr Pro
                420                 425                 430

Gly Asn Cys Trp Ala Phe Lys Gly Ser Gln Gly Tyr Leu Val Val Arg
                435                 440                 445

Leu Ser Met Lys Ile Tyr Pro Thr Thr Phe Thr Met Glu His Ile Pro
                450                 455                 460

Lys Thr Leu Ser Pro Thr Gly Asn Ile Ser Ser Ala Pro Lys Asp Phe
465                 470                 475                 480

Ala Val Tyr Gly Leu Glu Thr Glu Tyr Gln Glu Glu Gly Gln Pro Leu
                485                 490                 495

Gly Arg Phe Thr Tyr Asp Gln Glu Gly Asp Ser Leu Gln Met Phe His
                500                 505                 510

Thr Leu Glu Arg Pro Asp Gln Ala Phe Gln Ile Val Glu Leu Arg Val
                515                 520                 525

Leu Ser Asn Trp Gly His Pro Glu Tyr Thr Cys Leu Tyr Arg Phe Arg
                530                 535                 540

Val His Gly Glu Pro Ile Gln Met Ser Lys Gly Glu Glu Leu Phe Thr
545                 550                 555                 560

Gly Val Val Pro Ile Leu Val Glu Leu Asp Gly Asp Val Asn Gly His
                565                 570                 575

Lys Phe Ser Val Arg Gly Glu Gly Glu Gly Asp Ala Thr Asn Gly Lys
                580                 585                 590

Leu Thr Leu Lys Phe Ile Cys Thr Thr Gly Lys Leu Pro Val Pro Trp
                595                 600                 605

Pro Thr Leu Val Thr Thr Leu Thr Tyr Gly Val Gln Cys Phe Ser Arg
                610                 615                 620

Tyr Pro Asp His Met Lys Arg His Asp Phe Phe Lys Ser Ala Met Pro
625                 630                 635                 640
```

-continued

```
Glu Gly Tyr Val Gln Glu Arg Thr Ile Ser Phe Lys Asp Asp Gly Thr
            645             650             655

Tyr Lys Thr Arg Ala Glu Val Lys Phe Glu Gly Asp Thr Leu Val Asn
            660             665             670

Arg Ile Glu Leu Lys Gly Ile Asp Phe Lys Glu Asp Gly Asn Ile Leu
            675             680             685

Gly His Lys Leu Glu Tyr Asn Phe Asn Ser His Asn Val Tyr Ile Thr
        690             695             700

Ala Asp Lys Gln Lys Asn Gly Ile Lys Ala Asn Phe Lys Ile Arg His
705             710             715             720

Asn Val Glu Asp Gly Ser Val Gln Leu Ala Asp His Tyr Gln Gln Asn
            725             730             735

Thr Pro Ile Gly Asp Gly Pro Val Leu Leu Pro Asp Asn His Tyr Leu
            740             745             750

Ser Thr Gln Ser Val Leu Ser Lys Asp Pro Asn Glu Lys Arg Asp His
            755             760             765

Met Val Leu Leu Glu Phe Val Thr Ala Ala Gly Ile Thr His Gly Met
        770             775             780

Asp Glu Leu Tyr Lys
785
```